(12) United States Patent
Hongo et al.

(10) Patent No.: US 11,058,502 B2
(45) Date of Patent: Jul. 13, 2021

(54) SUPPORT ARM DEVICE

(71) Applicant: SONY CORPORATION, Tokyo (JP)

(72) Inventors: Kazuo Hongo, Kanagawa (JP); Kenichiro Nagasaka, Tokyo (JP)

(73) Assignee: SONY CORPORATION, Tokyo (JP)

( * ) Notice: Subject to any disclaimer, the term of this patent is extended or adjusted under 35 U.S.C. 154(b) by 433 days.

(21) Appl. No.: 15/768,932

(22) PCT Filed: Aug. 9, 2016

(86) PCT No.: PCT/JP2016/073507
§ 371 (c)(1),
(2) Date: Apr. 17, 2018

(87) PCT Pub. No.: WO2017/077755
PCT Pub. Date: May 11, 2017

(65) Prior Publication Data
US 2019/0053863 A1    Feb. 21, 2019

(30) Foreign Application Priority Data

Nov. 4, 2015  (JP) .............................. JP2015-216450
Jan. 13, 2016  (JP) .............................. JP2016-004587

(51) Int. Cl.
*B25J 9/06* (2006.01)
*A61B 34/37* (2016.01)
(Continued)

(52) U.S. Cl.
CPC .............. *A61B 34/37* (2016.02); *A61B 34/30* (2016.02); *B25J 9/06* (2013.01); *B25J 9/1065* (2013.01);
(Continued)

(58) Field of Classification Search
CPC ........ B25J 9/1065; B25J 9/06; B25J 17/0283; B25J 18/007; A61B 34/37; A61B 34/30
See application file for complete search history.

(56) References Cited

U.S. PATENT DOCUMENTS

| 5,397,323 A * | 3/1995 | Taylor | ................. B25J 19/0008 606/130 |
| 10,610,323 B2 * | 4/2020 | Wang | ..................... A61B 90/10 |

(Continued)

FOREIGN PATENT DOCUMENTS

| JP | 03-104574 A | 5/1991 |
| JP | 09-295289 A | 11/1997 |

(Continued)

OTHER PUBLICATIONS

International Search Report and Written Opinion of PCT Application No. PCT/JP2016/073507, dated Oct. 11, 2016, 06 pages.

*Primary Examiner* — Randell J Krug
(74) *Attorney, Agent, or Firm* — Chip Law Group

(57) ABSTRACT

A support arm device includes a first drive part that is fixed to a base part and cause a first drive shaft to perform shaft rotation, a second drive part that is fixed to the base part and cause a second drive shaft to perform shaft rotation, and an arm part including at least one parallel link and that supports a predetermined tool. The arm part is caused to change an attitude to cause the predetermined tool to perform a predetermined rotational motion by the first drive part and the second drive part being driven.

17 Claims, 42 Drawing Sheets

(51) Int. Cl.
*B25J 18/00* (2006.01)
*A61B 34/30* (2016.01)
*B25J 9/10* (2006.01)
*B25J 17/02* (2006.01)
*A61B 90/00* (2016.01)
*A61B 34/00* (2016.01)
*A61B 90/50* (2016.01)
*A61B 17/28* (2006.01)

(52) U.S. Cl.
CPC ......... *B25J 17/0283* (2013.01); *B25J 18/007* (2013.01); *A61B 17/2812* (2013.01); *A61B 34/74* (2016.02); *A61B 2034/301* (2016.02); *A61B 2034/742* (2016.02); *A61B 2090/034* (2016.02); *A61B 2090/035* (2016.02); *A61B 2090/064* (2016.02); *A61B 2090/506* (2016.02)

(56) References Cited

U.S. PATENT DOCUMENTS

| | | | | |
|---|---|---|---|---|
| 2002/0169440 | A1* | 11/2002 | Jensen | A61B 34/70 606/1 |
| 2003/0233102 | A1* | 12/2003 | Nakamura | A61B 17/3476 606/130 |
| 2004/0024385 | A1* | 2/2004 | Stuart | B25J 17/0266 606/1 |
| 2006/0264915 | A1* | 11/2006 | Jensen | A61B 34/71 606/1 |
| 2015/0351857 | A1* | 12/2015 | Vander Poorten | B25J 18/007 606/130 |

FOREIGN PATENT DOCUMENTS

| | | |
|---|---|---|
| WO | 09-295289 A | 11/1997 |
| WO | 2014/108545 A1 | 7/2014 |

\* cited by examiner

SUPPORT ARM DEVICE

CROSS REFERENCE TO RELATED APPLICATIONS

This application is a U.S. National Phase of International Patent Application No. PCT/JP2016/073507 filed on Aug. 9, 2016, which claims priority benefit of Japanese Patent Application No. JP 2015-216450 filed in the Japan Patent Office on Nov. 4, 2015 and also claims priority benefit of Japanese Patent Application No. JP 2016-004587 filed in the Japan Patent Office on Jan. 13, 2016. Each of the above-referenced applications is hereby incorporated herein by reference in its entirety.

TECHNICAL FIELD

The present disclosure relates to a support arm device.

BACKGROUND ART

Recently, industrial robots and surgical robots operating using parallel links are known. A robot configured using parallel links is characterized in that a tip side of an arm part constituted by parallel links can be set to be relatively light or can be formed at a relatively low cost. In addition, a robot configured using parallel links is also characterized in that, since motors can be disposed on a root side rather than a tip side of an arm part, weights of the motors seldom impose a burden on output of the motors.

In the field of medicine, for example, a device that enables pivotal motions around a remote center of motion (RCM) is used. Such a device includes an arm part including at least one parallel link, and enables a supported endoscope or an end-effector such as forceps to perform pivotal motions around the RCM. Thus, such a device can be used as a surgical robot that helps an endoscope or an end-effector move through an insertion hole formed by incising a body surface of a patient during a surgery (e.g., refer to Patent Literature 1).

CITATION LIST

Patent Literature

Patent Literature 1: WO 2014/108545

DISCLOSURE OF INVENTION

Technical Problem

The apparatus disclosed in Patent Literature 1 deforms a parallelogram structure or a rhombus structure of an arm part by driving three motors to perform pivotal motions around the RCM. However, one motor among the three motors of the apparatus disclosed in Patent Literature 1 causes the other two motors and parts including relatively heavy constituent elements such as a counterweight in addition to the arm part to revolve.

Specifically, while one motor among the three motors is fixed to a base part, the other two motors are not fixed to the base part and are disposed in a movable part that is caused to revolve by the motor fixed to the base part. In addition, the movable part that is caused to revolve by the motor fixed to the base part has a counterweight for maintaining the arm part to be in a self-standing state. Thus, the motor fixed to the base part needs output that can cause a relatively heavy part to operate.

Therefore, the present disclosure proposes a novel and improved support arm device that can reduce output of motors.

Solution to Problem

According to the present disclosure, there is provided a support arm device including: a first drive part configured to be fixed to a base part and cause a first drive shaft to perform shaft rotation; a second drive part configured to be fixed to the base part and cause a second drive shaft to perform shaft rotation; and an arm part including at least one parallel link and configured to support a predetermined tool. The arm part is caused to change an attitude to cause the predetermined tool to perform a rotational motion by the first drive part and the second drive part being driven.

Advantageous Effects of Invention

According to the present disclosure described above, output of a motor can be reduced. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
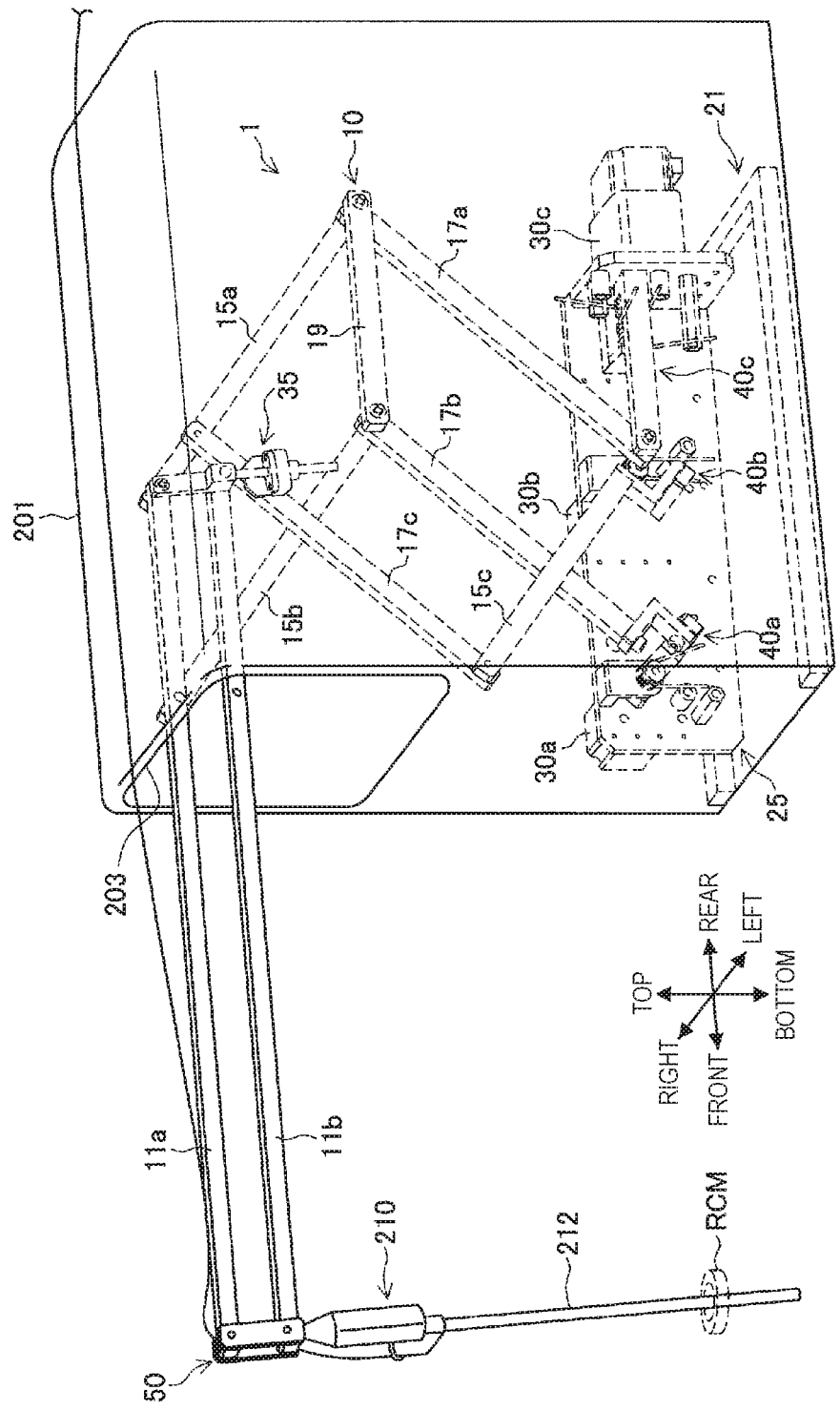
FIG. 1 is a perspective diagram showing an example of a configuration of a support arm device according to a first embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.
1. First embodiment
1-1. Overall configuration of support arm device
1-2. Specific configuration of support arm device
1-3. Attitude of arm part
1-4. Control device
1-5. Modified example
1-6. Conclusion
2. Second embodiment
2-1. Configuration of support arm device
2-2. Attitude of arm part
2-3. Conclusion
3. Third embodiment
3-1. Configuration of support arm device
3-2. Attitude of arm part
3-3. Conclusion
4. Fourth embodiment
4-1. Configuration of support arm device
4-2. Attitude of arm part
4-3. Conclusion 1. First Embodiment <1-1. Overall Configuration of Support Arm Device>

An overall configuration of a support arm device 1 according to a first embodiment of the present disclosure will be described with reference to FIG. 1. FIG. 1 is a perspective diagram showing an example of a configuration of the support arm device 1 according to the present embodiment.

Note that a direction of an axis of a first drive shaft 31a or a third drive shaft 31b will also be referred to as a left-right direction, a direction of an axis of a second drive shaft 31c will also be referred to as a front-back direction, and a direction orthogonal to the first drive shaft 31a or the third drive shaft 31b and the second drive shaft 31c will also be referred to as a top-bottom direction.

The support arm device 1 according to the present embodiment is an example of a medical support arm device whose support part 50 supports an endoscope 210 serving as a medical instrument. The support arm device 1 according to the present embodiment can configure a slave-side device in a master-slave surgery system. Therefore, the support arm device 1 and the endoscope 210 may be configured to be remotely operable by an operator.

The support arm device 1 includes an arm part 10 including at least one parallel link. When the arm part 10 is operated by a first motor 30a, a second motor 30c, and a third motor 30b, a pivotal motion made around a predetermined RCM (a pivotal motion made around the RCM will be simply referred to as a "pivotal motion" below) and a translational motion made along a straight line passing through the RCM are realized. A specific configuration of the support arm device 1 will be described below.

The endoscope 210 is supported by the support part 50 of the support arm device 1. The endoscope 210 is a rigid scope having a long insertion part 212, and for example, a tip of the insertion part 212 is inserted into a body during a laparotomy. The insertion part 212 of the endoscope 210 performs pivotal motions in accordance with control of the support arm device 1. That is, the insertion part 212 of the endoscope 210 performs rotational motions in the front-back and left-right directions such that the insertion part 212 or an axis of the insertion part 212 surely passes through the RCM no matter how variously the arm part 10 is operated. In addition, the insertion part 212 of the endoscope 210 performs translational motions along the straight line passing through the RCM in addition to the pivotal motions in accordance with control of the support arm device 1. The RCM is a virtual center of revolution, and in a case in which the support arm device 1 is used for a medical purpose, the RCM corresponds to, for example, an insertion slot formed by incising a body surface of a patient or the like. The insertion part 212 of the endoscope 210 performs pivotal motions and translational motions using the RCM as an immovable point, and thereby an imaging position, an imaging angle, or the like is changed.

A medical instrument supported by the support arm device 1 is not limited to the endoscope 210, and may be a surgical instrument, for example, an end-effector for gripping a biological tissue of a patient or a medical device, or the like. Such a surgical instrument may have a long insertion part connected to a part supported by the support part 50 of the support arm device 1 and a grip part at a tip of the insertion part. The insertion part of the surgical instrument also performs pivotal motions and translational motions when the support arm device 1 is controlled. Accordingly, when a surgery is performed, attitudes of the support arm device 1 are controlled so that the end-effector can have a desired position and attitude with respect to a biological tissue of a patient.

The support arm device 1 may have a cover 201. The cover 201 is a housing that contains the support arm device 1 therein. In a case in which the support arm device 1 is used for a medical purpose, it is important for hygiene of the device to be maintained. Thus, as the cover 201 is provided, exposure of the inner mechanical structure can be avoided. In addition, as the cover 201 is provided, an operator and the like can be prevented from mistakenly touching the arm part 10 and being injured or the like.

The cover 201 has an opening 203, and a part of the support arm device 1 is led to the outside from the opening 203. In the example of the support arm device 1 shown in FIG. 1, a first link 11a and a second link 11b constituting a part of the arm part 10 are led to the outside, and the support part 50 is provided at tips of the first link 11a and the second link 11b. Assuming that the support arm device 1 is installed on a side of an operating table and used, for example, the first link 11a and the second link 11b may be led 500 mm from the opening 203 of the cover 201. The opening 203 of the cover 201 is formed not to limit a range within which the first link 11a and the second link 11b can move when the endoscope 210 is allowed to perform pivotal motions and translational motions. Note that an appearance of the cover 201 is not particularly limited. In addition, the cover 201 may be omitted in the support arm device 1 according to the present embodiment.

<1-2. Specific Configuration of the Support Arm Device>

Figure 2:
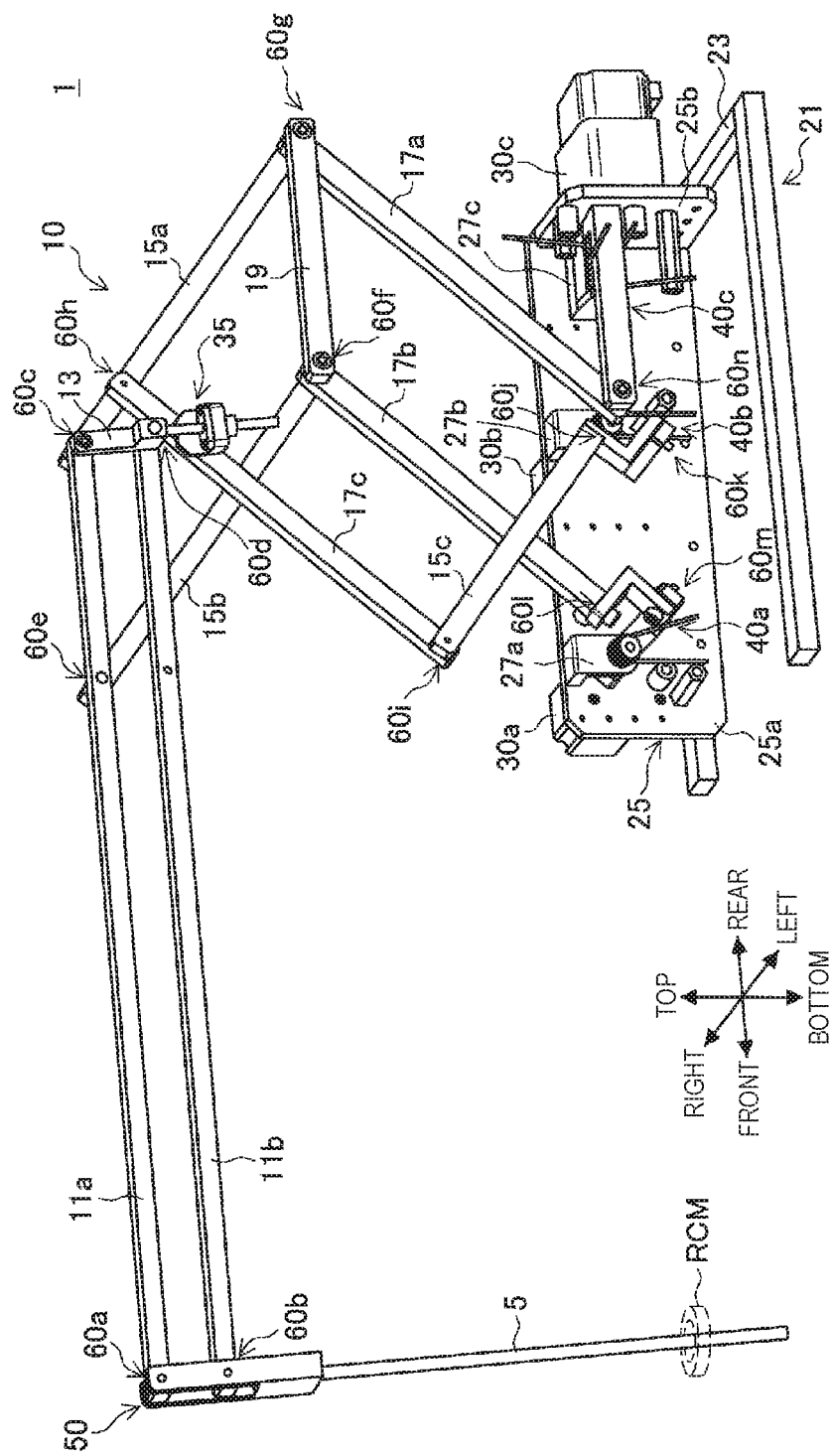
FIG. 2 is a perspective diagram showing the support arm device according to the embodiment.
Figure 3:
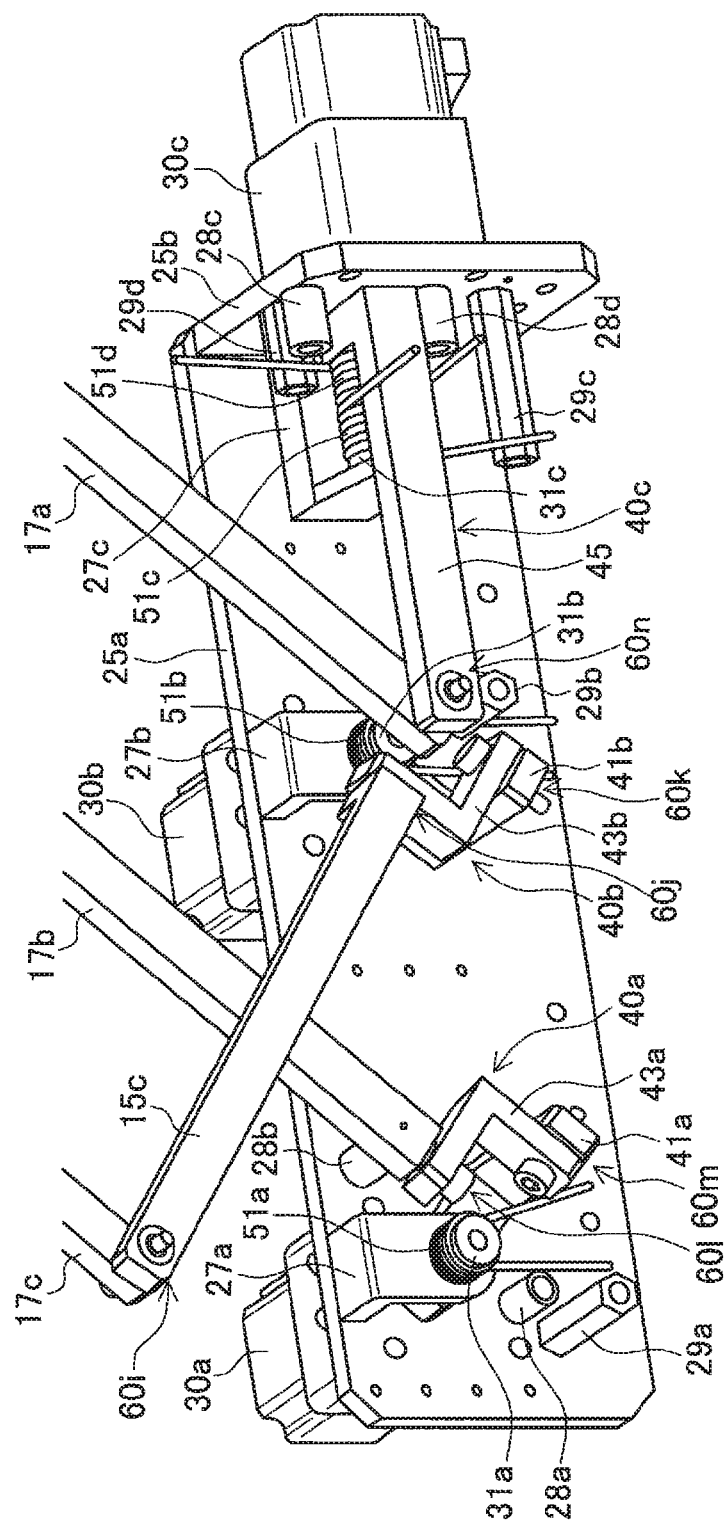
FIG. 3 is a perspective diagram showing a configuration of the support arm device around a fixing part.

Next, the configuration of the support arm device 1 according to the present embodiment will be described in detail with reference to FIG. 2 and FIG. 3. FIG. 2 shows the support arm device 1 shown in FIG. 1 from which the cover 201 is omitted. FIG. 3 is a perspective diagram showing peripheries of a fixing part 25 of the support arm device 1. In FIG. 2, instead of the endoscope 210, a long rod-like surgical instrument (a tool) 5 is supported by the support part 50. The surgical instrument 5 corresponds to the insertion part 212 of the endoscope 210 or an insertion part of another surgical instrument.

The support arm device 1 includes a base part 21, the first motor 30a, the second motor 30c, the third motor 30b, and the arm part 10 with the support part 50. The first motor 30a, the second motor 30c, and the third motor 30b are attached to the base part 21 using, for example, bolts, rivets, and the like.

(1-2-1. Base Part)

The base part 21 includes a fixing part 25 and a leg part 23 that supports the fixing part 25 to be stabilized. Although the leg part 23 has a U shape in which aggregates are connected, a shape of the leg part 23 is not limited thereto. Instead of the leg part 23, a plate or a three-dimensional pedestal may be used. The fixing part 25 includes a first plate surface part 25a and a second plate surface part 25b that are orthogonal to each other. The first plate surface part 25a and the second surface plate part 25b are fixed to two orthogonal sides of the U-shaped leg part 23. Note that a shape of the fixing part 25 is not particularly limited as well. The base part 21 is an immovable part whose position and attitude are not changed while the first motor 30a, the second motor 30c, and the third motor 30b are driven, and is basically kept immovable while the arm part 10 is operated. Note that the base part 21 may include, for example, casters that enable the base part to be movable on a floor.

(1-2-2. Drive Part)

The first motor 30a, the second motor 30c, and the third motor 30b are examples of a first drive part, a second drive part, and a third drive part, respectively. The first motor 30a, the second motor 30c, and the third motor 30b can be, for example, electric servomotors, each are connected to electric wiring, which is not illustrated, and are driven through control of energization by a control device. The first motor 30a causes the first drive shaft 31a to perform shaft rotation. The second motor 30c causes the second drive shaft 31c to perform shaft rotation. The third motor 30b causes the third drive shaft 31b to perform shaft rotation. In the support arm device 1 according to the present embodiment, although output shafts of the first motor 30a, the second motor 30c, and the third motor 30b are set to the first drive shaft 31a, the second drive shaft 31c, and the third drive shaft 31b, respectively, the output shafts and the drive shafts of the motors may be formed using different shaft members and connected via a gear or the like.

The first drive shaft 31a is rotatably supported by a bearing part 27a. The second drive shaft 31c is rotatably supported by a bearing part 27c. The third drive shaft 31b is rotatably supported by a bearing part 27b. The first drive shaft 31a and the third drive shaft 31b are disposed in parallel at an equal interval. Although it is better for the first drive shaft 31a and the third drive shaft 31b to be disposed on parallel surfaces, if the first drive shaft 31a and the third drive shaft 31b are in an equidistant parallel state, pivotal motions around the RCM under control of the first motor 30a, the second motor 30c, and the third motor 30b become easy. In addition, if the first drive shaft 31a and the third drive shaft 31b are in the equidistant parallel state, deterioration of transmission efficiency of motor torque can be prevented. Furthermore, if the first drive shaft 31a and the third drive shaft 31b are in the equidistant parallel state, a design of the device becomes easier and production efficiency is accordingly improved.

In addition, the axis of the second drive shaft 31c is orthogonal to each of the axis of the first drive shaft 31a and the axis of the third drive shaft 31b. In the support arm device 1 according to the present embodiment, the axis of the first drive shaft 31a, and the axis of the axis of the second drive shaft 31c and the third drive shaft 31b are disposed on a surface parallel to an installation surface on which the base part 21 is installed. The RCM, which serves as the center of pivotal motions of the surgical instrument 5, is further disposed on the axis of the second drive shaft 31c. Note that the first drive part, the second drive part, and the third drive part are not limited to motors as long as the drive parts each can cause the first drive shaft 31a, the second drive shaft 31c, and the third drive shaft 31b to perform shaft rotation.

(1-2-3. Arm Part)

The arm part 10 includes at least one parallel link constituted by a plurality of links. Here, a "parallel link" refers to a parallelogram structure or a rhombus structure formed by a plurality of links. The arm part 10 includes a plurality of joint parts 60a to 60n, and the first link 11a, the second link 11b, a third link 13, a fourth link 15a, a fifth link 15b, a sixth link 15c, a seventh link 17a, an eighth link 17b, a ninth link 17c, and a tenth link 19 which are revolvably connected to each other by the joint parts 60a to 60n. Furthermore, the arm part 10 has the support part 50 for supporting the surgical instrument 5 at a tip thereof.

The plurality of links constituting the arm part 10 can be formed using, for example, any of various materials such as aluminum, stainless steel, or a resin material. A constituent material may be selected focusing on lightness or on production cost.

A configuration of the support part 50 is not particularly limited as long as the support part can support the surgical instrument 5 such as an endoscope or an end-effector. For example, the surgical instrument 5 may be fixed using a bolt, a rivet, or the like, or a portion of the surgical instrument 5 supported by the support part 50 may be set to have a specific shape corresponding to the support part 50 so that the surgical instrument 5 is attachable thereto or detachable therefrom. In addition, the support part 50 may include a rotation mechanism that causes the long surgical instrument 5 to perform shaft rotation. For example, a portion supporting the surgical instrument 5 may be set to be rotatably by a motor or the like. If the support part 50 has a rotation mechanism, for example, a 3D endoscope or the like can be supported and used as the surgical instrument 5.

Figure 4:
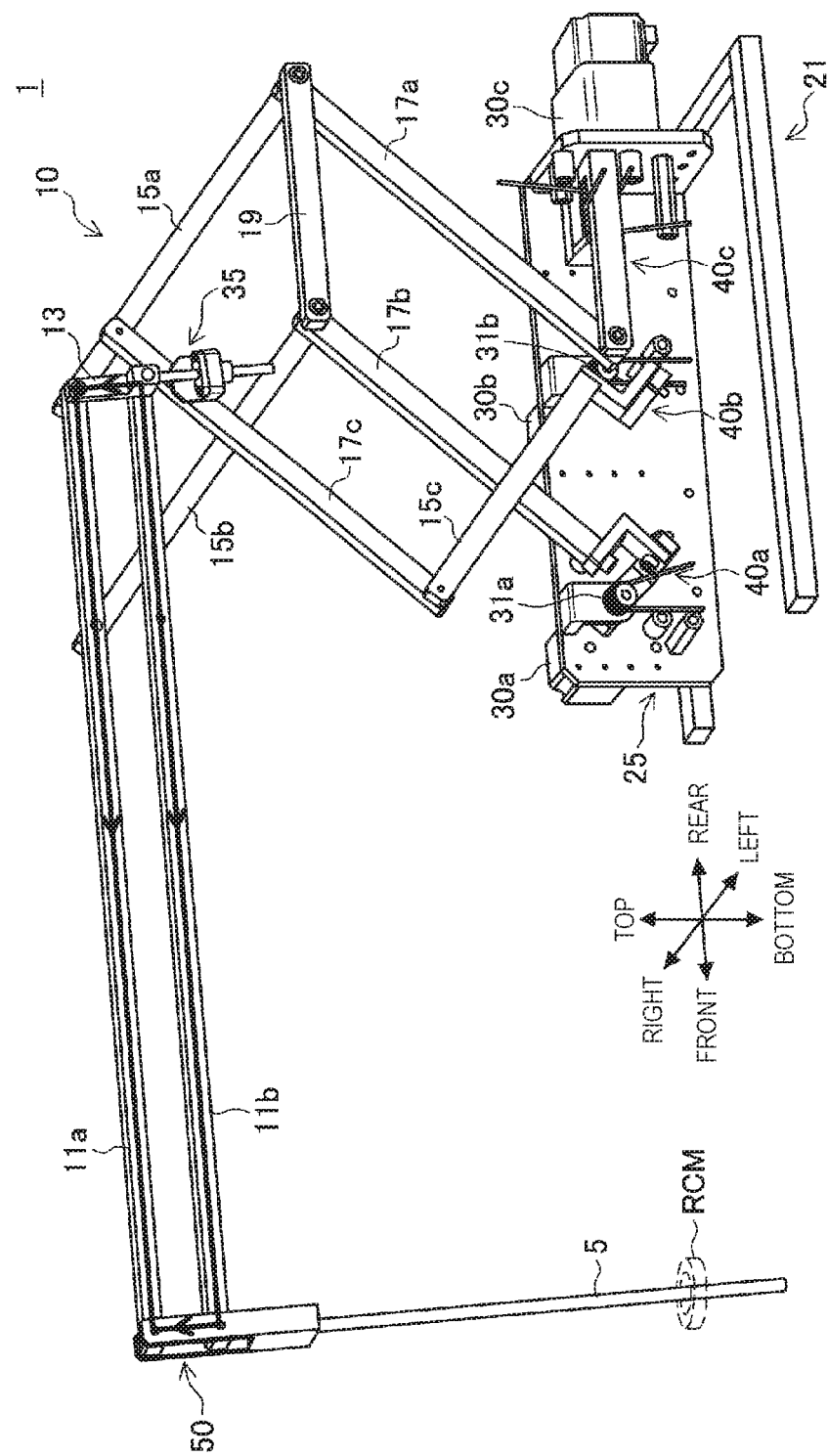
FIG. 4 is a diagram for describing a parallelogram structure of an arm part.
Figure 5:
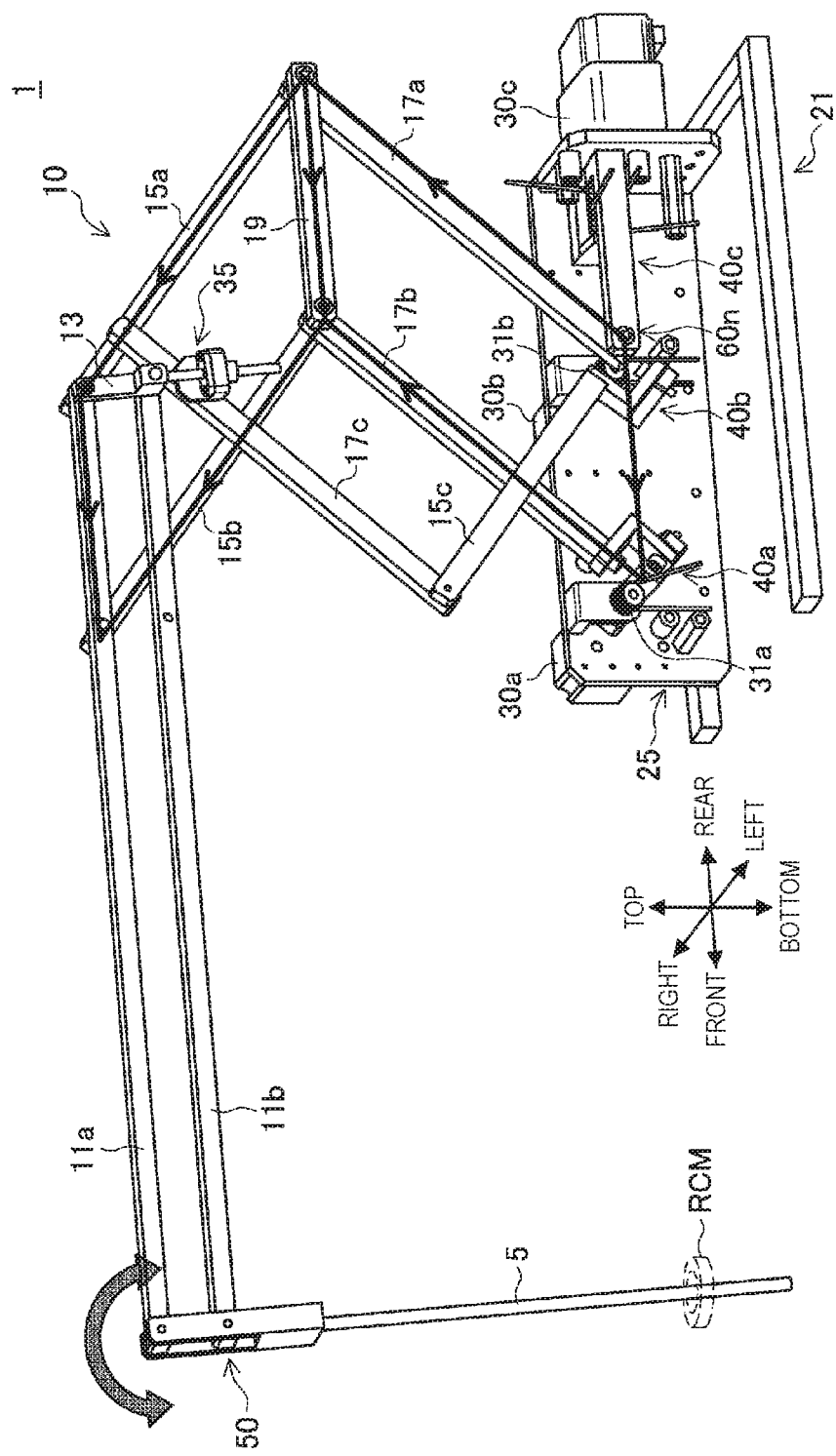
FIG. 5 is a diagram for describing a parallelogram structure of an arm part.
Figure 6:
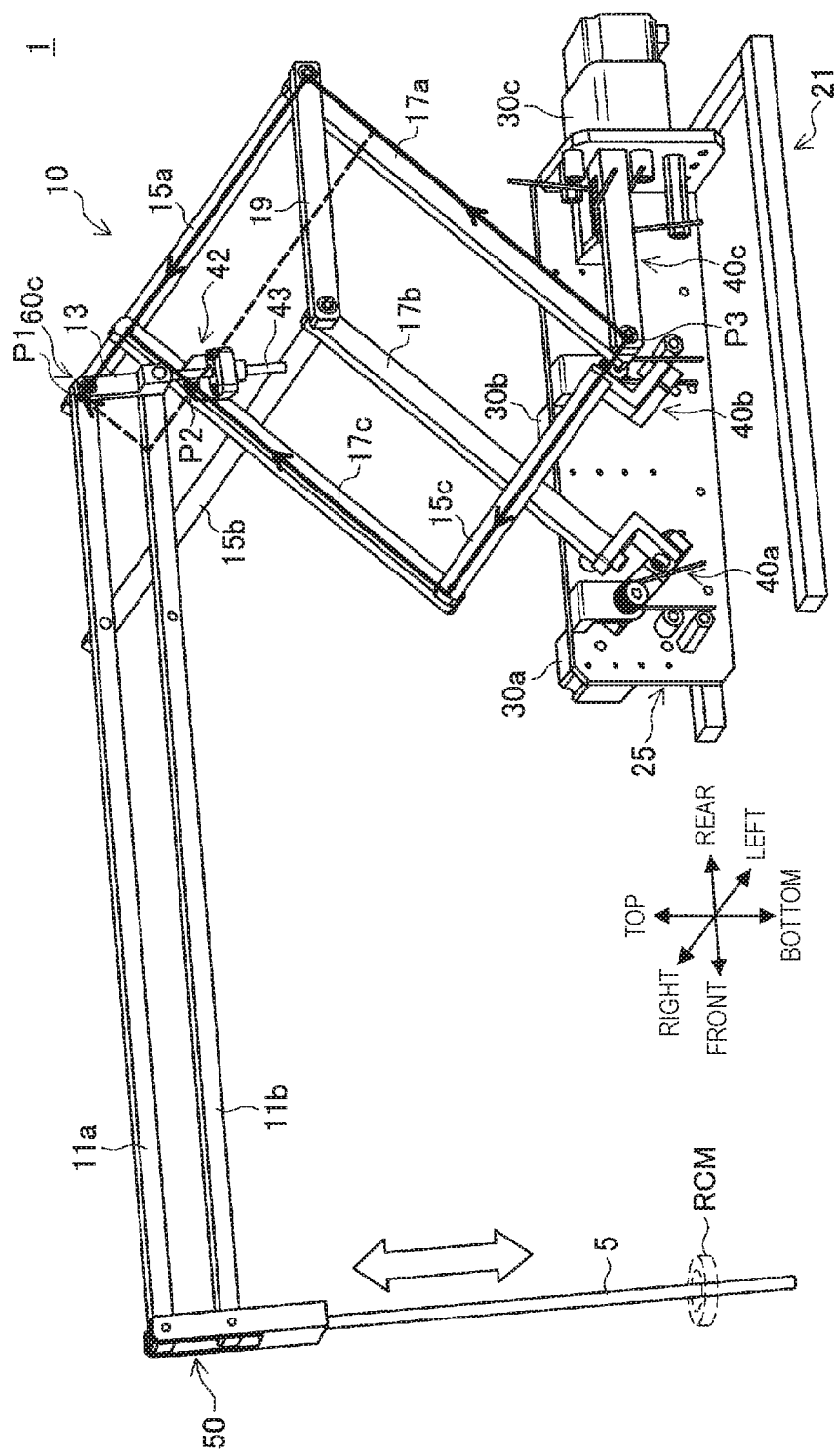
FIG. 6 is a diagram for describing a rhombus structure of the arm part.

FIG. 4 to FIG. 6 are illustrative diagrams showing the parallelogram structure and the rhombus structure formed in the arm part 10. As shown in FIG. 4, a parallel link is formed by the first link 11a, the second link 11b, the third link 13, and the support part 50. In addition, another parallel link is formed by the fourth link 15a, the fifth link 15b, the tenth link 19, and the first link 11a, as shown in FIG. 5. Although the fifth link 15b and the second link 11b intersect, the links are not connected. In addition, another parallel link is formed by the seventh link 17a, the eighth link 17b, and the tenth link 19. Furthermore, another parallel link is formed by the fourth link 15a, the sixth link 15c, the seventh link 17a, and the ninth link 17c, as shown in FIG. 6. Although the sixth link 15c and the eighth link 17b intersect, the links are not connected. Likewise, although the ninth link 17c and the fifth link 15b intersect, the links are not connected. Meanwhile, the third link 13 is connected to the ninth link 17c via a guide structure 35.

Note that, among the plurality of links, the eighth link 17b corresponds to a first drive link, the seventh link 17a corresponds to a second drive link, and the sixth link 15c corresponds to a third drive link.

The plurality of links are present within a common link configuration plane regardless of attitudes of the arm part 10. That is, the plurality of parallel links formed by the plurality of links are present within the common link configuration plane regardless of attitudes of the arm part 10. Thus, the support arm device 1 can reduce a left-right direction width of the arm part. Here, the "link configuration plane" is a plane that is regarded as a plane with a predetermined thickness, and while the plane does not change during operations of the arm part 10 in the front-rear direction and the top-bottom direction, an inclination of the plane can change during operations of the arm part 10 in the left-right direction. In the support arm device 1 according to the present embodiment, the link configuration plane has a thickness of three links.

Figure 7:
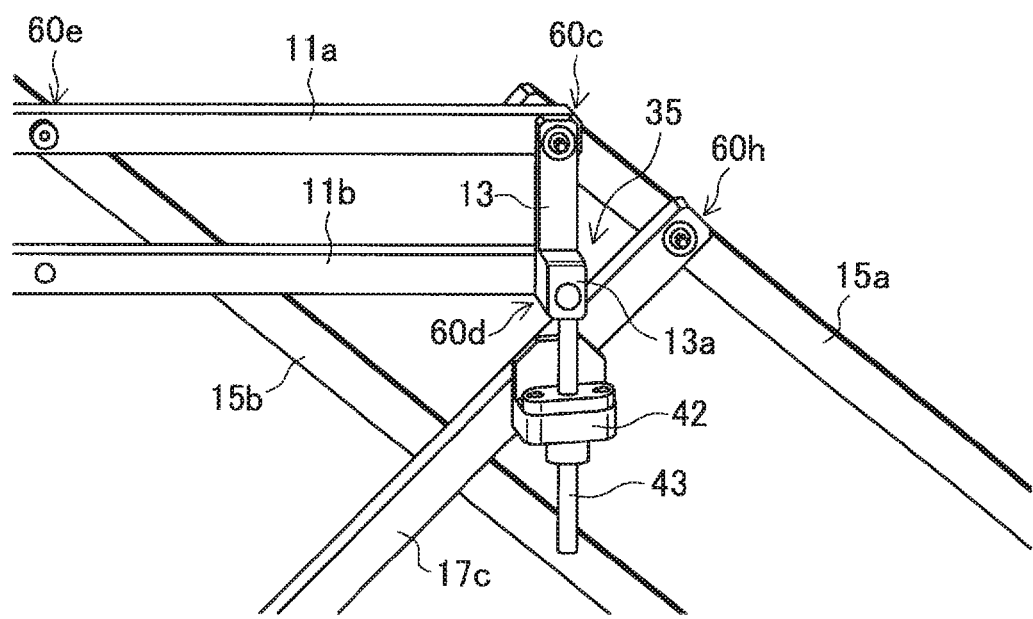
FIG. 7 is a diagram for describing a guide structure.

FIG. 7 is an illustrative diagram showing the guide structure 35. The guide structure 35 includes a guide pin 43 and a linear bushing 42. The third link 13 has the guide pin 43 extending in an extension direction of the third link 13. The guide pin 43 is axis-rotatably supported by a bearing part 13a, which is provided in the third link 13, at a position of the joint part 60d of the second link 11b and the third link 13. In addition, the guide pin 43 is inserted into the linear bushing 42 that is revolvably fixed to the ninth link 17c such that the guide pin is movable forward and backward in the linear bushing 42. The guide pin 43 is directed to the axis of the third drive shaft 31b regardless of attitude of the arm part 10. That is, the third link 13 is directed to a direction of the axis of the third drive shaft 31b at all times. Since the support part 50 and the surgical instrument 5 are parallel to the third link 13, the surgical instrument 5 or the axis of the surgical instrument 5 passes through the RCM at all times regardless of attitudes of the arm part 10.

Returning to FIG. 2 and FIG. 3, the eighth link (the first drive link) 17b is connected to the first drive shaft 31a via a first orthogonal joint part 40a. The first orthogonal joint part 40a includes two L-shaped members 41a and 43a and two joint parts 60l and 60m. One piece of one L-shaped member 41a is connected to the first drive shaft 31a and extends in a direction orthogonal to the axis of the first drive shaft 31a. In addition, the other piece of the L-shaped member 41a extends in a direction of the axis of the first drive shaft 31a and is revolvably connected to the other L-shaped member 43a by the joint part 60m. One piece of the other L-shaped member 43a connected to the one L-shaped member 41a extends on a surface along the direction of the axis of the first drive shaft 31a. In addition, the other piece of the L-shaped member 43a extends in a direction orthogonal to the axis of the first drive shaft 31a and is revolvably connected to the eighth link 17b by the joint part 60l.

A revolution range of the L-shaped member 41a of the first orthogonal joint part 40a in accordance with rotation of the first drive shaft 31a is regulated by stoppers 28a and 28b. In other words, the L-shaped member 41a revolves from a position at which the member abuts on the stopper 28a to a position at which the member abuts on the stopper 28b.

Figure 8:
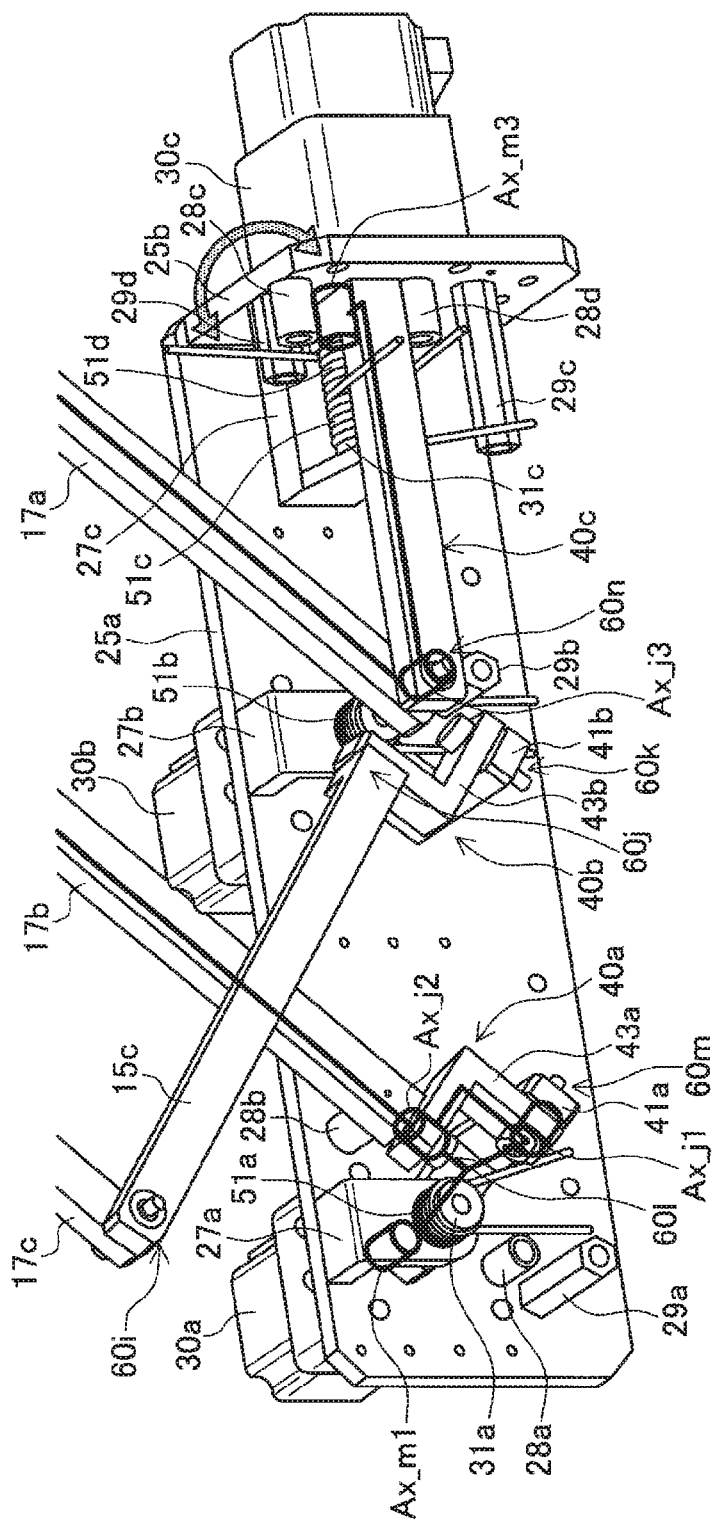
FIG. 8 is a diagram for describing a structure of an orthogonal joint part of a base part.

In FIG. 8, a rotation axis Ax_m1 of the first drive shaft 31a in the first orthogonal joint part 40a, a rotation axis Ax_j1 of the joint part 60m connecting the two L-shaped members 41a and 43a, and a rotation axis Ax_j2 of the join part 60l for the L-shaped member 43a and the eighth link 17b are indicated by thick lines. The three axes Ax_m1, Ax_j1, and Ax_j2 for the rotation axes of the first drive shaft 31a and the two joint parts 60l and 60m are orthogonal to each other and intersect at one point. Thus, when the first motor 30a is driven, the first drive shaft 31a performs shaft rotation and the eighth link 17b revolves around the axis Ax_m1 of the first drive shaft 31a regardless of attitudes of the arm part 10.

Figure 9:
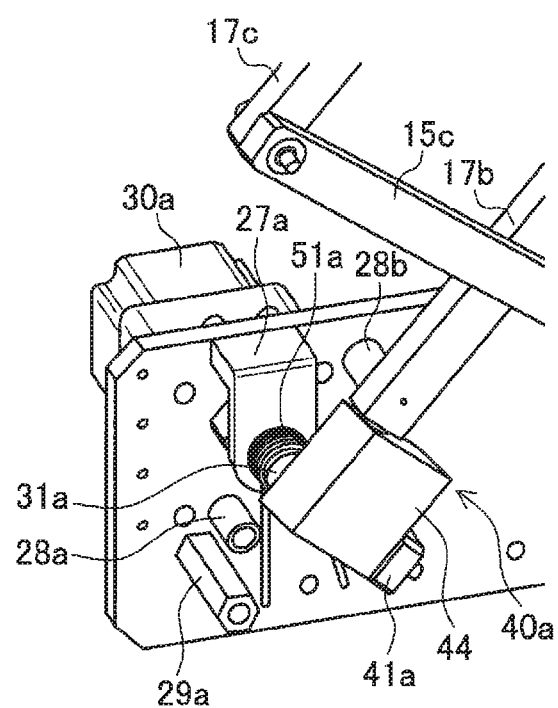
FIG. 9 is a diagram showing another structure of the orthogonal joint part of the base part.

Note that the first orthogonal joint part 40a may connect the L-shaped member 41a and a square columnar member 44 as shown in FIG. 9, in addition to connecting the two L-shaped members 41a and 41b. In short, an L-shaped or a square columnar member is a member having two orthogonal surfaces, and a member having such two surfaces can be used.

FIG. 5 is an illustrative diagram showing a state in which an inclination of the surgical instrument 5 in the front-rear direction changes with respect to the RCM in 2 parallelogram structures. As shown in FIG. 5, the seventh link 17a revolves with respect to the joint part 60n while maintaining a state parallel to the eighth link 17b in accordance with revolution of the eighth link 17b. Accordingly, the parallel link formed by the seventh link 17a, the eighth link 17b and the tenth link 19 revolves in the front-back direction. At this time, the tenth link 19 revolves while maintaining a state parallel to a line connecting the axis of the first drive shaft 31a and the axis of the third drive shaft 31b.

In addition, the tenth link 19 is an element forming the parallel link with the first link 11a, the fourth link 15a, and the fifth link 15b, and the first link 11a revolves while maintaining a state parallel to the tenth link 19 in accordance with revolution of the tenth link 19. The first link 11a forms the parallel link with the support part 50, the second link 11b, and the third link 13. Thus, the first link 11a and the second link 11b revolve while maintaining a state parallel to the installation surface at all time. At this time, since the third link 13 is directed to the third drive shaft 31b due to the guide structure 35 at all times, the surgical instrument 5 or the axis of the surgical instrument 5 passes through the RCM at all times.

As described above, by the first motor 30a and the third motor 30b being driven to cause the first link 11a and the second link 11b to revolve, the surgical instrument 5 can revolve in the front-rear direction with respect to the RCM. Note that, when the surgical instrument 5 revolves only in the front-back direction, the plurality of parallel links of the arm part 10 are deformed along a specific link configuration plane while being presenting within the link configuration plane.

Returning to FIG. 2 and FIG. 3, the sixth link (the third drive link) 15c is connected to the third drive shaft 31b via a third orthogonal joint part 40b. The third orthogonal joint part 40b includes the two L-shaped members 41b and 43b and two joint parts 60j and 60k. One piece of one L-shaped members 41b is connected to the third drive shaft 31b and extends in a direction orthogonal to the axis of the third drive shaft 31b. In addition, the other piece of the L-shaped members 41b extends in the direction of the axis of the third drive shaft 31b and is revolvably connected to the other L-shaped members 43b by the joint part 60k.

One piece of the other L-shaped members 43b connected to the one L-shaped members 41b extends on a surface along the direction of the axis of the third drive shaft 31b. In addition, the other piece of L-shaped members 43b extends in a direction orthogonal to the axis of the third drive shaft 31b, and is revolvably connected to the sixth link 15c by the joint part 60j. The three axes including the rotation axes of the third drive shaft 31b and the two joint parts 60j and 60k are orthogonal to each other and intersect at one point. Thus, similarly to the first orthogonal joint part 40a, by the third motor 30b being driven, the third drive shaft 31b performs shaft rotation and the sixth link 15c revolves with respect to the axis of the third drive shaft 31b, regardless of attitudes of the arm part 10.

If the third motor 30b is driven to cause the third drive shaft 31b to perform shaft rotation in the same direction at the same rotation speed as the first drive shaft 31a, the parallel link formed by the fourth link 15a, the sixth link 15c, the seventh link 17a, and the ninth link 17c revolve with respect to the axis of the third drive shaft 31b while maintaining the shape. On the other hand, if the third drive shaft 31b is caused to perform shaft rotation at a different rotation speed from the first drive shaft 31a or in a reverse direction thereto, the shape of the parallel link formed by the fourth link 15a, the sixth link 15c, the seventh link 17a, and the ninth link 17c is changed.

FIG. 6 is an illustrative diagram showing a state in which the surgical instrument 5 performs a translational motion in the top-bottom direction so as to pass through the RCM in two rhombus structures. As shown in FIG. 6, when a virtual line that passes through a rotation axis P2 of the linear bushing 42 and is parallel to the fourth link 15a and a virtual line that passes through the joint part 60c connecting the first link 11a and the fourth link 15a and is parallel to the ninth link 17c are drawn, two rhombus structures that have the third link 13 and an extended line thereof as a diagonal line are formed. When the shape of the parallel link formed by the fourth link 15a, the sixth link 15c, the seventh link 17a, and the ninth link 17c is changed, the above-described two rhombus structures contract in the direction of the diagonal line. Since the support part 50 and the surgical instrument 5 are parallel to the third link 13, the surgical instrument 5 can make translational motions along a straight line passing through the RCM, regardless of attitudes of the arm part 10.

At this time, in the case in which two rhombus structures contract in the direction of the diagonal line, the third link 13 held by the guide pin 43 abuts on an upper surface of the linear bushing 42. Accordingly, a maximum contraction width of the rhombus structures is regulated, and a maximum downward movement amount of the surgical instrument 5 is regulated. In addition, a maximum extension width of the rhombus structures can be set in a revolution range of the eighth link 17b and the sixth link 15c. Therefore, a length of the guide pin 43 and an abutting position of the third link 13 and the linear bushing 42 are decided in accordance with a range of translational motions of the surgical instrument 5.

As described above, by the first motor 30a and the third motor 30b being driven to cause the two rhombus structures having the third link 13 and its extended line as the diagonal line to extend and contract in the direction of the diagonal line, the surgical instrument 5 can move forward and backward to pass through the RCM. Note that, when the surgical instrument 5 only makes translational motions, the parallel links of the arm part 10 are deformed along the specific link configuration plane while being presenting within the link configuration plane.

Returning to FIG. 2 and FIG. 3, the seventh link (the second drive link) 17a is connected to the second drive shaft 31c via a second orthogonal joint part 40c. The second orthogonal joint part 40c includes an L-shaped member 45 and the joint part 60n. One piece of the L-shaped member 45 is connected to the second drive shaft 31c and extends in a direction orthogonal to the axis of the second drive shaft 31c. In addition, the other piece of the L-shaped member 45 extends in the direction of the axis of the second drive shaft 31c and is revolvably connected to the seventh link 17a by the joint part 60n. Note that the seventh link 17a is not connected to the third drive shaft 31b.

A revolution range of the L-shaped member 45 of the second orthogonal joint part 40c in accordance with rotation of the second drive shaft 31c is regulated by stoppers 28c and 28d. In other words, the L-shaped member 45 revolves from a position at which the member abuts on the stopper 28c and a position at which the member abuts on the stopper 28d.

In FIG. 8, a rotation axis Ax_m2 of the second drive shaft 31c in the second orthogonal joint part 40c and a rotation axis Ax_j3 of the joint part 60n connecting the L-shaped member 45 and the seventh link 17a are indicated by thick lines. The two axes Ax_m2 and Ax_j3 for the rotation axis of the second drive shaft 31c and the joint part 60n are orthogonal to each other and intersect at one point. Thus, when the second motor 30c is driven, the second drive shaft 31c performs shaft rotation and the seventh link 17a revolves around the axis Ax_m2 of the second drive shaft 31c in the left-right direction, regardless of attitudes of the arm part 10.

Returning to FIG. 2 and FIG. 3, the eighth link 17b and the sixth link 15c each are connected to the first drive shaft 31a and the third drive shaft 31b via the first orthogonal joint part 40a and the third orthogonal joint part 40b in which three the rotation axes are orthogonal. Thus, the eighth link 17b and the sixth link 15c are revolvable even in the left-right direction, and the arm part 10 also entirely revolves in the left-right direction in accordance with revolution of the seventh link 17a. The three rotation axes of each of the first orthogonal joint part 40a and the third orthogonal joint part 40b are intersect on the axis of the second drive shaft 31c. Thus, the surgical instrument 5 or the axis of the surgical instrument 5 passes through the RCM at all times regardless of inclinations of the arm part 10 in the left-right direction.

As described above, when the second motor 30c is driven, the entire arm part 10 inclines in the left-right direction, and thus the surgical instrument 5 can revolve in the left-right direction with respect to the RCM. Note that, when the surgical instrument 5 revolves in the left-right direction, the arm part 10 inclines in the left-right direction as a whole, and the plurality of parallel links of the arm part 10 are maintained within the common link configuration plane.

Here, focusing on the first drive shaft 31a and the second drive shaft 31c, the first drive shaft 31a and the second drive shaft 31c have a closed link structure constituting seven degrees of freedom. In addition, orthogonal three degrees of freedom and orthogonal two degrees of freedom are each configured immediately after the first drive shaft 31a and the second drive shaft 31c. Thus, rotation of each other is not obstructed. In addition, the third drive shaft 31b and the second drive shaft 31c are also in a similar relationship.

In addition, self-weight compensating springs 51a, 51b, 51c, and 51d are each wound around the first drive shaft 31a, the third drive shaft 31b, and the second drive shaft 31c, and one end of each of the springs is engaged with projection parts 29a, 29b, 29c, and 29d. Accordingly, reaction forces are applied against shaft rotation of the first drive shaft 31a, the third drive shaft 31b and the second drive shaft 31c, which assists self-standing of the arm part 10. Therefore, the arm part 10 is prevented from inclining in a specific direction due to the arm part 10's own weight.

<1-3. Attitude of Arm Part>

The configuration of the support arm device 1 according to the present embodiment has been described above. Next, various attitudes that the arm part 10 of the support arm device 1 can take will be described. Rotational motions of the arm part 10 in the front-rear direction and translational motions thereof in the top-bottom direction controlled mainly by the first motor 30a and the third motor 30b, and rotational motions of the arm part 10 in the left-right direction controlled mainly by the second motor 30c will be described below.

(1-3-1. Operation in Front-Rear Direction and Top-Bottom Direction)

Figure 10:
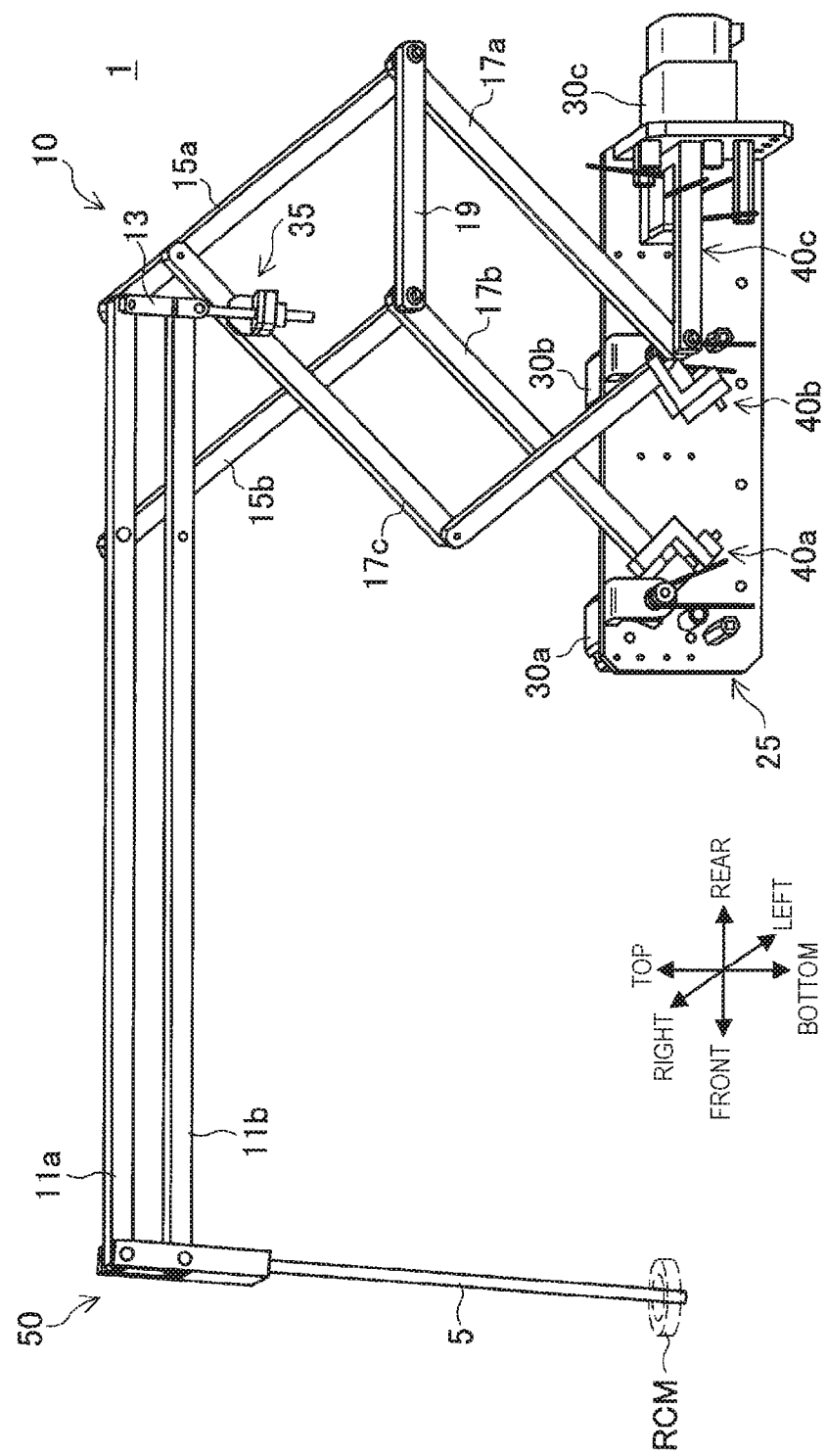
FIG. 10 is a diagram showing a basic attitude of the arm part.

FIG. 10 to FIG. 16 each show examples of attitudes of the arm part 10 moving in the front-rear direction and the top-bottom direction, and FIG. 11 to FIG. 16 show virtual lines indicating the attitude (a basic attitude) of the arm part 10 of FIG. 10 in order to facilitate comparison to the attitude of the arm part 10 of FIG. 10.

In FIG. 10, the arm part 10 is not inclined in the left-right direction, the arm part 10 and the surgical instrument 5 are supported substantially in the vertical direction, and a tip part of the surgical instrument 5 slightly enters the RCM.

Figure 11:
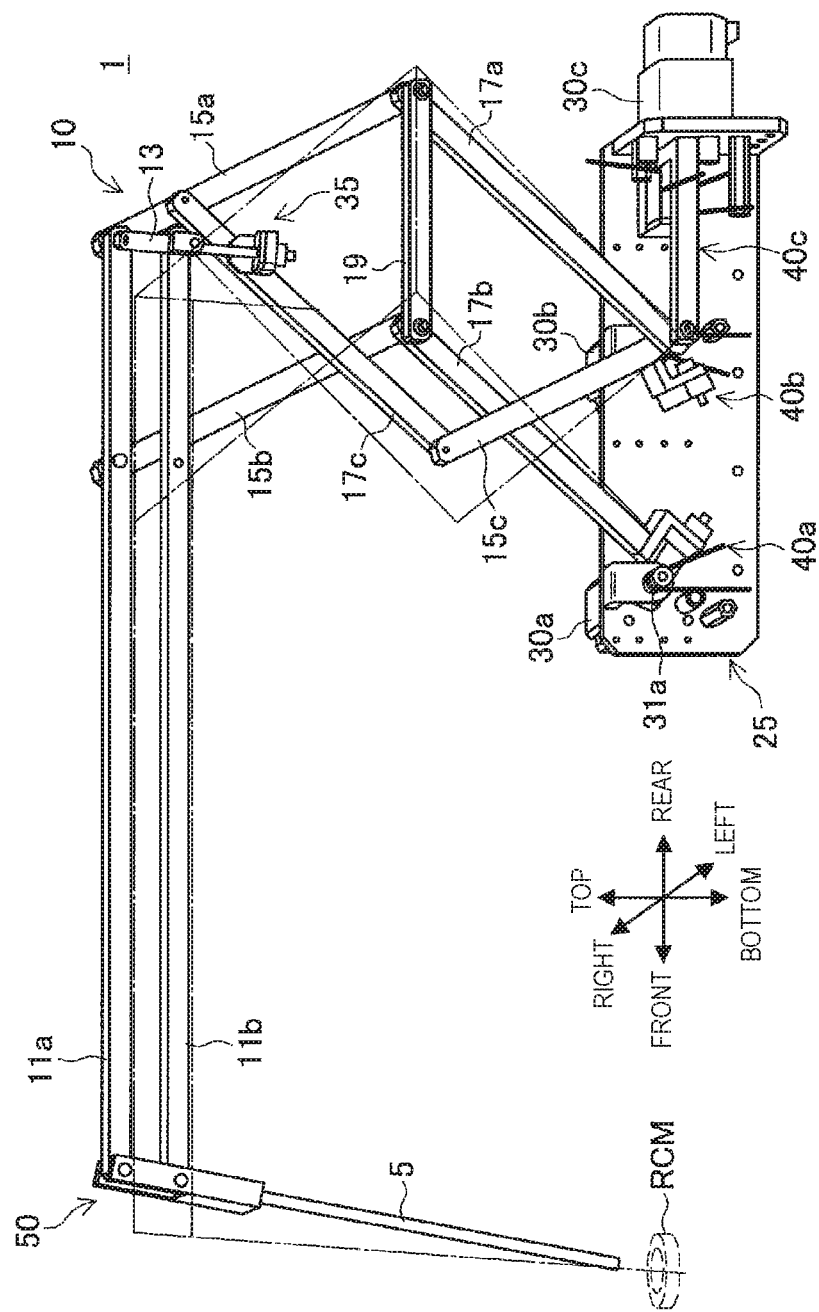
FIG. 11 is a diagram for describing change of an attitude of the arm part.

FIG. 11 shows an attitude of the arm part 10 in a case in which the first drive shaft 31a and the third drive shaft 31b are rotated in the reverse direction from the state of FIG. 10. In this case, the first drive shaft 31a rotates in the counterclockwise direction of the drawing, the third drive shaft 31b rotates in the clockwise direction, and the rotation amount (a rotation angle) of the third drive shaft 31b is greater than the rotation amount (a rotation angle) of the first drive shaft 31a. Accordingly, the angle formed by the seventh link 17a and the sixth link 15c becomes smaller, the two rhombus structures having the third link 13 and the extended line thereof as a diagonal line extend along the diagonal line. As a result, the surgical instrument 5 ascends while inclining backward with respect to the RCM, and the tip part thereof gets out of the RCM.

Figure 12:
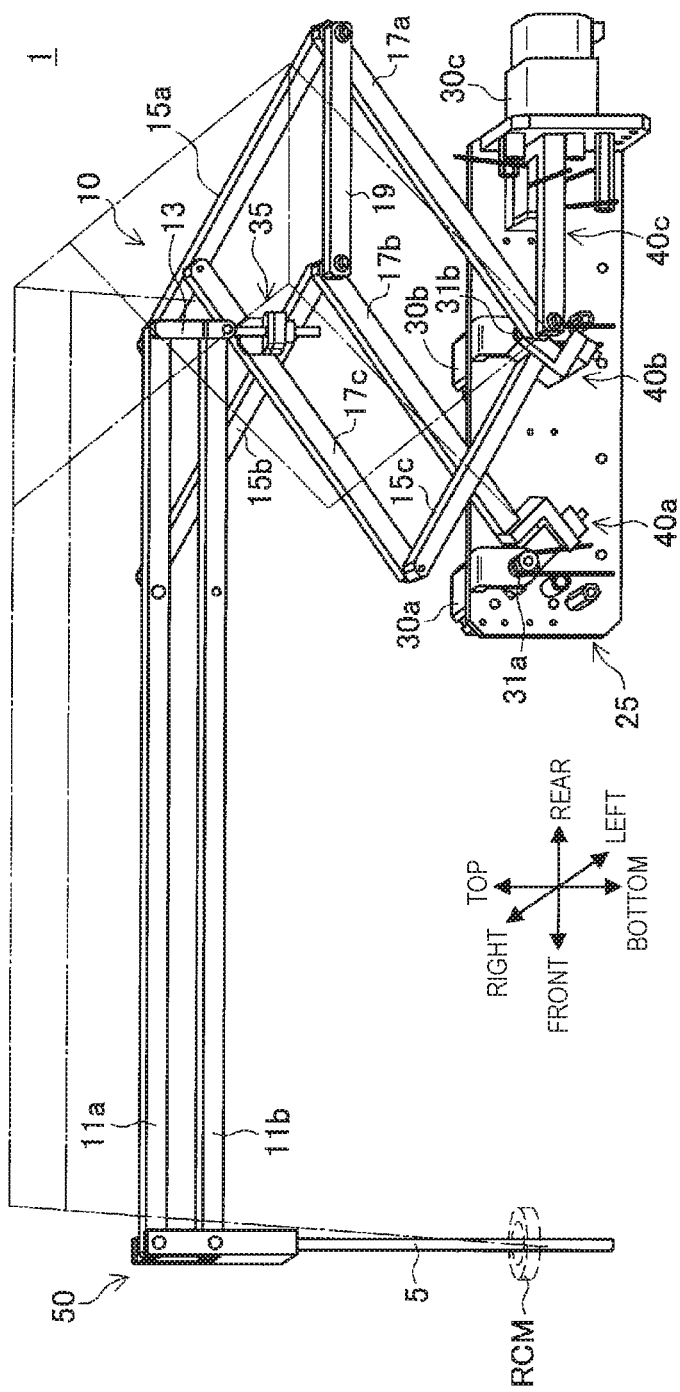
FIG. 12 is a diagram for describing change of an attitude of the arm part.

FIG. 12 shows an attitude of the arm part 10 in a case in which the first drive shaft 31a and the third drive shaft 31b are rotated in the reverse direction from the state of FIG. 10. In this case, the first drive shaft 31a rotates in the counterclockwise direction of the drawing, the third drive shaft 31b rotates in the counterclockwise direction, and the rotation amount of the third drive shaft 31b is greater than the rotation amount of the first drive shaft 31a. Accordingly, the angle formed by the seventh link 17a and the sixth link 15c becomes larger, the two rhombus structures having the third link 13 and the extended line thereof as a diagonal line contract along the diagonal line. As a result, the surgical instrument 5 descends while revolving forward with respect to the RCM, and the tip part thereof enters the RCM to a lower side.

Figure 13:
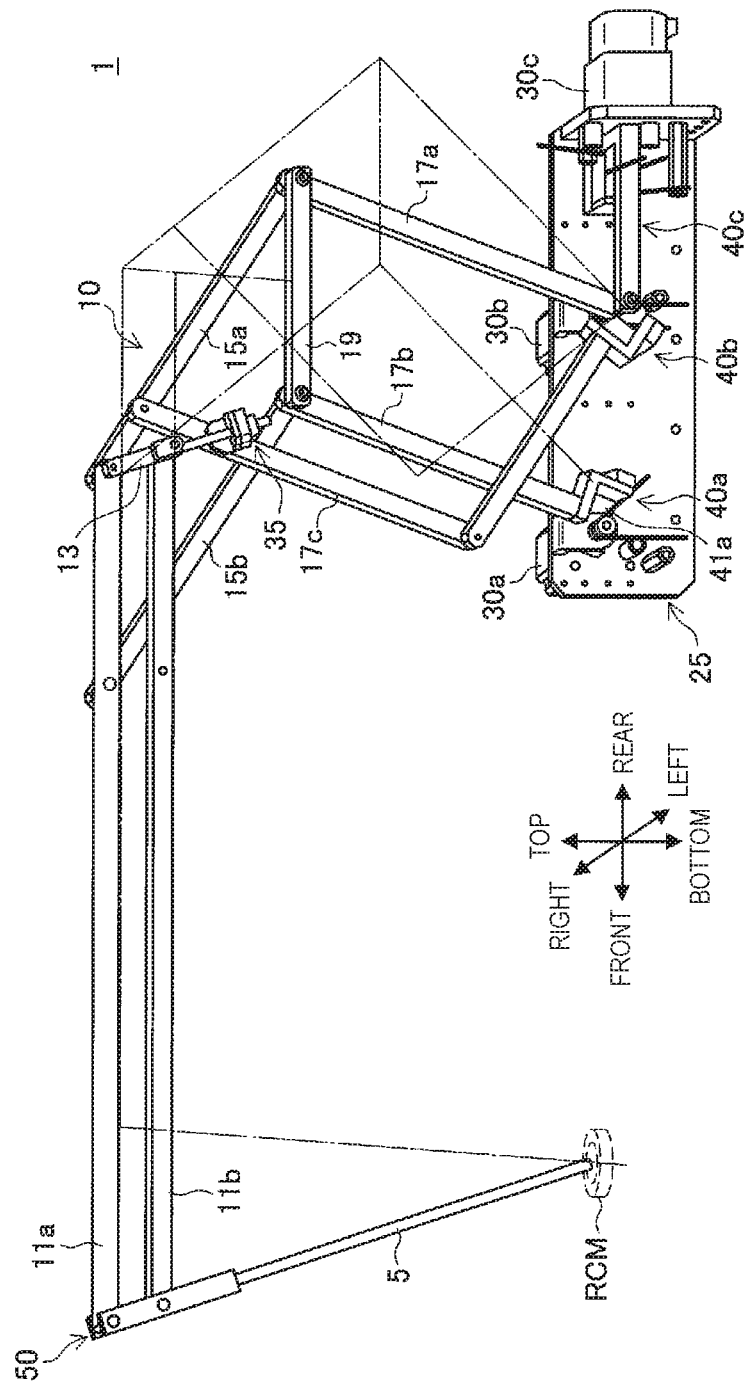
FIG. 13 is a diagram for describing change of an attitude of the arm part.

FIG. 13 shows an attitude of the arm part 10 in a case in which the first drive shaft 31a and the third drive shaft 31b are rotates in the same direction from the state of FIG. 10. In this case, the first drive shaft 31a and the third drive shaft 31b rotate in the counterclockwise direction of the drawing in substantially the same rotation amount. Accordingly, the arm part 10 rotates while maintaining the shapes of the two rhombus structures having the third link 13 and its extending property as a diagonal line. As a result, the surgical instrument 5 revolves forward with respect to the RCM while maintaining substantially its height.

Figure 14:
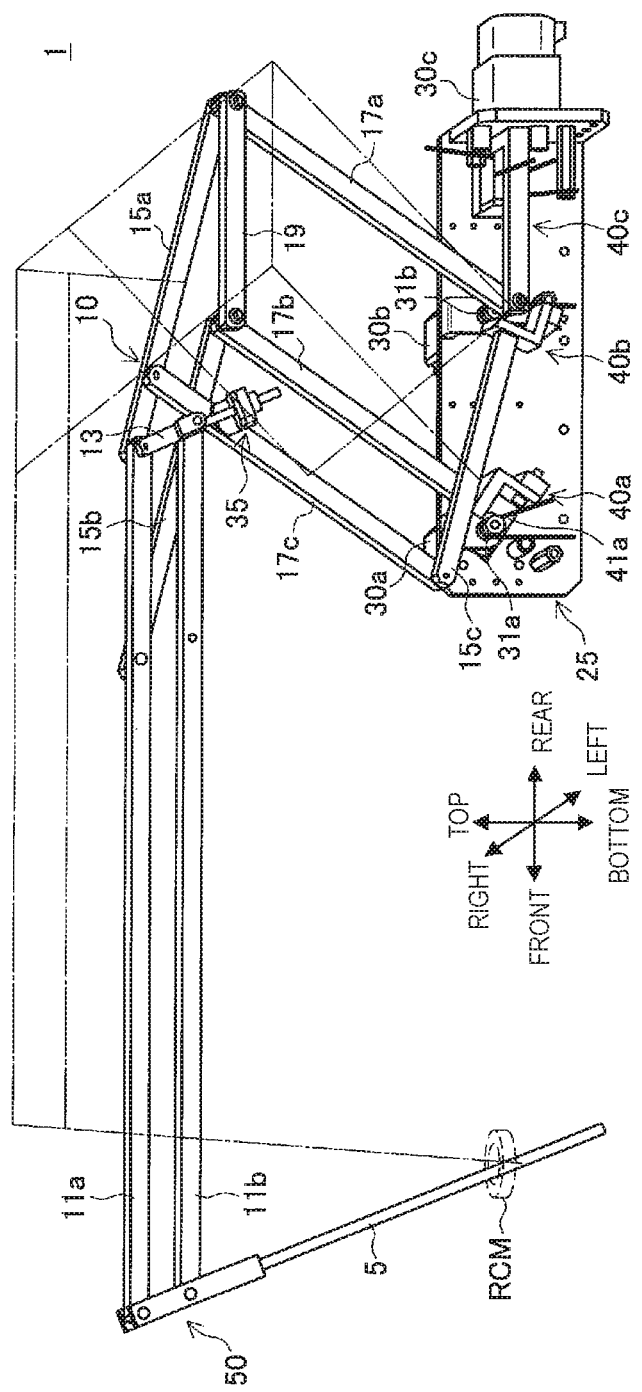
FIG. 14 is a diagram for describing change of an attitude of the arm part.

FIG. 14 shows an attitude of the arm part 10 in a case in which the first drive shaft 31a and the third drive shaft 31b are rotated in the same direction from the state of FIG. 10. FIG. 14 corresponds to an attitude of the arm part 10 in a case in which only the third drive shaft 31b is further rotated in the counterclockwise direction of the drawing from the state of FIG. 13. In this case, the angle formed by the seventh link 17a and the sixth link 15c become larger, and the two rhombus structures having the third link 13 and the extended line as a diagonal line contract along the diagonal line. As a result, the surgical instrument 5 descends while inclining forward with respect to the RCM, and the tip portion thereof enters the RCM to a lower side.

Note that FIG. 13 and FIG. 14 show a state in which the L-shaped member 41a constituting the first orthogonal joint part 40a abuts on the stopper 28b (refer to FIG. 3). That is, FIG. 13 and FIG. 14 show a state in which the surgical instrument 5 is inclined to a foremost side.

Figure 15:
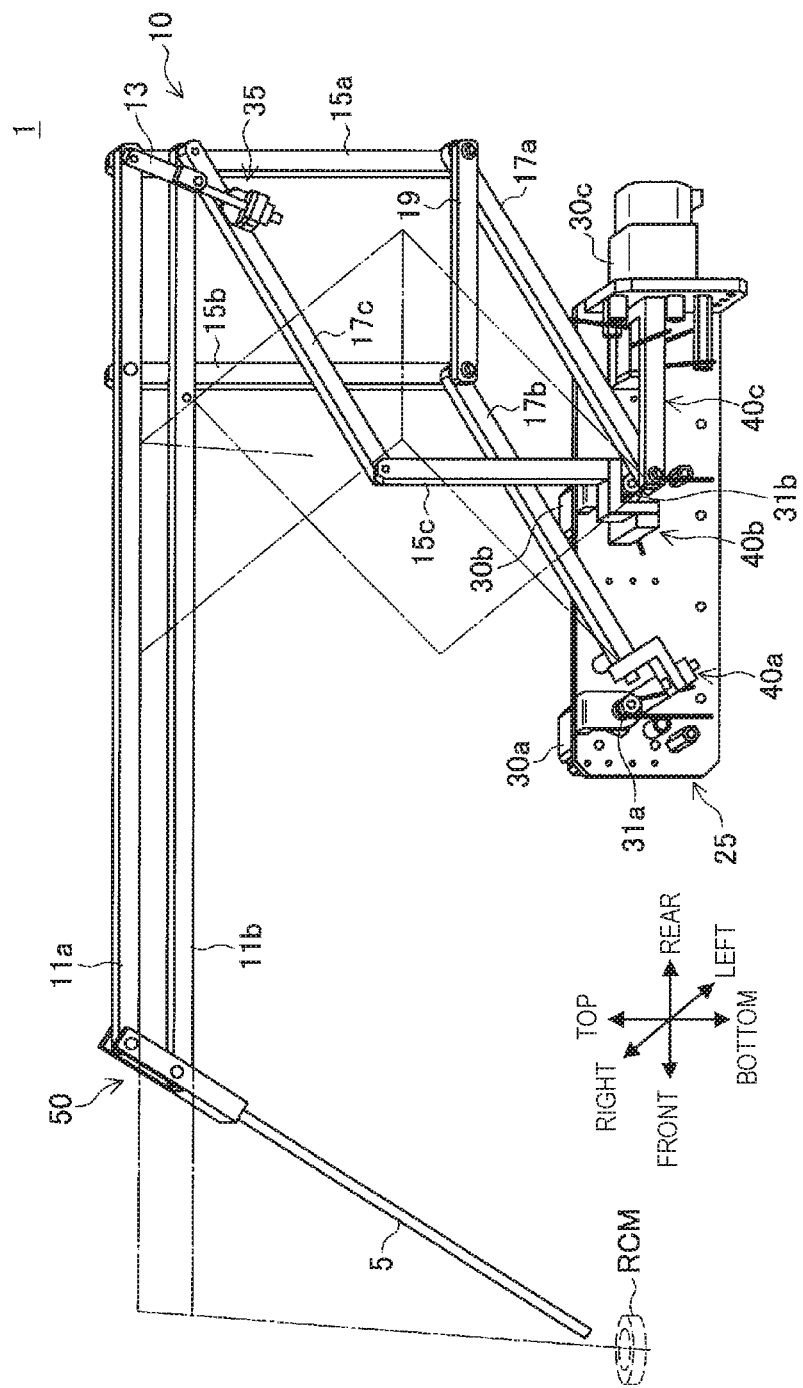
FIG. 15 is a diagram for describing change of an attitude of the arm part.

FIG. 15 shows an attitude of the arm part 10 in a case in which the first drive shaft 31a and the third drive shaft 31b are rotated in the same direction from the state of FIG. 10. In this case, the first drive shaft 31a and the third drive shaft 31b rotate in clockwise direction of the drawing together, and the rotation amount of the third drive shaft 31b is greater than the rotation amount of the first drive shaft 31a. Accordingly, the angle formed by the seventh link 17a and the sixth link 15c becomes smaller, and the two rhombus structures having the third link 13 and the extended line as a diagonal line extend along the diagonal line. As a result, the surgical instrument 5 ascends while inclining backward with respect to the RCM, and the tip part thereof gets out from the RCM.

Figure 16:
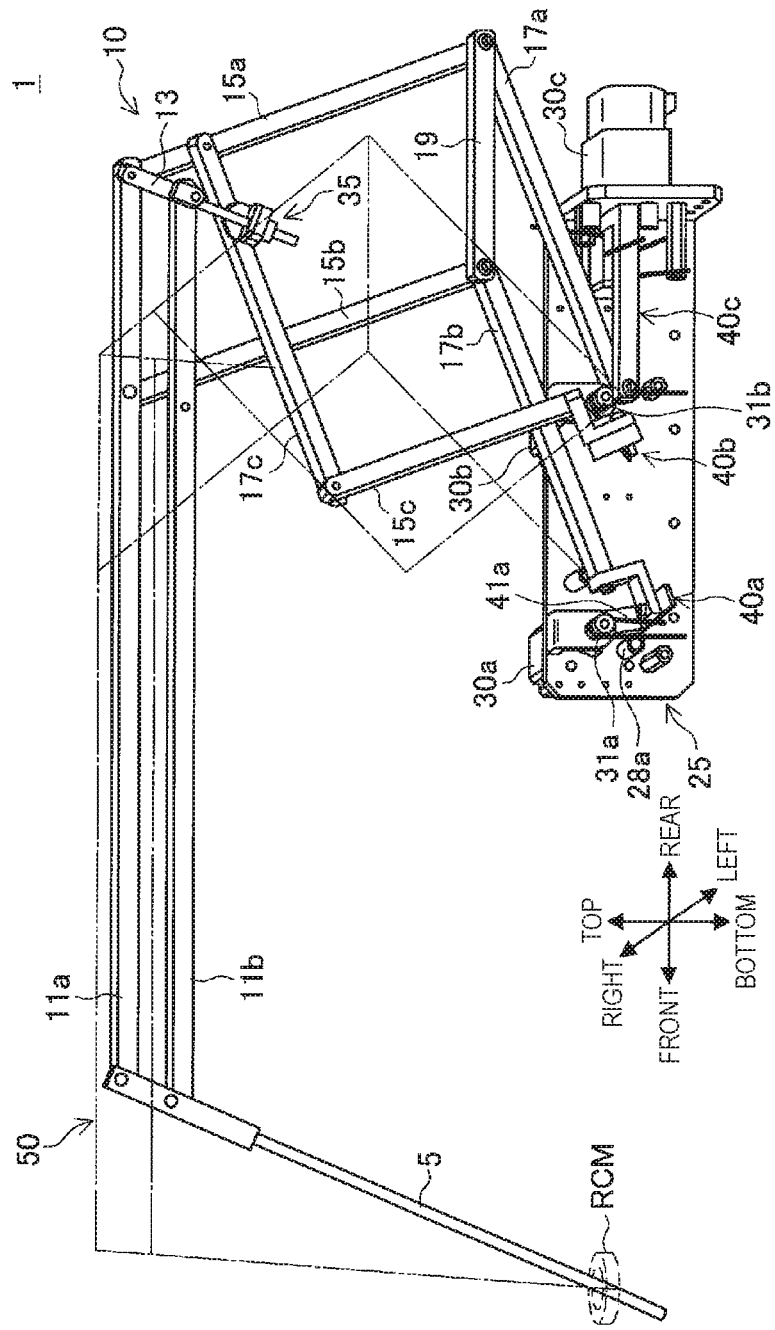
FIG. 16 is a diagram for describing change of an attitude of the arm part.

FIG. 16 shows an attitude of the arm part 10 in a case in which the first drive shaft 31a and the third drive shaft 31b are rotated in the same direction from the state of FIG. 10. FIG. 16 corresponds to an attitude of the arm part 10 in a case in which the first drive shaft 31a further rotates in the clockwise direction of the drawing from the state of FIG. 15 and the third drive shaft 31b returns in the counterclockwise direction of the drawing. In this case, the angle formed by the seventh link 17a and the sixth link 15c becomes larger than the state of FIG. 15, and the two rhombus structures having the third link 13 and the extended line as a diagonal line contract along the diagonal line. As a result, the surgical instrument 5 descends while revolving forward with respect to the RCM and the tip part thereof enters the RCM.

Note that FIG. 16 shows a state in which the L-shaped member 41a constituting the first orthogonal joint part 40a abuts on the stopper 28a (refer to FIG. 3). That is, FIG. 16 shows a state in which the surgical instrument 5 is inclined to a rearmost side.

(1-3-2. Operation in Left-Right Direction)

Figure 17:
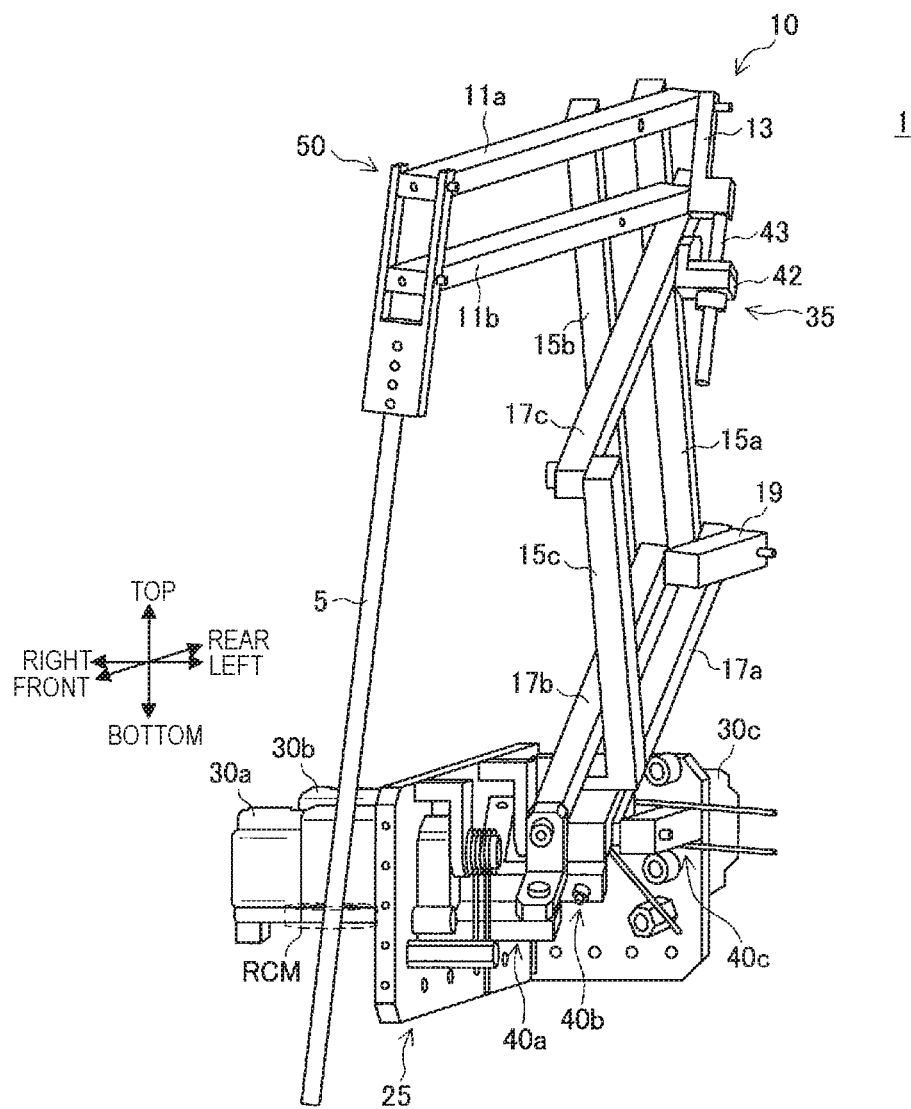
FIG. 17 is a diagram for describing change of an attitude of the arm part.
Figure 18:
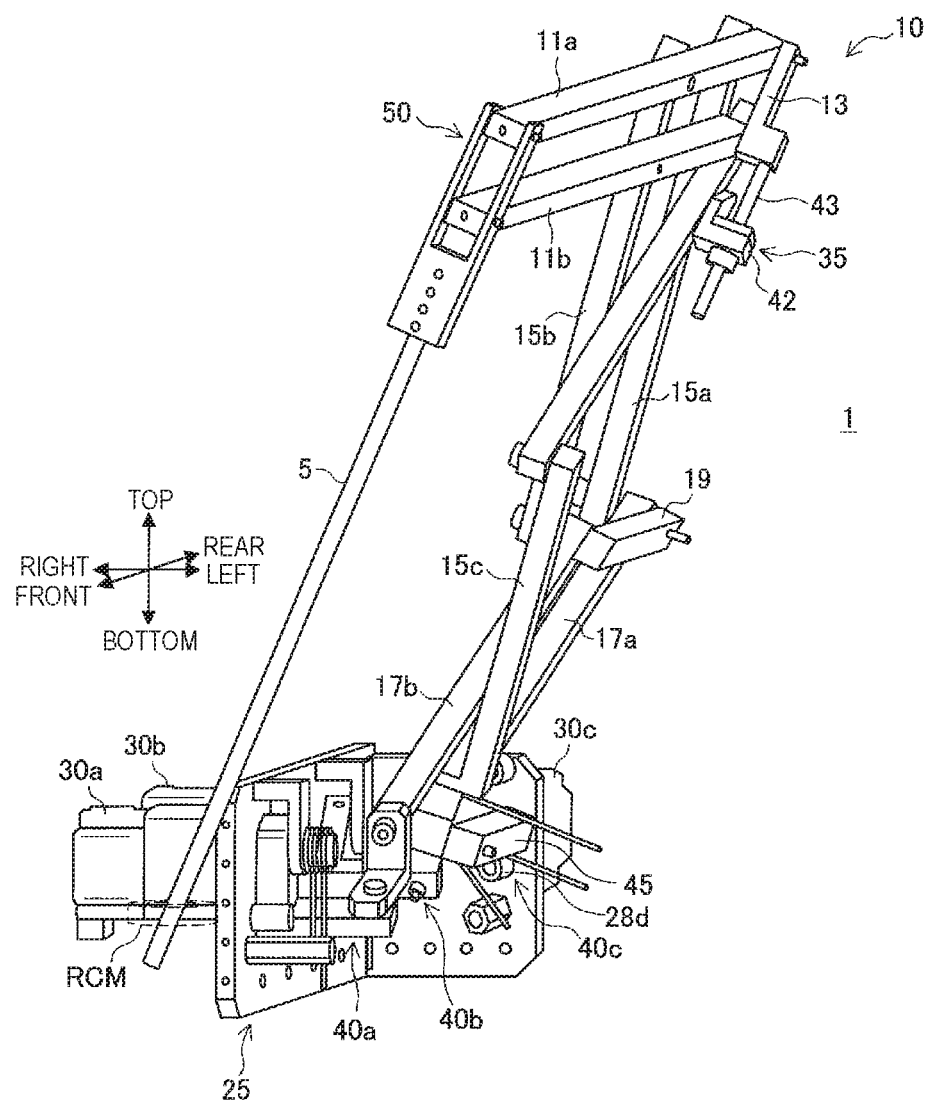
FIG. 18 is a diagram for describing change of an attitude of the arm part.
Figure 19:
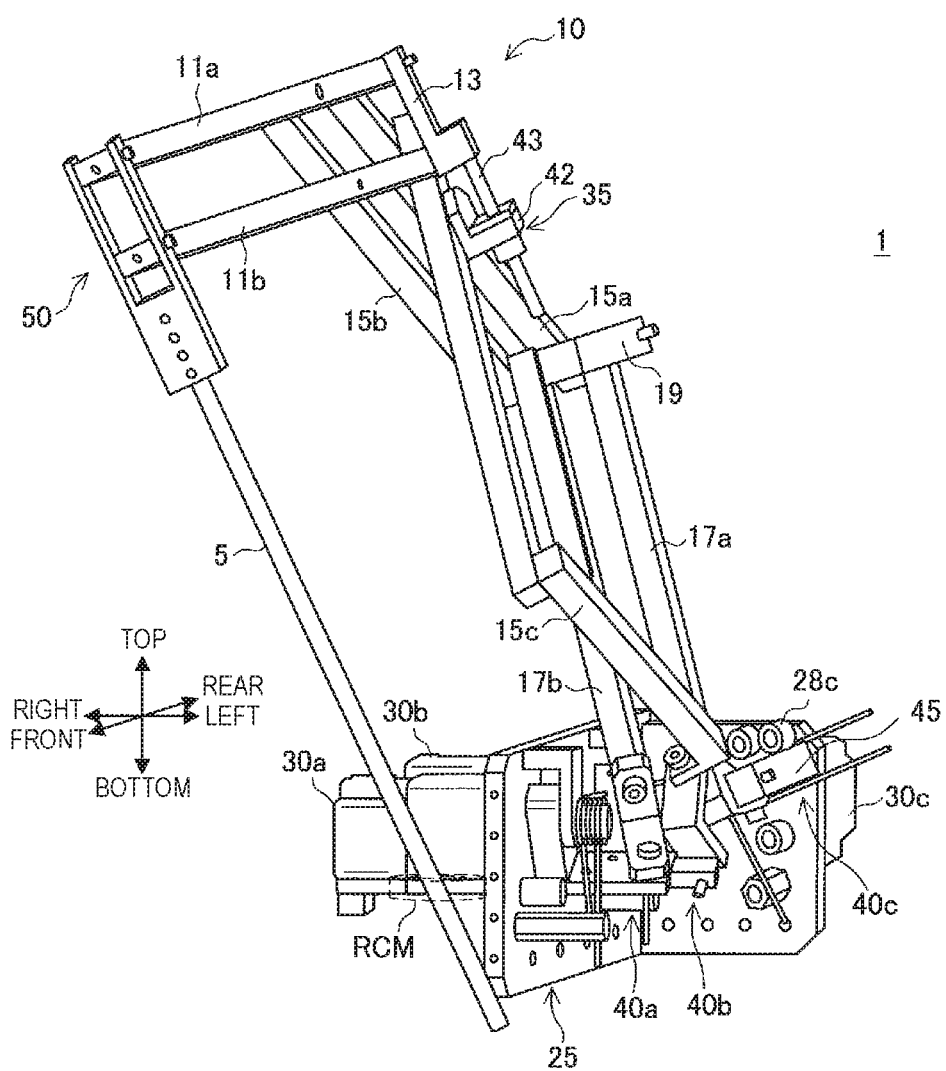
FIG. 19 is a diagram for describing change of an attitude of the arm part.

FIG. 17 to FIG. 19 each show examples of attitudes of the arm part 10 moving in the left-right direction. In FIG. 17 to FIG. 19, the arm part 10 changes its attitude in accordance with shaft rotation of the second drive shaft 31c caused by the second motor 30c being driven in a constant drive state of the first motor 30a and the third motor 30b.

FIG. 17 shows the arm part 10 held in a state in which an inclination thereof in the left-right direction is zero. In this state, an inclination of the surgical instrument 5 supported by the support part 50 of the arm part 10 in the left-right direction is in a zero state. FIG. 18 shows a state in which the second drive shaft 31c is rotated in the clockwise direction of the drawing and thus the arm part 10 is inclined to the left (to the right side of the drawing). Accordingly, the surgical instrument 5 supported by the support part 50 of the arm part 10 is also inclined to the left. In addition, FIG. 19 shows a state in which the second drive shaft 31c is rotated in the counterclockwise direction of the drawing and thus the arm part 10 is inclined to the right (to the left side of the drawing). Accordingly, the surgical instrument 5 supported by the support part 50 of the arm part 10 is also inclined to the right.

Even in a case in which the second drive shaft 31c is rotated to any of the left and right directions, the seventh link 17a, which is revolvably connected to the L-shaped member 45 fixed to the second drive shaft 31c, is inclined, and accordingly, the arm part 10 is entirely inclined to the left or right. At this time, the first orthogonal joint part 40a and the third orthogonal joint part 40b connecting the arm part 10 and the first drive shaft 31a and the third drive shaft 31b constitute three degrees of freedom, and the second orthogonal joint part 40c connecting the arm part 10 and the second drive shaft 31c constitute two degrees of freedom. Thus, the arm part 10 can revolve in the left-right direction without interference of the plurality of links with each other. In addition, since the RCM is positioned on the axis of the second drive shaft 31c, even in a case in which the arm part 10 revolves in the left-right direction, the position of the RCM does not shift.

Even in a case in which the arm part 10 revolves in the front-rear direction by the first motor 30a and the third motor 30b and moves forward and backward in the top-bottom direction, revolution of the arm part 10 in the left-right direction by the second motor 30c is realized without interrupting in rotation of the aforementioned case. Therefore, the support arm device 1 according to the present embodiment can realize a parallel mechanism constituting three degrees of freedom in which the surgical instrument 5 can make translational motions in its extension direction with one degree of freedom and rotational motions in which the surgical instrument 5 is inclined to the front, rear, left and right. Therefore, the surgical instrument 5 can be inserted into a patient from various angles, and a degree of freedom in which the surgical instrument 5 is operated can be improved.

Note that FIG. 18 shows a state in which the L-shaped member 45 constituting the second orthogonal joint part 40c abuts on the stopper 28d. That is, FIG. 18 shows a state in which the surgical instrument 5 is inclined to a leftmost side. In addition, FIG. 19 shows a state in which the L-shaped member 45 constituting the second orthogonal joint part 40c abuts on the stopper 28c. That is, FIG. 19 shows a state in which the surgical instrument 5 is inclined to a rightmost side.

As already described, a range in which the surgical instrument 5 can be inclined in the front-rear direction is limited by the stoppers 28a and 28b regulating a revolution range of the L-shaped member 41a of the first orthogonal joint part 40a. In addition, a range in which the surgical instrument 5 can be inclined in the left-right direction is limited by the stoppers 28c and 28d regulating a revolution range of the L-shaped member 45 of the second orthogonal joint part 40c. In the support arm device 1, the surgical instrument 5 may be inclined, for example, 25° at a maximum in the 360° direction of a predetermined rotation axis.

In addition, a range in which the surgical instrument 5 can move forward and backward in the extension direction of the surgical instrument 5 can be adjusted by a revolution range of the third drive shaft 31b. In the support arm device 1, the surgical instrument 5 may be set to move forward and backward in the extension direction of the surgical instrument 5, for example, within a range from 100 mm to 200 mm at a maximum. Note that a maximum advance amount of the surgical instrument 5 is regulated during an operation or the like by causing the third link 13 to abut on the linear bushing 42 so that, when the arm part 10 is unexpectedly incapable of standing by itself, the surgical instrument 5 is prevented from entering the inside of a body.

As described above, the support arm device 1 according to the present embodiment has a relatively simple structure including the plurality of links connected to each other and the three motors, and thus manufacturing costs can be reduced. In addition, since the arm part 10 constituted by the plurality of links is present within the link configuration plane as a whole, the support arm device 1 according to the present embodiment has a small width in the left-right direction, and thus can occupy a reduced volume.

Furthermore, the support arm device 1 according to the present embodiment has a configuration in which the first motor 30a, the second motor 30c, and the third motor 30b that are fixed to the base part 21 do not move when the arm part 10 changes its attitude. Thus, weights of parts that are movable by each of the motors can be relatively light and output of the motors can be reduced. Accordingly, the motors can be miniaturized or an amount of power consumption can be reduced.

<1-4. Control Device>
(1-4-1. Basic Example)

Next, a configuration of a control device that controls attitudes of the support arm device 1 and controls positions and attitudes of the surgical instrument 5 supported by the support arm device 1 due to drive of the first motor 30a, the second motor 30c, and the third motor 30b of the support arm device 1 will be described.

Figure 20:
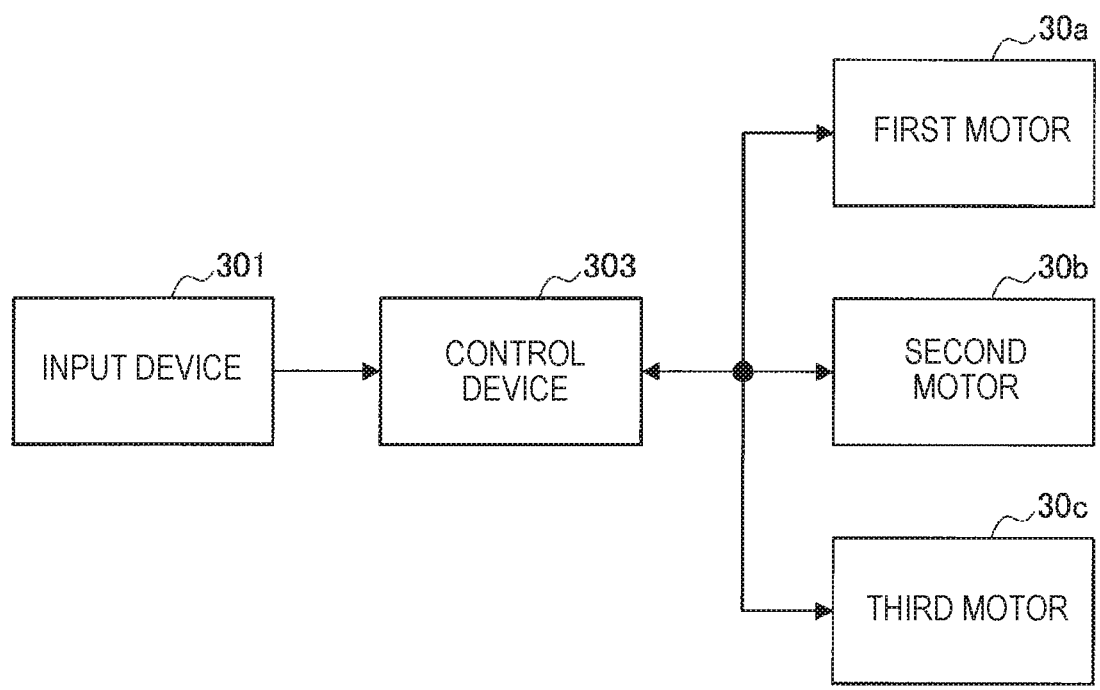
FIG. 20 is a block diagram for describing a control part of the support arm device.

FIG. 20 is a block diagram showing a functional configuration relating to control of the support arm device 1. The support arm device 1 includes an input device 301 and a control device 303. The control device 303 receives operation input transmitted from the input device 301, calculates control amounts of the first motor 30a, the second motor 30c, and the third motor 30b, and outputs control commands to each of the motors.

The input device 301 is provided at, for example, a position away from the support arm device 1, with which an operator or an assistant inputs an instruction regarding an operation of the arm part 10. The input device 301 may include, for example, operation buttons for instructing movements to a front, rear, left, and right sides and operation buttons for instructing movement upward and downward. Alternatively, the input device 301 may be a device in which a device that can instruct inclinations in 360° directions, like a joystick, with an input device that instructs upward and downward movements. Furthermore, the input device 301 may be an input device such as a touch panel.

In addition, the input device 301 may be integrated with an operation unit for operating the surgical instrument 5 such as an endoscope or an end-effector supported by the support part 50 of the arm part 10. If the input device 301 for operating the arm part 10 is integrated with the operation unit for the surgical instrument 5, an operator can change a position or an angle of the surgical instrument 5 while operating the surgical instrument 5 by himself or herself even in a case in which there is no assistant. Note that communication between the input device 301 and the control device 303 can be performed using any of various know wired or wireless methods.

The control device 303 controls positions of the tip of the surgical instrument 5 by controlling, for example, a rotation amount (a rotation angle) of each motor. The control device 303 may be a processor, for example, a central processing unit (CPU), a digital signal processor (DSP), or the like. Alternatively, the control device 303 may be a control board or a microcomputer on which memory elements such as the processors and memories are mounted. When the processors included in the control device 303 execute various kinds of signal processing in accordance with a predetermined program, the surgical instrument 5 supported by the arm part 10 execute pivotal motions and translational motions. Specifically, the first motor 30a, the second motor 30c, and the third motor 30b are driven under control of the control device 303.

A method for obtaining a position of the tip of the surgical instrument 5 in a case in which an output shaft of the first motor 30a is the first drive shaft 31a, an output shaft of the second motor 30c is the second drive shaft 31c, and an output shaft of the third motor 30b is the third drive shaft 31b will be described below with reference to FIG. 21 to FIG. 23.

Note that, in the following description, the support arm device 1 is assumed to be placed such that a plane including the first drive shaft 31a, the second drive shaft 31c, and the third drive shaft 31b is parallel to a horizontal plane. In addition, the link configuration plane in which the arm part 10 is present will be described as an x-z plane. That is, an inclination of the x-z plane with respect to the left-right direction can be changed in accordance with shaft rotation of the second drive shaft 31c.

(1-4-1-1. Control Using Forward Kinematics)

First, a method for obtaining a position and an angle of the tip of the surgical instrument 5 using rotation angles of the first motor 30a, the second motor 30c, and the third motor 30b will be described.

A rotation angle of the first motor 30a is set to θa and a rotation angle of the third motor 30b is set to θb, and a length of the seventh link 17a and a length of the eighth link 17b each is set to La and a length of the fourth link 15a is set to Lb when the direction of the axis of the second drive shaft 31c is set to 0°. Since each of the links is configured to form parallelograms, angles between the links are as shown in FIG. 21. That is, an angle of the seventh link 17a and the eighth link 17b formed with respect to the axis of the second drive shaft 31c is θa, and an angle of the sixth link 15c formed with respect to the axis of the second drive shaft 31c and an angle formed by the fourth link 15a and the tenth link 19 are each θb.

Figure 22:
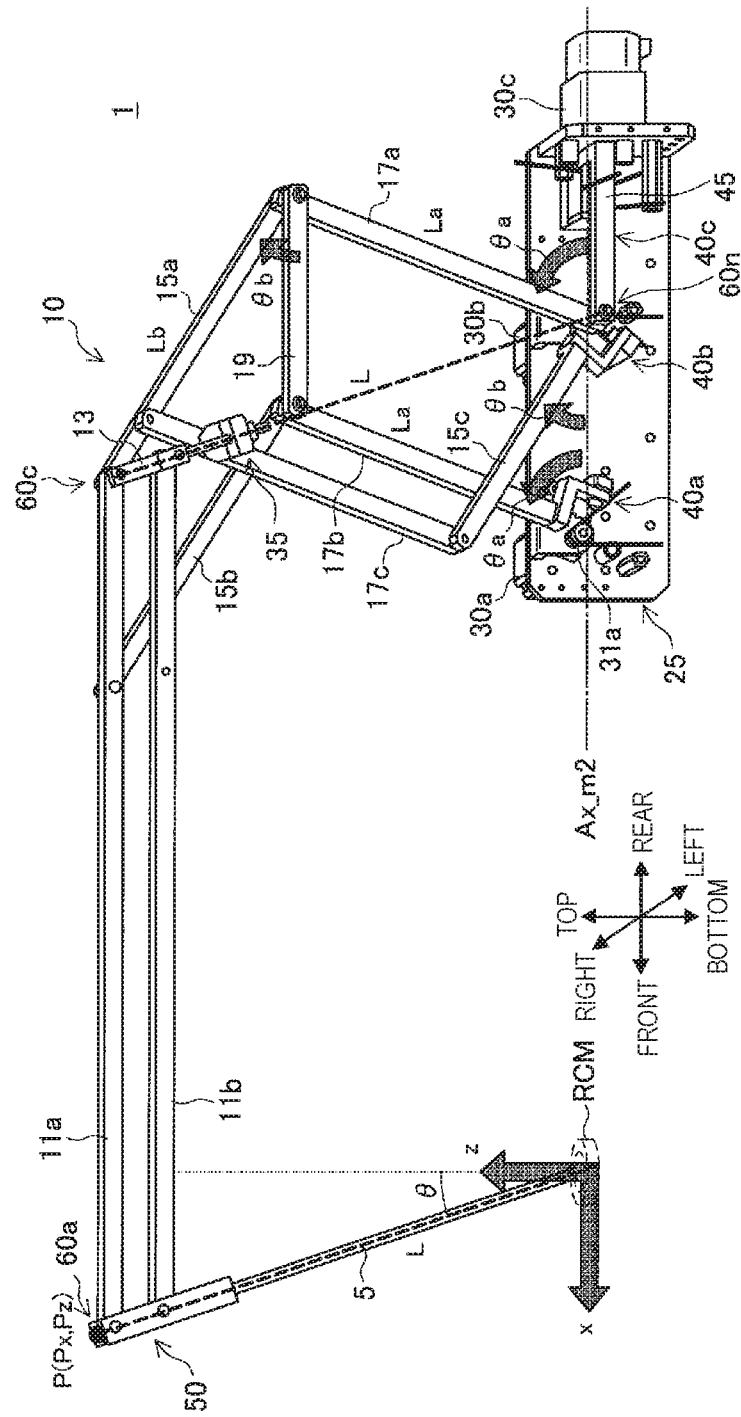
FIG. 22 is a diagram for describing a control method of the support arm device.
Figure 23:
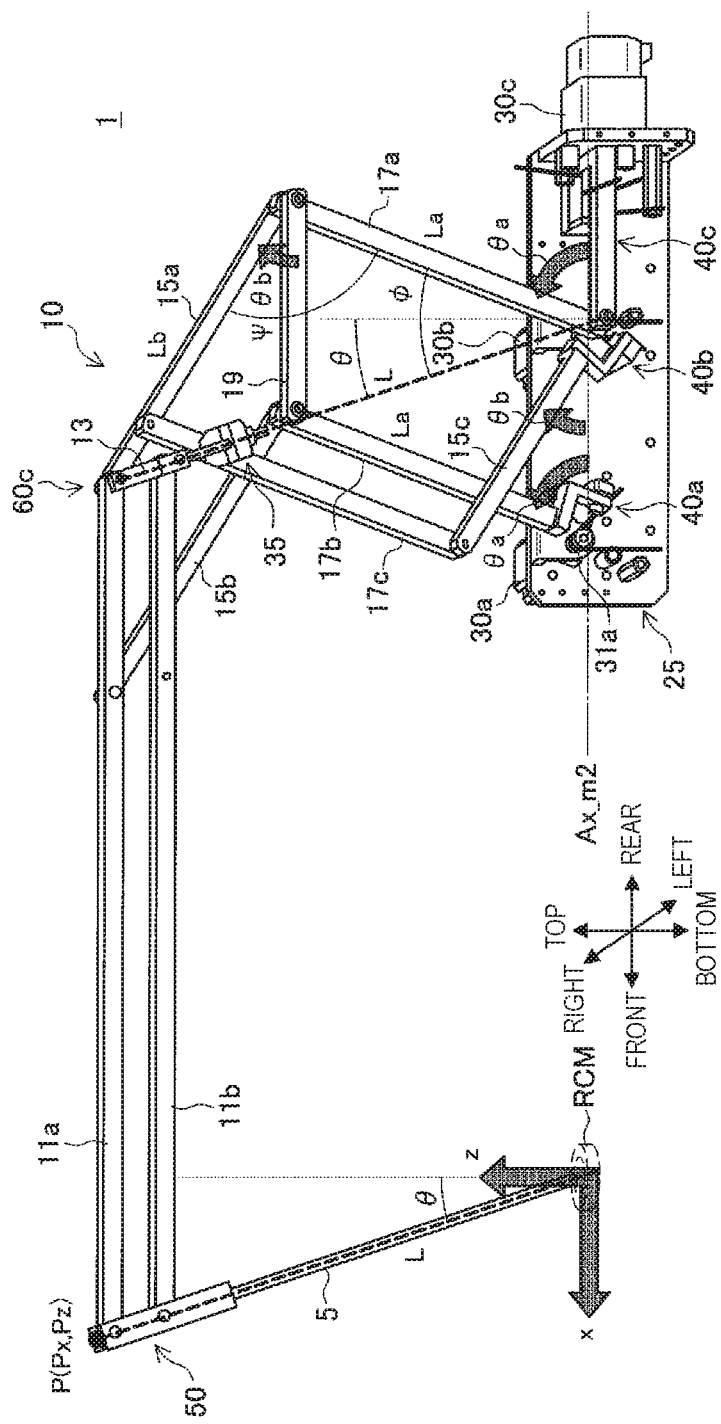
FIG. 23 is a diagram for describing a control method of the support arm device.

In addition, as shown in FIG. 22, a length of a straight line connecting the joint part 60c connecting the first link 11a, the third link 13, and the fourth link 15a and the joint part 60n connecting the L-shaped member 45 of the second orthogonal joint part 40c and the seventh link 17a is set to L. The first link 11a is parallel to the axis of the second drive shaft 31c, and the extension direction of the surgical instrument 5 is parallel to the straight line connecting the joint part 60c and the joint part 60n, and therefore it can be ascertained that a length of a straight line connecting the joint part 60a connecting the first link 11a and the support part 50 and the RCM is also L. Therefore, it can be ascertained that, by obtaining an inclination θ with respect to a z direction of the straight line having the length of L, an inclination θ of the tip of the surgical instrument 5 with respect to the z direction can be obtained.

Here, if the link configuration plane is set to x-z plane, origin coordinates (0,0) are placed on the center of the RCM, the front-rear direction is set on the x axis, and the top-bottom direction is set on the z axis, coordinates (Px, Pz) of a point P of the joint part 60a connecting the first link 11a and the support part 50 can be expressed using the following formula (1).

[Math. 1]

$$Px = Lb^*\cos(\theta b) - La^*\cos(\theta a)$$

$$Pz = Lb^*\sin(\theta b) + La^*\sin(\theta a) \quad (1)$$

In addition, the length L of the straight line and the inclination θ of the straight line with respect to the z direction within the link configuration plane (the x-z plane) can be expressed using the following formula (2).

[Math. 2]

$$L=\sqrt{(Px*Px+Pz*Pz)}=\sqrt{(La*La+Lb*Lb-2*La*Lb*\cos(\theta a+\theta b))}$$

$$\theta=\arctan(x/z) \quad (2)$$

Accordingly, on the basis of the rotation angles θa and θb of the first motor 30a and the third motor 30b, the distance L of the straight line from the position P of the joint part 60a to the RCM and the angle θ of the surgical instrument 5 with respect to the z direction are obtained. By inputting a distance from the position of the tip of the surgical instrument 5 to the position P of the joint part 60a with the surgical instrument 5 actually supported, a distance from the RCM to the tip of the surgical instrument 5 on the x-z plane can be obtained on the basis of the difference between the aforementioned distance and the distance L of the straight line.

In addition, an inclination of the link configuration plane (the x-z plane) in which the arm part 10 is present in the left-right direction is equal to a change amount of a rotation angle of the second motor 30c. Thus, an inclination of the surgical instrument 5 in the left-right direction can be obtained from the rotation angle of the second motor 30c.

As described above, the control device 303 can obtain a position and an angle of the tip of the surgical instrument 5 on the basis of a rotation angle of each of the first motor 30a, the second motor 30c, and the third motor 30b. Although a rotation angle of each motor can be detected using, for example, a potentiometer, a detection method other than that may be used. The control device 303 may cause the position and the angle of the tip of the surgical instrument 5 to be displayed on a monitor or the like. Accordingly, an operator can further operate the input device 301 to dispose the surgical instrument 5 at a desired position and angle on the basis of the position and the angle of the surgical instrument 5 displayed on the monitor or the like.

(1-4-1-2. Control Using Inverse Kinematics)

Next, a method for outputting instructions of rotation angles to the first motor 30a, the second motor 30c, and the third motor 30b in order to dispose the tip of the surgical instrument 5 at a desired position and angle.

Figure 21:
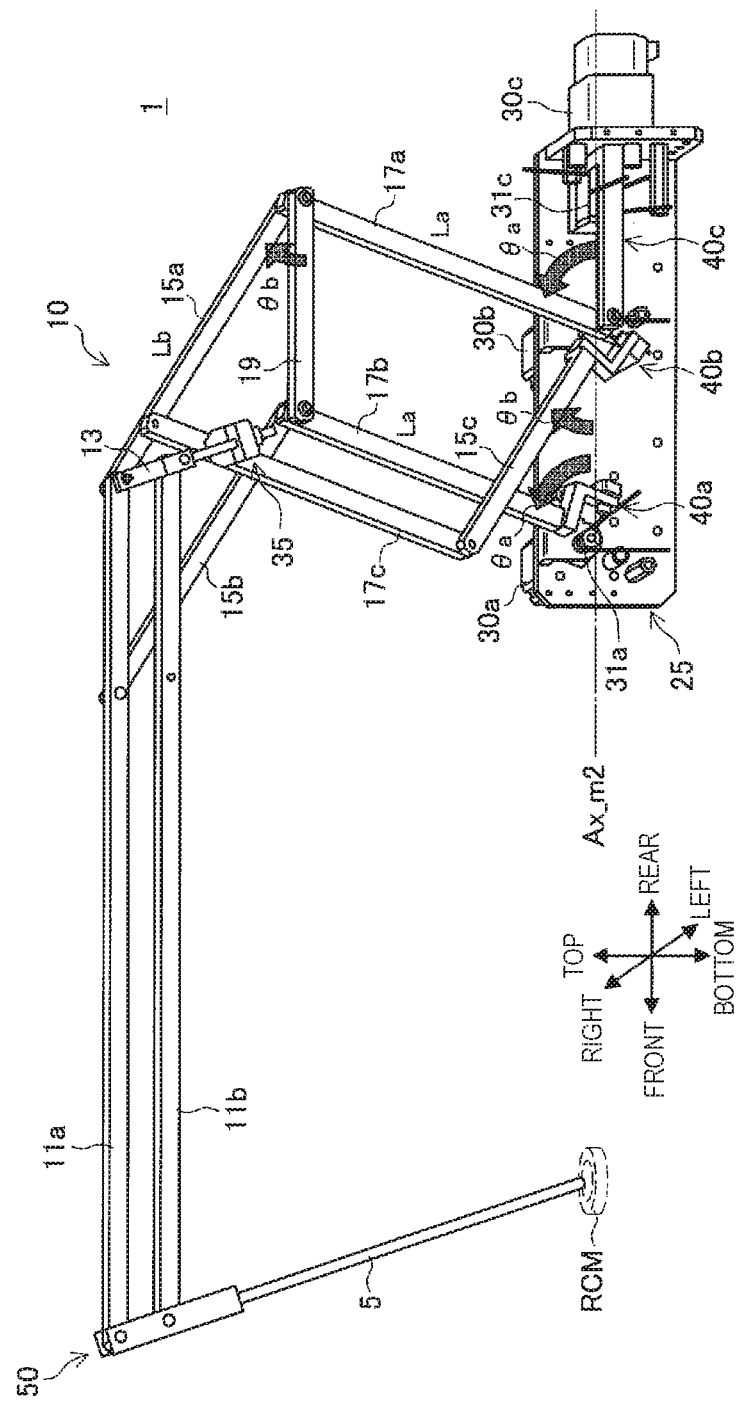
FIG. 21 is a diagram for describing a control method of the support arm device.

A rotation angle of the first motor 30a is set to θa, a rotation angle of the third motor 30b is set to θb, and a length of the seventh link 17a and a length of the eighth link 17b are each set to La, and a length of the fourth link 15a is set to Lb when the direction of the axis of the second drive shaft 31c is set to have angle of 0° as shown in FIG. 21. In addition, an angle formed by the straight line connecting the joint part 60c and the joint part 60n and the seventh link 17a is set to φ, and an angle formed by the seventh link 17a and the fourth link 15a is set to ψ as shown in FIG. 23.

The angles φ and θa can be expressed by the following formula (3) on the basis of a cosine theorem.

[Math. 3]

$$\varphi=\arccos((La*La+L*L-Lb*Lb)/(2*La*L))$$

$$\theta a=90°-(\varphi-\theta) \quad (3)$$

Likewise, the angles ψ and θ can be expressed by the following formula (4) on the basis of a cosine theorem.

[Math. 4]

$$\varphi=\arccos((La*La+Lb*Lb-L*L)/(2*La*Lb))$$

$$\theta b=\varphi-\theta a \quad (4)$$

Accordingly, instruction values of a rotation angle of the first motor 30a and a rotation angle of the third motor 30b can be obtained using the above formulas (3) and (4) on the basis of the distance L between the position P of the joint part 60a and the RCM and the inclination θ of the surgical instrument 5 with respect to the z direction that are set in accordance with a desired position and angle at which the tip of the surgical instrument 5 is desired to be disposed.

In addition, an inclination of the link configuration plane (the x-z plane) in which the arm part 10 is present in the left-right direction is equal to a change amount of a rotation angle of the second motor 30c. Thus, a desired inclination of the surgical instrument 5 in the left-right direction is an instruction value of a rotation angle of the second motor 30c.

As described above, the control device 303 can obtain a target value of a rotation angle of each of the first motor 30a, the second motor 30c, and the third motor 30b on the basis of a position and an angle at which the tip of the surgical instrument 5 is desired to be disposed. In addition, the control device 30 may control a rotation amount of each motor such that, for example, a rotation angle of each motor that can be detected using a potentiometer becomes a calculated target value. Accordingly, an operator can dispose the surgical instrument 5 at a desired position and angle.

Note that an inclination of the tip of the surgical instrument 5 may be given using another index such as a quaternion or an Euler angle in first and second examples. In addition, a way of moving the arm part 10 or the surgical instrument 5 through an input operation with respect to the input device 301 can be appropriately set. For example, the arm part 10 or the surgical instrument 5 may be set to move while input of movement in a predetermined direction is performed using the input device 301, or a movement amount may be set in advance through one input operation and a movement amount of the arm part 10 or the surgical instrument 5 may be decided in accordance with the number of input operations.

(1-4-2. Application Examples)

Next, several application examples of control of each motor by the control device 303 will be described.

(1-4-2-1. First Application Example)

A first application example of control of each motor by the control device 303 is an example of control in which a lock function for holding an attitude of the arm part 10 in a predetermined state can be realized. For example, in a case in which an operator or the like manually operates the arm part 10 to position the tip of the surgical instrument 5 and then rotational torque is applied to the first motor 30a, the second motor 30c, or the third motor 30b from an external force, the control device 303 may cause a current to flow to each of the motors and cause torque against the external force to be generated in order to correct the difference. Accordingly, each of the motors maintains its own original stop position. This lock function can be realized as, for example, a servo lock function in a case in which servo motors are used as the motors. In this case, the rotational torque applied from the external force can be detected on the basis of, for example, pulse signals flowing in the servo motors.

In addition, the lock function may be set to start to be executed when an operator or the like sets the lock function to be on, or when rotation of the first motor 30a, the second motor 30c, and the third motor 30b stops for several seconds (e.g., for three seconds). Furthermore, the lock function may be set to be cancelled when an operator or the like sets the lock function to be off, or when rotational torque is continuously applied from an external force to the first motor 30a, the second motor 30c, or the third motor 30b for several seconds (e.g., for three seconds). Moreover, the lock function may be cancelled when an instruction to operate the arm part 10 is input to the input device 301.

(1-4-2-2. Second Application Example)

A second application example of control of each motor by the control device 303 is an example of control in which an assisting function for giving a supplementary force to an operation of the arm part 10 performed by an operator or the like can be realized. For example, when an operator or the like manually operates the arm part 10, and rotation torque is detected to be applied to each of the first motor 30a, the second motor 30c, and the third motor 30b, the control device 303 may cause a current to flow to each of the motors and cause torque to be generated in the same direction as an external force. At this time, a ratio of torque applied to each motor may be equal to a ratio of rotational torque applied to each motor by the detected external force. Accordingly, the arm part 10 or the surgical instrument 5 can be moved in an operation direction desired by an operator or the like.

<1-5. Modified Examples>

The support arm device 1 according to the present embodiment has been described above, however the support arm device can be variously modified. Several modified examples of the support arm device 1 according to the present embodiment will be described below.

(1-5-1. First Modified Example)

Figure 24:
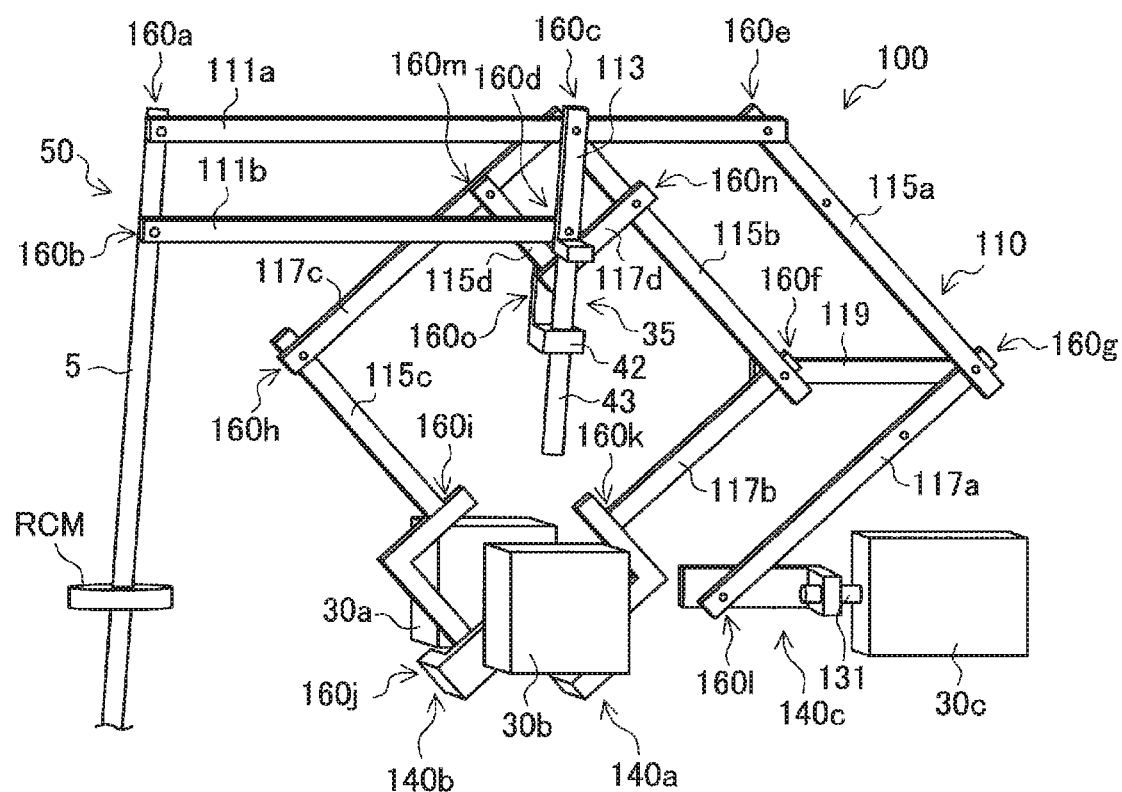
FIG. 24 is a perspective diagram showing a support arm device according to a first modified example.

FIG. 24 is an illustrative diagram showing a support arm device 100 according to a first modified example. The support arm device 100 has a first drive shaft that is an output shaft of a first motor 30a and a third drive shaft that is an output shaft of a third motor 30b disposed on the same axis. That is, although the first motor 30a and the third motor 30b are disposed on one side (the right side) of the link configuration plane in the support arm device 1 according to the above-described embodiment, in the support arm device 100 according to the first modified example, the first motor 30a and the third motor 30b are disposed on both sides of a link configuration plane having the link configuration plane interposed therebetween.

A surgical instrument 5, a support part 50, a plurality of links, motors, a guide pin, a linear bushing, and the like constituting the support arm device 100 each may be similar to those of the support arm device 1 according to the above-described embodiment. Note that, the support arm device 100 includes a base part, which is not illustrated, and motors are fixed to the base part.

An arm part 110 of the support arm device 100 includes a plurality of joint parts 160a to 160o, and a first link 111a, a second link 111b, a third link 113, a fourth link 115a, a fifth link 115b, a sixth link 115c, a seventh link 117a, an eighth link 117b, a ninth link 117c, a tenth link 119, an eleventh link 115d, and an twelfth link 117d that are revolvably connected by each of the joint parts 160a to 160o.

A parallel link is formed by the first link 111a, the second link 111b, the third link 113, and the support part 50. In addition, another parallel link is formed by the fourth link 115a, the fifth link 115b, the first link 111a, and the tenth link 119. In addition, another parallel link is formed by the seventh link 117a, the eighth link 117b, and the tenth link 119. In addition, another parallel link is formed by the fifth link 115b, the sixth link 115c, the eighth link 117b, and the ninth link 117c. Although the ninth link 117c intersects with the second link 111b, the links are not connected. In addition, another parallel link is formed by the fifth link 115b, the ninth link 117c, the eleventh link 115d, and the twelfth link 117d. Although the eleventh link 115d, the twelfth link 117d, and a linear bushing 42 are revolvably connected by the joint part 160o, the components are not connected to the second link 111b and the third link 113, or a guide pin 43.

The plurality of links are present within a common link configuration plane regardless of attitudes of the arm part 110. Thus, the support arm device 100 can reduce a width thereof in the left-right direction. Note that, among the plurality of links, the eighth link 117b corresponds to a first drive link, the seventh link 117a corresponds to a second drive link, and the sixth link 115c corresponds to a third drive link.

The eighth link 117b is connected to a first drive shaft (not illustrated) driven by the first motor 30a via a first orthogonal joint part 140a constituting orthogonal three degrees of freedom. In addition, the seventh link 117a is connected to a second drive shaft 131 driven by the second motor 30c via a second orthogonal joint part 140c constituting orthogonal two degrees of freedom. In addition, the sixth link 115c is connected to a third drive shaft (not illustrated) driven by the third motor 30b via a third orthogonal joint part 140b constituting orthogonal three degrees of freedom. The first orthogonal joint part 140a, the second orthogonal joint part 140c, and the third orthogonal joint part 140b each can be configured similarly to the orthogonal joint parts of the support arm device 1 according to the above-described embodiment.

The guide pin 43 extending from the third link 113 is directed to the direction of the first drive shaft and the third drive shaft at all times regardless of attitudes of the arm part 110, and can move forward and backward within the linear bushing 42. The parallel link formed by the fifth link 115b, the ninth link 117c, the sixth link 115c, and the eighth link 117b and the parallel link formed by the fifth link 115b, the ninth link 117c, the eleventh link 115d, and the twelfth link 117d constitute rhombus structures having the third link 113 and an extended line thereof as a diagonal line. These two rhombus structures can stretch and contract along the diagonal line.

Also in the support arm device 100 according to the first modified example, the arm part 110 is deformed along the link configuration plane remaining in a specific link configuration plane when the first motor 30a and the third motor 30b are rotated in the same direction. At this time, the arm part 110 revolves while the first link 111a and the second link 111b maintains a state in which the links are parallel to a horizontal plane (parallel to the second drive shaft 131) with the extended line of the third link 113 being directed to the direction of the first drive shaft and the third drive shaft at all times. Thus, the surgical instrument 5 supported by the support part 50 revolves forward and backward with respect to the RCM.

In addition, even in a case in which the first motor 30a and the third motor 30b are rotated in the reverse direction, the arm part 110 is deformed along the link configuration plane, remaining within the specific link configuration plane. At this time, the two rhombus structures having the third link 113 and the extended line thereof as a diagonal line stretch and contract along the diagonal line while the first link 111a and the second link 111b maintain the state in which the links are parallel to the horizontal plane (parallel to the axis of the second drive shaft 131) with the extended line of the third link 113 being directed to the direction of the first drive shaft and the third drive shaft at all times. Therefore, the surgical instrument 5 supported by the support part 50 moves forward and backward so as to pass through the RCM at all times.

Furthermore, the arm part 110 is inclined in the left-right direction in accordance with rotation of the second motor 30c. At this time, since the inclination of the entire arm part 110 changes, the plurality of links constituting the arm part 110 are inclined in the left-right direction remaining in the common link configuration plane. Since the arm part 110 revolves with respect to the axis of the second drive shaft 131, the surgical instrument 5 revolves with respect to the RCM that is provided on the axis of the second drive shaft 131 in the left-right direction.

Configurations other than the points described above can be similar to those of the support arm device 1 according to the above-described embodiment. For example, the support arm device 100 according to the first modified example can also be controlled by a control device similar to that of the support arm device 1 according to the above-described embodiment.

As described above, the support arm device 100 according to the first modified example also has a relative simple structure including the plurality of links that are connected to each other and three motors, and thus manufacturing costs thereof can be reduced. In addition, since the arm part 110 constituted by the plurality of links is presented within the link configuration plane as a whole, the support arm device 100 according to the first modified example has a small width in the left-right direction, and thus can occupy a reduced volume.

Furthermore, the support arm device 100 according to the first modified example also has a configuration in which the first motor 30a, the second motor 30c, and the third motor 30b do not move when the arm part 110 changes its attitude. Thus, weights of parts that are movable by each of the motors can be relatively light and output of the motors can be reduced. Accordingly, the motors can be miniaturized or an amount of power consumption can be reduced.

(1-5-2. Second Modified Example)

Figure 25:
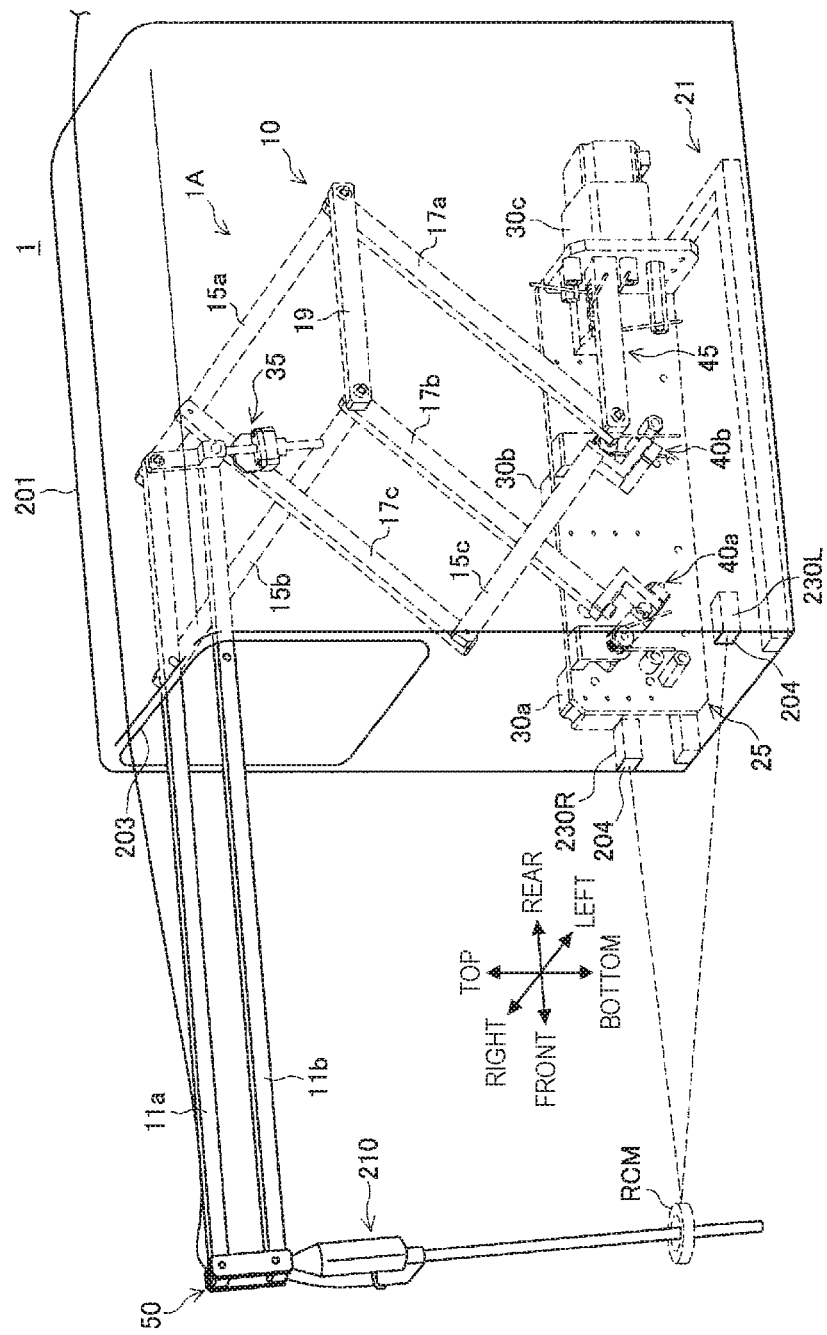
FIG. 25 is a perspective diagram showing a support arm device according to a second modified example.

FIG. 25 shows a support arm device 1A according to a second modified example. The support arm device 1A according to the second modified example is different from the support arm device 1 according to the above-described embodiment in that a pair of laser irradiation parts 230R and 230L is provided to facilitate visual recognition of a position of the RCM.

The pair of laser irradiation parts 230R and 230L illustrated in FIG. 25 is provided inside a cover 201. The laser irradiation parts 230R and 230L switches between, for example, laser light irradiation and stop in accordance with an input operation of turning on or off by an operator or the like. The cover 201 has two openings 204, and layer light irradiated from the laser irradiation parts 230R and 230L is irradiated to the outside of the cover 201 through the openings 204. The pair of laser irradiation parts 230R and 230L each irradiates layer light beams toward the RCM. An intersection point of the laser light beams irradiated from the pair of laser irradiation parts 230R and 230L coincides with the RCM.

Thus, when an operator or the like decides an installation position of the support arm device 1A, an installation position of the support arm device 1A can be easily decided by installing the support arm device 1A such that, for example, an intersection point of laser light beams coincides with an insertion hole formed by incising a body surface of a patient or the like. Accordingly, the support arm device 1A can be set at a proper position before an operation starts with a tip of the surgical instrument 5 such as an endoscope held above the RCM.

Installation positions of the laser irradiation parts 230R and 230L can be appropriately set. For example, by irradiating laser light toward the RCM from a position higher than the RCM, the laser light is seldom blocked by a patient himself or herself, another facility, or the like. In addition, the laser irradiation parts 230R and 230L are an aspect for indicating a position of the RCM, and a means for facilitating visual recognition of a position of the RCM is not limited to the laser irradiation parts 230R and 230L.

In addition, the laser irradiation parts 230R and 230L may be detachable from a predetermined position outside the cover 201. In this case, the unitized pair of laser irradiation parts 230R and 230L may be placed at, for example, a predetermined position of an upper surface of the cover 201. When, for example, an operator or the like decides an installation position of the support arm device 1A, the laser irradiation parts 230R and 230L can be mounted in the cover 201 for positioning, and after an installation position thereof is decided, the laser irradiation parts 230R and 230L can be taken out and a surgery or the like is performed.

(1-5-3. Third Modified Example)

Figure 26:
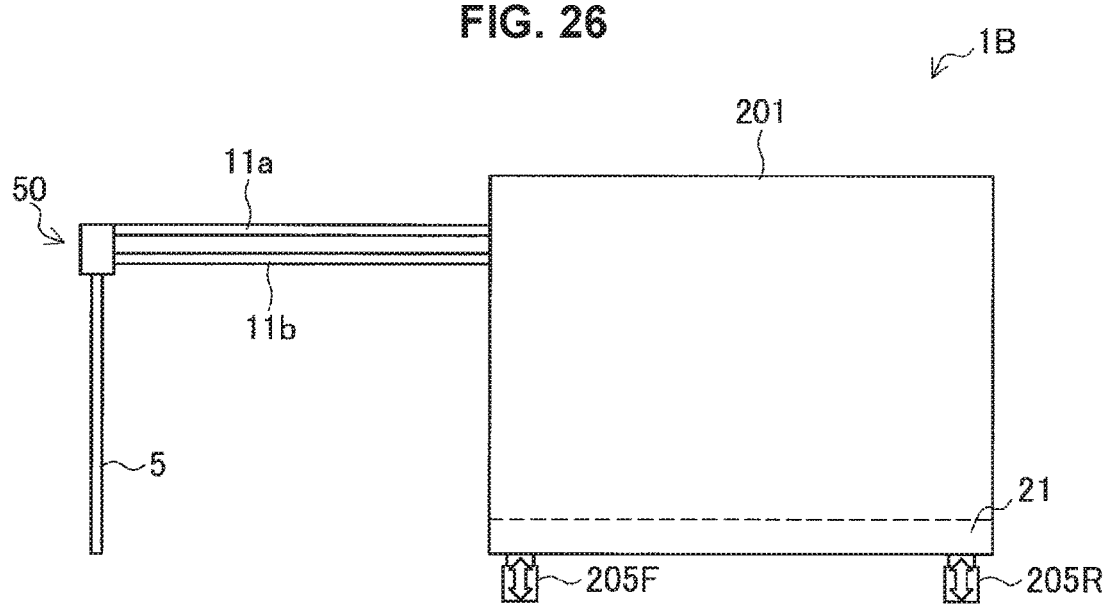
FIG. 26 is an illustrative diagram showing a support arm device according to a third modified example.

FIG. 26 is a schematic diagram showing a support arm device 1B according to a third modified example. The support arm device 1B according to the third modified example is different from the support arm device 1 according to the above-described embodiment in that a height adjustment part 205F and 205R for adjusting a height of the support arm device 1B is provided.

The support arm device 1B includes the height adjustment parts 205F and 205R mounted on the base part 21. The height adjustment parts 205F and 205R include the height adjustment part 205F on a front side and the height adjustment part 205R on a rear side. The height adjustment parts 205F and 205R are not particularly limited as long as the parts can adjust a (length) height in the top-bottom direction. For example, the height adjustment parts 205F and 205R can be motor-driven extension devices, hydraulic or pneumatic-driven cylinder device, or the like.

An operator or the like drives the height adjustment parts 205F and 205R when deciding an installation position of the support arm device 1B before starting a surgery, for example, so that an insertion hole formed by incising a body surface of a patient or the like coincides with the RCM. At this time, an inclination of the entire support arm device 1B may be adjusted by driving only one of the height adjustment parts 205F and 205R or causing the height adjustment parts 205F and 205R to have different heights.

As described above, since the support arm device 1B according to the third modified example is set to have an adjustable height or inclination, an insertion hole formed on a body surface of a patient can be caused to coincide with the RCM while the support arm device 1B is appropriately disposed in accordance with a situation of the patient or another facility.

<1-6. Conclusion>

As described above, the support arm device according to the present embodiment can realize a parallel mechanism having three degrees of freedom in which translational motion having one degree of freedom in an axis direction of a surgical instrument supported by the arm part and rotational motions in which the axis is inclined to the front, rear, left, and right by changing an attitude of the arm part. The support arm device has a configuration in which the first motor, the second motor, and the third motor do not move when the arm part changes its attitude. Therefore, weights of parts operated by each of the motors can be relatively light and output of each of the motors can be reduced. Accordingly, the motors can be miniaturized, or an amount of power consumption can be reduced. In addition, since each of the motors is fixed to the base part and thus do not move, electric wiring becomes simple accordingly.

In addition, the support arm device according to the present embodiment can reduce manufacturing costs due to the relatively simple structure constituted by the plurality of links connected to each other and the three motors. Furthermore, since the arm part configured by the plurality of links is present within the link configuration plane as a whole, the support arm device has a small width in the left-right direction, and thus can occupy a reduced volume Furthermore, the support arm device according to the present embodiment is connected to the drive shafts of the three motors using two orthogonal joint parts each constituting three degrees of freedom and one orthogonal joint part constituting two degrees of freedom. Thus, the arm part can change its attitude with the three motors fixed to the base part. In addition, since the arm part is connected to the drive shafts via the orthogonal joint parts, rotation of each of links is not obstructed when the arm part changes its attitude.

In addition, the support arm device according to the present embodiment includes a linear bushing that guides a guide pin extending from the third link facing one side constituting the support part supporting a surgical instrument in the axial direction of the guide pin, and has a structure in which the surgical instrument moves forward and backward in the axial direction. Thus, the surgical instrument is directed toward the RCM at all times. Since the guide structure using the guide pin and the linear bushing can have a relatively short length, light-weight and a low manufacturing cost of the arm part can be achieved.

2. Second Embodiment

Next, a support arm device according to a second embodiment of the present disclosure will be described. The support arm device according to the present embodiment is configured using a smaller number of links than the support arm device 1 according to the first embodiment, and thus can be configured as a smaller-sized device. Differences from the support arm device according to the first embodiment will be mainly described below.

<2-1. Configuration of Support Arm Device>

Figure 27:
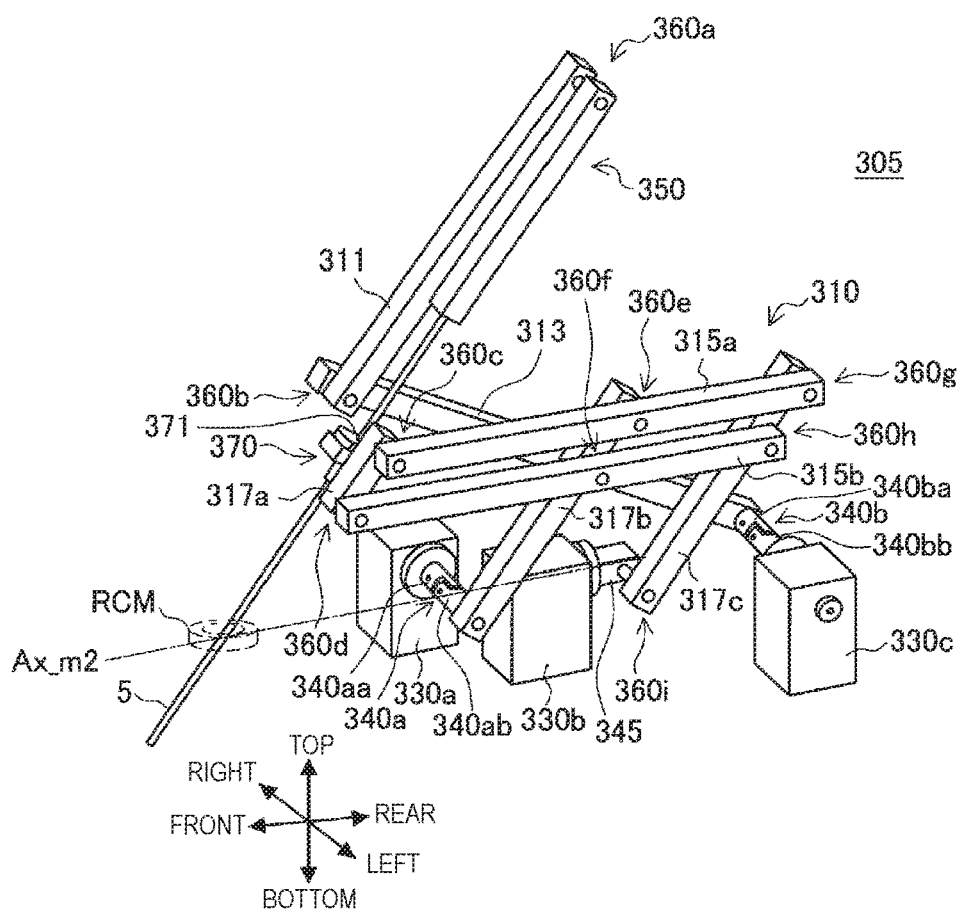
FIG. 27 is a perspective diagram showing an example of a configuration of a support arm device according to a second embodiment of the present disclosure.

FIG. 27 is a perspective diagram showing an example of a configuration of a support arm device 305 according to the present embodiment. The support arm device 305 has an arm part 310 including at least one parallel link. By operating the arm part 310 using a first motor 330a, a second motor 330b, and a third motor 330c, pivotal motions with respect to the RCM and translational motions along a straight line passing through the RCM are realized. Note that a cover or a base part may be provided for the support arm device 305.

A universal joint 340a serving as a first drive shaft is connected to an output shaft of the first motor 330a, and the first motor 330a causes the universal joint 340a to perform shaft rotation. The universal joint 340a has a base part 340aa co-axially fixed to the output shaft of the first motor 330a, and a revolving part 340ab is revolvably connected to the base part 340aa. An output shaft of the second motor 330b co-axially fixed to a second drive shaft 345, and the second motor 330b causes the second drive shaft 345 to perform shaft rotation. A universal joint 340b serving as a third drive shaft is connected to an output shaft of the third motor 330c, and the third motor 330c causes the universal joint 340b to perform shaft rotation. The universal joint 340b has a base part 340ba co-axially fixed to the output shaft of the third motor 330c, and a revolving part 340bb is revolvably connected to the base part 340ba.

The axis of the base part 340aa of the universal joint 340a and the axis of the base part 340ba of the universal joint 340b are disposed in equidistant parallel to each other. Although the axis of the base part 340aa of the universal joint 340a and the axis of the base part 340ba of the universal joint 340b are better to be disposed on a plane parallel to each other, if the axes are in an equidistant parallel state, pivotal motions with respect to the RCM controlled by the first motor 330a, the second motor 330b, and the third motor 330c can be easily made. In addition, if the axis of the base part 340aa of the universal joint 340a and the axis of the base part 340ba of the universal joint 340b are in the equidistant parallel state, transfer efficiency of motor torque can be prevented from decreasing. Furthermore, if the axis of the base part 340aa of the universal joint 340a and the axis of the base part 340ba of the universal joint 340b are in the equidistant parallel state, design of the device becomes easier and production efficiency is improved accordingly.

In addition, the axis of the second drive shaft 345 is orthogonal to each of the axis of the base part 340aa of the universal joint 340a and the axis of the base part 340ba of the universal joint 340b. In the support arm device 305 according to the present embodiment, the axis of the base part 340aa of the universal joint 340a, the axis of the base part 340ba of the universal joint 340b, and the axis of the second drive shaft 345 are disposed on a plane parallel to an installation surface on which the support arm device 305 is installed. The RCM that serves as the center of pivotal motions of a surgical instrument 5 is further disposed on the axis of the second drive shaft 345.

The arm part 310 includes at least one parallel link constituted by a plurality of links. The arm part 310 includes a plurality of joint parts 360a to 360i, and a first link 311, a second link 313, a third link 315a, a fourth link 315b, a fifth link 317a, a sixth link 317b, and a seventh link 317c that are revolvably connected to each other by the joint parts 360a to 360i. In addition, the arm part 310 has a support part 350 for supporting the surgical instrument 5 at its tip. In the support arm device 305 according to the present embodiment, a parallel link is formed by the third link 315a, the fourth link 315b, the fifth link 317a, the sixth link 317b, and the seventh link 317c. The second link 313 is not connected to the sixth link 317b and the seventh link 317c.

Note that, among the plurality of links, the sixth link 317b corresponds to a first drive link, the seventh link 317c corresponds to a second drive link, and the second link 313 corresponds to a third drive link.

The plurality of links are present within a common link configuration plane regardless of attitudes of the arm part 310. That is, a parallel link formed by the plurality of links is present within the common link configuration plane regardless of attitudes of the arm part 310. Thus, the support arm device 305 can have a smaller width in the left-right direction. While an inclination of the link configuration plane is not changed during operations of the arm part 310 in the front-rear direction and the top-bottom direction, an inclination thereof can be changed during operations of the arm part 310 in the left-right direction. Note that, in the support arm device 305 according to the present embodiment, the link configuration plane has a thickness equivalent to five links.

In addition, in the support arm device 305 according to the present embodiment, a guide structure 370 is provided in the fifth link 317a. The guide structure 370 has a guide hole 371 with an axis along a longitudinal direction of the fifth link 317a. The axis of the guide hole 371 is positioned on a straight line passing through the RCM. The surgical instrument 5 is inserted into the guide hole 371, and is held so as to perform translational motions in the longitudinal direction of the fifth link 317a. Thus, the surgical instrument 5 or the axis of the surgical instrument 5 passes through the RCM at all times regardless of attitudes of the arm part 310.

The sixth link (the first drive link) 317b is connected to the first motor 330a via the universal joint 340a. By driving the first motor 330a, the base part 340aa of the universal joint 340a performs shaft rotation, and the sixth link 317b revolves around the axis of the base part 340aa of the universal joint 340a regardless of attitudes of the arm part 310. At this time, the fifth link 317a and the seventh link 317c revolve while maintaining a state parallel to the sixth link 317b. Accordingly, a parallel link formed by the third link 315a, the fourth link 315b, the fifth link 317a, the sixth link 317b, and the seventh link 317c revolves in the front-back direction. At this time, since the fifth link 317a is directed to the RCM at all times, the surgical instrument 5 supported by the guide structure 370 or the axis of the surgical instrument 5 passes through the RCM at all times.

As described above, by the first motor 330a being driven to cause the sixth link 317b to revolve, the surgical instrument 5 can revolve in the front-rear direction with respect to the RCM. Note that, when the surgical instrument 5 revolves only in the front-back direction, the plurality of parallel links of the arm part 310 are deformed along the link configuration plane, remaining in a specific link configuration plane.

The second link (the third drive link) 313 is connected to the third motor 330c via the universal joint 340b. By driving the third motor 330c, the base part 340ba of the universal joint 340b performs shaft rotation, and the second link 313 revolves with respect to the base part 340ba of the universal joint 340b, regardless of attitudes of the arm part 310. Accordingly, a position of the support part 350 connected to the second link 313 via the first link 311 is changed, and the surgical instrument 5 supported by the support part 350 performs a translational motion along a straight line passing through the RCM.

The seventh link (the second drive link) 317c is revolvably connected to the second drive shaft 345 via the joint part 360i. When the second motor 330b is driven and the second drive shaft 345 performs shaft rotation, each link revolves with respect to the axis of the second drive shaft 345 in the left-right direction. Since the sixth link 317b is connected to the first motor 330a via the universal joint 340a and the second link 313 is connected to the third motor 330c via the universal joint 340b, each of the links can revolve in the left-right direction without interfering in each other. At this time, since the guide hole 371 of the guide structure 370 and the surgical instrument 5 held in the guide hole 371 relatively rotate, operations of each of the link are not obstructed.

As described above, by driving the second motor 330b, an inclination of the link configuration plane is changed in the left-right direction with respect to the second drive shaft 345. Since the axis of the guide hole 371 of the guide structure 370 is directed to the RCM at all times, the surgical instrument 5 or the axis of the surgical instrument 5 passes through the RCM at all times, regardless of attitudes of the arm part 310.

In the support arm device 1 according to the first embodiment, the third motor 30b is provided between the first motor 30a and the second motor 30c, and it is necessary to set the fourth link 15a and the seventh link 17a forming a rhombus structure to be long in order to widen a range of translational motions of the surgical instrument 5. Thus, if the support arm device 1 according to the first embodiment is miniaturized, a vertical movement range of the surgical instrument 5 should be reduced. On the other hand, in the support arm device 305 according to the second embodiment, a rhombus structure for moving the surgical instrument 5 upward and downward is omitted, and the third motor 330c provided at a farthest position from the RCM causes a position of the surgical instrument 5 to move upward and downward. Accordingly, a relatively wide movable range can be secured even if the support arm device 305 is miniaturized.

<2-2. Attitude of Arm Part>

The configuration of the support arm device 305 according to the present embodiment has been described above. Next, various attitudes that the arm part 310 of the support arm device 305 can take will be described. FIG. 28 to FIG. 32 show examples of attitudes of the arm part 310 performing pivotal motions and translational motions. In FIG. 28 to FIG. 32, virtual lines indicating the attitude (a basic attitude) of the arm part 310 of FIG. 27 are shown in order to facilitate comparison to the attitude of the arm part 310 of FIG. 27. In FIG. 27, the surgical instrument 5 is supported in a state in which the surgical instrument is falling backward, and is in a state in which a tip portion thereof enters the RCM.

Figure 28:
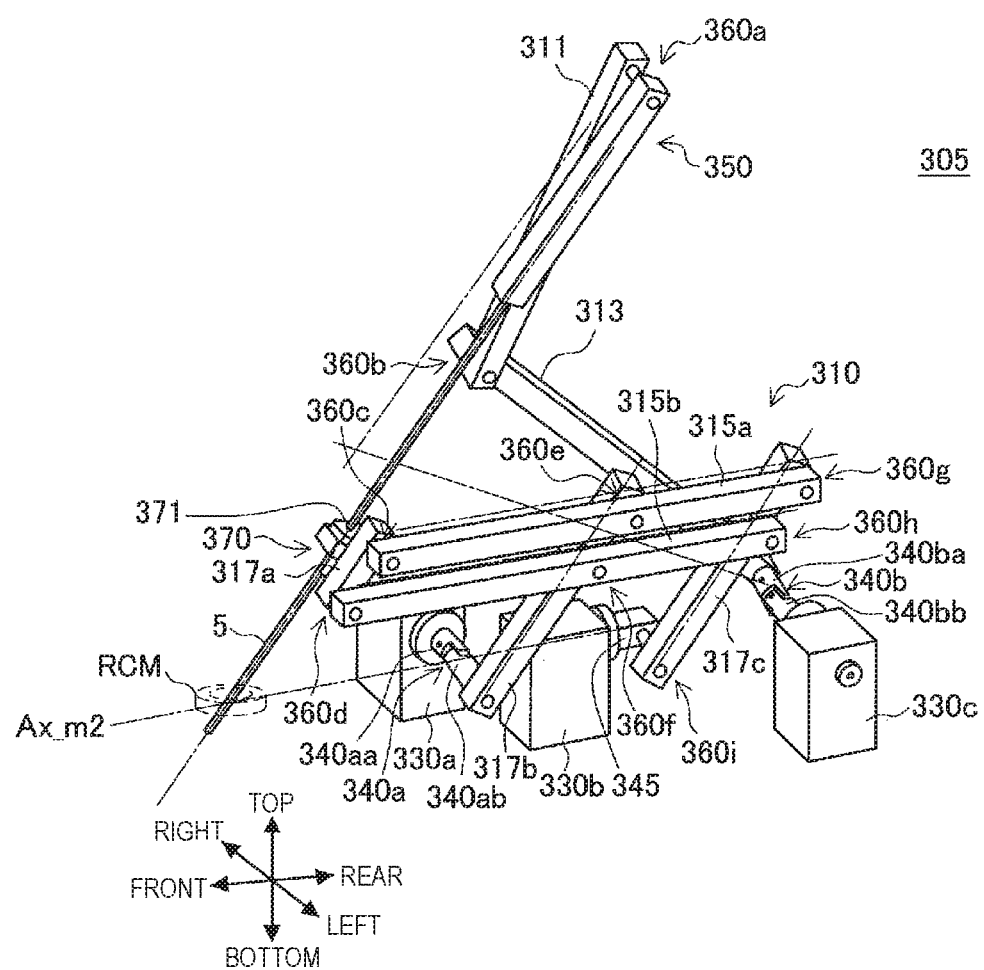
FIG. 28 is a diagram for describing change of an attitude of the arm part.

FIG. 28 shows an attitude of the arm part 310 in a case in which the third motor 330c rotates from the state of FIG. 27 in the clockwise direction of the drawing. In this case, the second link 313 revolves with respect to the axis of the base part 340ba of the universal joint 340b in the clockwise direction of the drawing, and the first link 311 and the support part 350 connected to the first link 311 are pushed upward. As a result, the surgical instrument 5 ascends along a straight line passing through the RCM maintaining the basic attitude and the same inclination as in FIG. 27.

Figure 29:
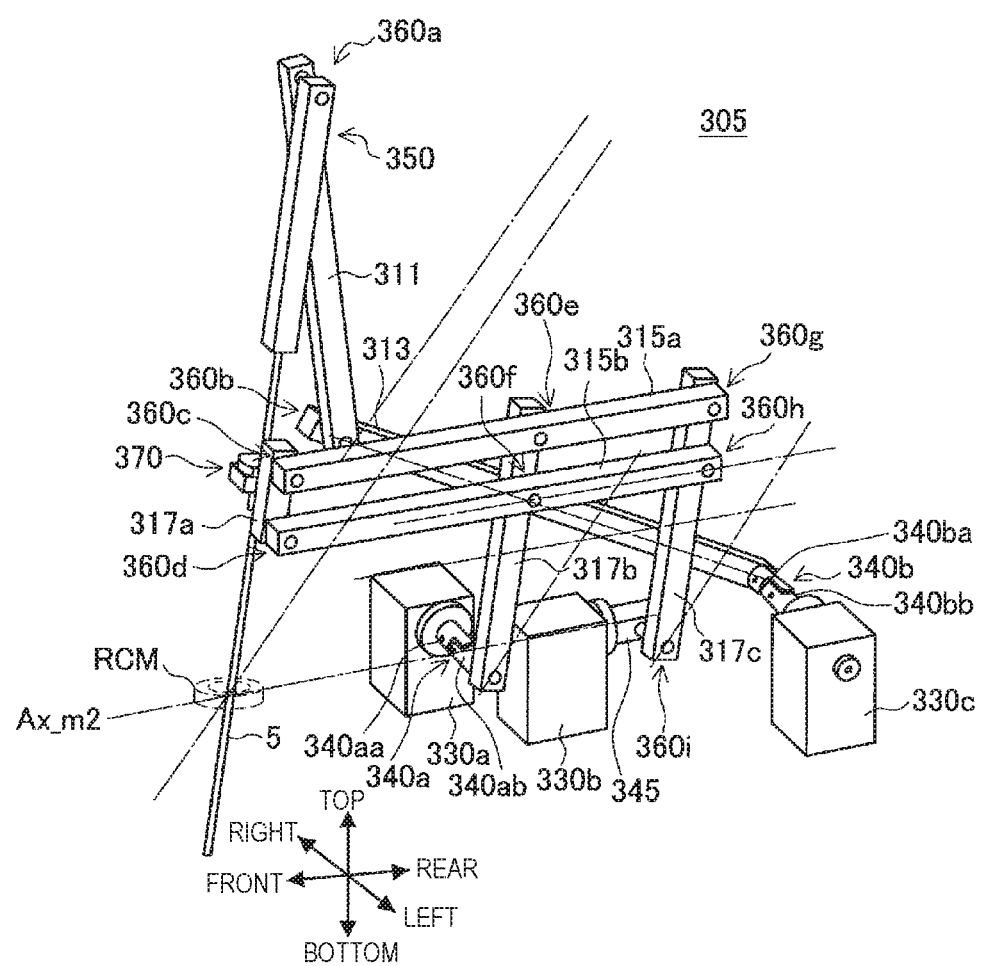
FIG. 29 is a diagram for describing change of an attitude of the arm part.

FIG. 29 shows an attitude of the arm part 310 in a case in which the first motor 330a rotates from the state of FIG. 27 in the counterclockwise direction of the drawing. In this case, the sixth link 317b revolves with respect to the axis of the base part 340aa of the universal joint 340a in the counterclockwise direction of the drawing. Accordingly, the arm part 310 revolves forward with the third link 315a and the fourth link 315b while maintaining a state parallel to the installation surface of the support arm device 305. As a result, the surgical instrument 5 revolves forward with respect to the RCM.

Figure 30:
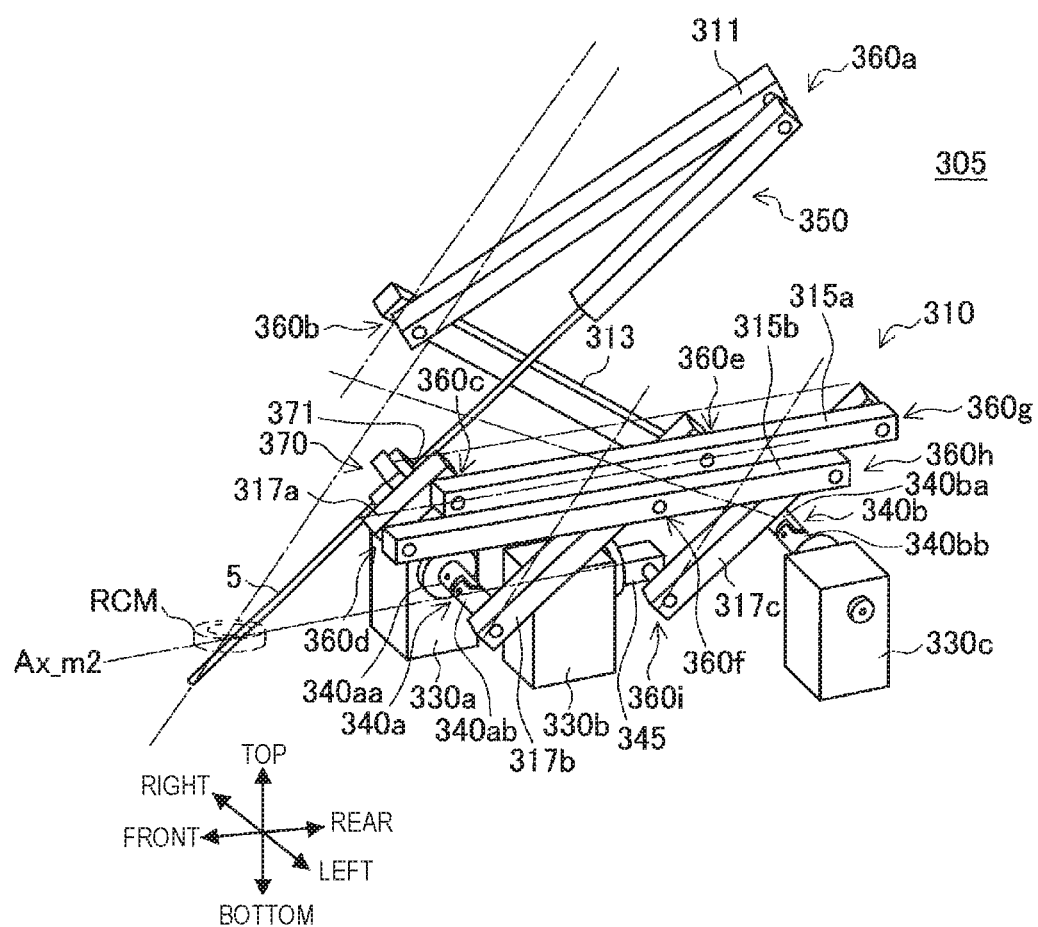
FIG. 30 is a diagram for describing change of an attitude of the arm part.

FIG. 30 shows an attitude of the arm part 310 in a case in which the first motor 330a rotates in the clockwise direction of the drawing and the third motor 330c rotates in the clockwise direction of the drawing from the state of FIG. 27. In this case, due to the driving of the first motor 330a, the sixth link 317b revolves with respect to the axis of the base part 340aa of the universal joint 340a in the clockwise direction of the drawing. In addition, due to the driving of the third motor 330c, the second link 313 revolves with respect to the axis of the base part 340ba of the universal joint 340b in the clockwise direction of the drawing. Accordingly, the arm part 310 revolves backward with the third link 315a and the fourth link 315b while maintaining a state parallel to the installation surface of the support arm device 305, and the first link 311 and the support part 350 connected to and the first link 311 are pushed upward. As a result, the surgical instrument 5 ascends while revolving backward with respect to the RCM.

Figure 31:
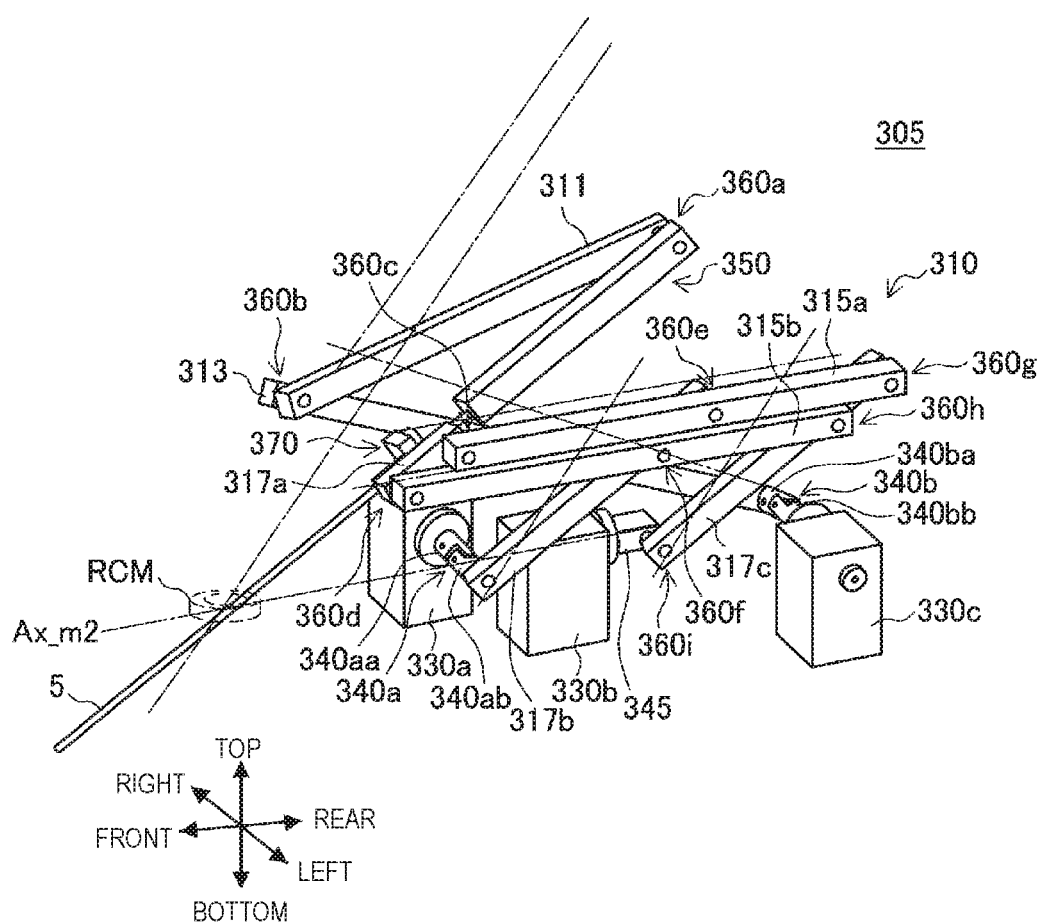
FIG. 31 is a diagram for describing change of an attitude of the arm part.

FIG. 31 shows an attitude of the arm part 310 in a case in which the first motor 330a rotates in the clockwise direction of the drawing and the third motor 330c rotates in the counterclockwise direction of the drawing from the state of FIG. 27. In this case, by the first motor 330a being driven, the sixth link 317b revolves with respect to the axis of the base part 340aa of the universal joint 340a in the clockwise direction of the drawing. In addition, by the third motor 330c being driven, the second link 313 revolves with respect to the base part 340ba of the universal joint 340b rotated in the counterclockwise direction of the drawing. Accordingly, while the third link 315a and the fourth link 315b maintains a state parallel to the installation surface of the support arm device 305, the arm part 310 revolves backward, and the first link 311 and the support part 350 connected to the first link 311 are pushed downward. As a result, the surgical instrument 5 descends while revolving backward with respect to the RCM. At this time, the revolving part 340 bb of the universal joint 340b connected to the third motor 330c revolves with respect to the base part 340ba, and thereby, and therefore the links constituting the arm part 310 can avoid interference in each other.

Figure 32:
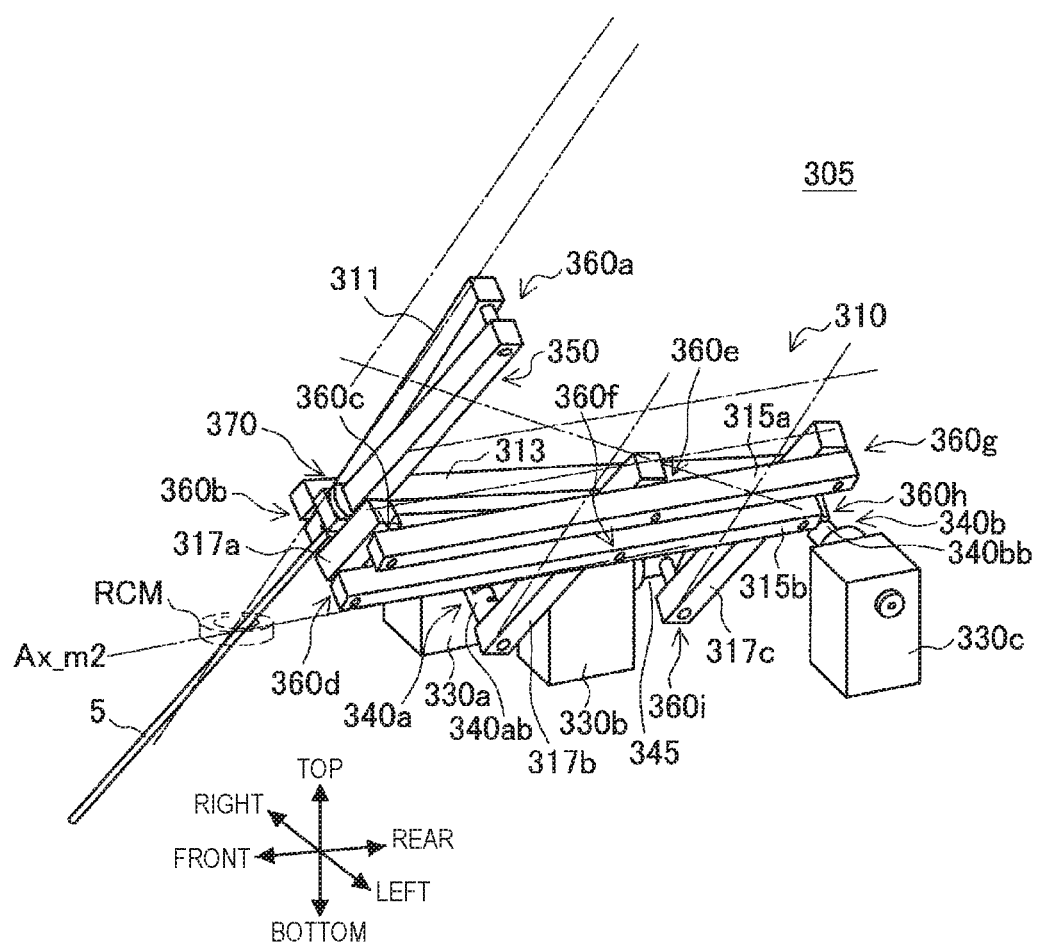
FIG. 32 is a diagram for describing change of an attitude of the arm part.

FIG. 32 shows an attitude of the arm part 310 in a case in which the second motor 330b rotates in the clockwise direction of the drawing and the third motor 330c rotates in the counterclockwise direction of the drawing from the state of FIG. 27. In this case, by the second motor 330b, the seventh link 317c revolves with respect to the axis of the second drive shaft 345 in the clockwise direction of the drawing. In addition, by the third motor 330c being driven, the second link 313 revolves with respect to the axis of the base part 340ba of the universal joint 340b in the counterclockwise direction of the drawing. Accordingly, the arm part 310 revolves with respect to the axis of the second drive shaft 345 such that the link configuration plane is inclined to the left, and the first link 311 and the support part 350 connected to the first link 311 are pushed downward. As a result, the surgical instrument 5 descends while revolving with respect to the RCM in the left direction. At this time, the revolving part 340ab of the universal joint 340a connected to the first motor 330a revolves with respect to the base part 340aa, and the revolving part 340bb of the universal joint 340b connected to the third motor 330c revolves with respect to the base part 340ba, and therefore the links constituting the arm part 310 can avoid interference in each other.

As exemplified above, the support arm device 305 according to the present embodiment can cause the surgical instrument 5 to perform pivotal motions with respect to the RCM and translational motions along a straight line passing through the RCM by driving each of the first motor 330a, the second motor 330b, and the third motor 330c to control attitudes of the arm part 310. Configurations other than the above-described points can be similar to that of the support arm device 1 according to the first embodiment.

<2-3. Conclusion>

As described above, the support arm device 305 according to the present embodiment can also have similar effects to the support arm device according to the first embodiment. In addition, in the support arm device 305 according to the present embodiment, pivotal motions and translational motions of the surgical instrument 5 are possible due to the relatively simple link structure in which the third motor 330c is disposed at a farthest position from the RCM. Accordingly, the support arm device 305 can be miniaturized while a wide range of translational motion is maintained.

In addition, in the support arm device 305 according to the present embodiment, the arm part 310 is connected to the first motor 330a that rotates the arm part 310 in the front-rear direction and the third motor 330c that moves the surgical instrument 5 in the top-bottom direction via the universal joints 340a and 340b. Therefore, when the arm part 310 changes its attitude, rotation of each of the links is not obstructed, and the number of components is smaller than that of the support arm device according to the first embodiment, which enables further miniaturization of the support arm device 305 to be realized.

3. Third Embodiment

Next, a support arm device according to a third embodiment of the present disclosure will be described. Although the support arm devices according to the first embodiment and the second embodiment perform pivotal motions and translational motions such that a tool such as a surgical instrument or an axis of the tool passes through the RCM, the support arm device according to the present embodiment performs rotational motions and translational motions such that a tool or an axis of the tool intersects with a predetermined axis. Differences from the support arm device 1 according to the first embodiment will be mainly described below.

<3-1. Configuration of Support Arm Device>

Figure 33:
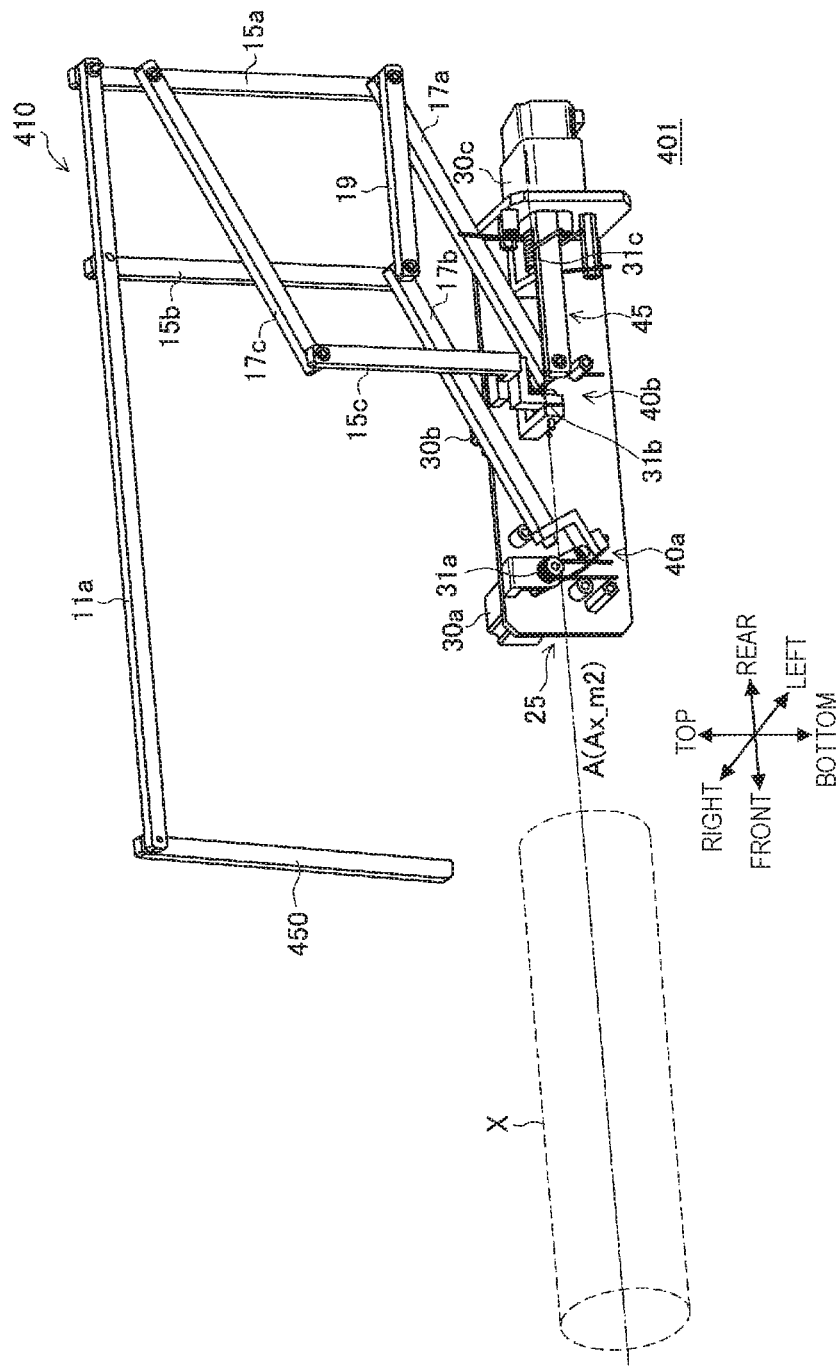
FIG. 33 is a perspective diagram showing an example of a configuration of a support arm device according to a third embodiment of the present disclosure.

FIG. 33 is a perspective diagram showing an example of a configuration of a support arm device 401 according to the present embodiment. The support arm device 401 is a device formed by omitting the second link 11b, the third link 13, and the guide structure 35 from the support arm device 1 according to the first embodiment shown in FIG. 2. An arm part 410 of the support arm device 401 includes a parallelogram structure formed by a first link 11a, a tenth link 19, a fourth link 15a, and a fifth link 15b, a parallelogram structure formed by a seventh link 17a, an eighth link 17b, and the tenth link 19, and a rhombus structure formed by the fourth link 15a, a sixth link 15c, the seventh link 17a, and a ninth link 17c.

In the support arm device 401, the first link 11a maintains a state parallel to an installation surface of the support arm device 401 regardless of attitudes of the arm part 410. In addition, since a second link, a third link, and a guide structure are omitted, when the first link 11a moves in the front-back direction, a support part 450 moves in the front-rear direction with no change in inclination of the support part 450. Thus, the axis of the support part 450 is directed to an axis A extending in front-rear direction at all times, not to a point (the RCM). The axis A can coincide with a rotation axis Ax_m2 of a second drive shaft 31c.

In addition, in the support arm device 401, the support part 450 that support a tool is fixed to the first link 11a to be held thereby at a predetermined angle. In the example of the support arm device 401 shown in FIG. 33, the support part 450 is fixed to the first link 11a having an angle of 90°. Thus, the axis of the support part 450 is orthogonal to the axis A at all times.

<3-2. Attitude of Arm Part>

Next, various attitudes that the arm part 410 of the support arm device 401 can take will be described. FIG. 34 to FIG. 40 show examples of attitudes of the arm part 410 performing rotational motions of the support part 450 with respect to the predetermined axis A and translational motion of the support part 450 along a straight line passing through the axis A. In FIG. 34 to FIG. 40, virtual lines indicating the attitude (a basic attitude) of the arm part 410 of FIG. 33 are shown in order to facilitate comparison to the attitude of the arm part 410 of FIG. 33. In FIG. 33, the axis of the support part 450 is orthogonal to the axis A on a relatively backward side.

Figure 34:
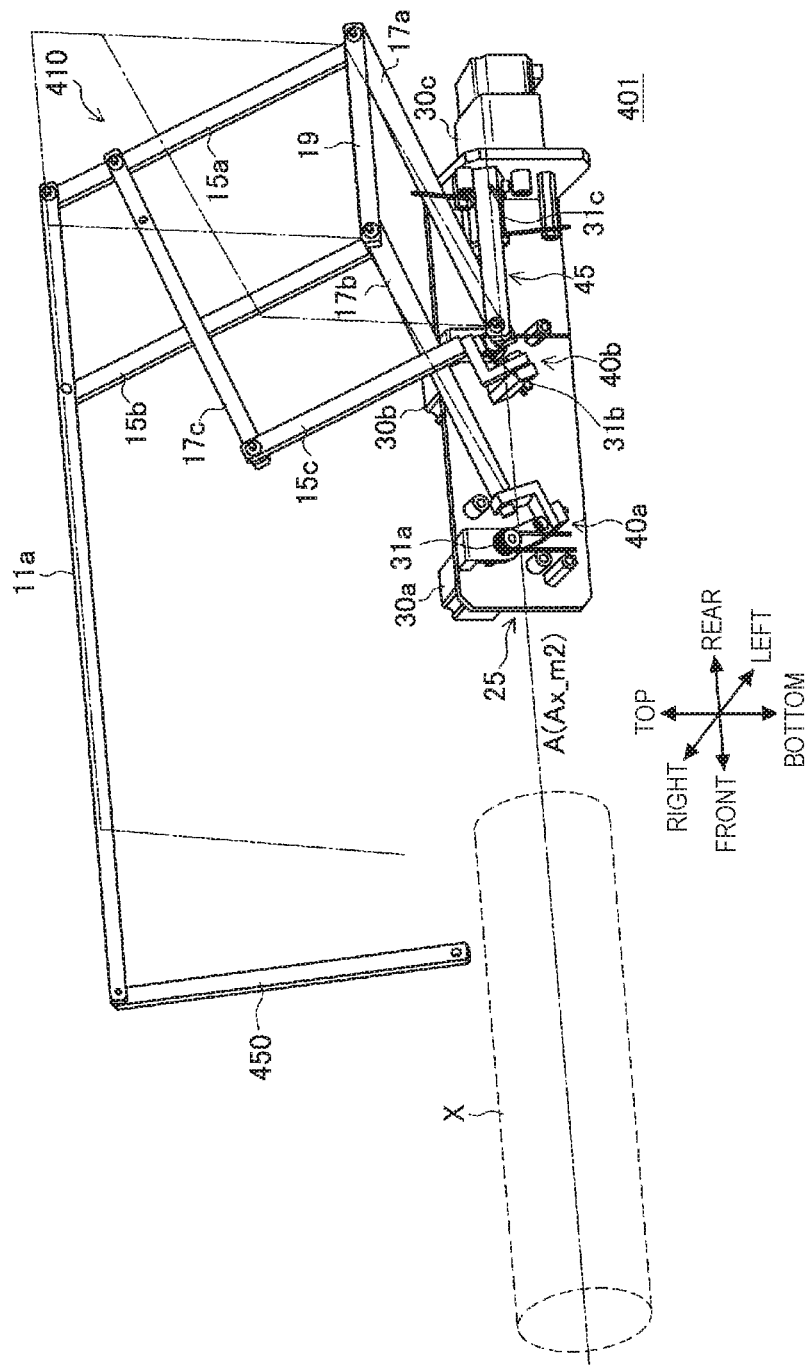
FIG. 34 is a diagram for describing change of an attitude of the arm part.

FIG. 34 shows an attitude of the arm part 410 in a case in which a second motor 30c rotates in the right direction and a third motor 30b rotates in the counterclockwise direction of the drawing from the state of FIG. 33. In this case, by the third motor 30b being driven, the sixth link 15c revolves with respect to a third drive shaft 31b in the counterclockwise direction, and the fourth link 15a and the fifth link 15b are inclined forward keeping a parallel state. Thus, the first link 11a to which the support part 450 is fixed gets closer to the axis A while moving forward. In addition, by the second motor 30c being driven, a link configuration plane revolves with respect to a second drive shaft 30c in the right direction and the axis of the support part 450 is inclined in the right direction. Accordingly, the support part 450 moves forward while inclining in the right direction, and a tip of the support part 450 gets closer to the axis A.

Figure 35:
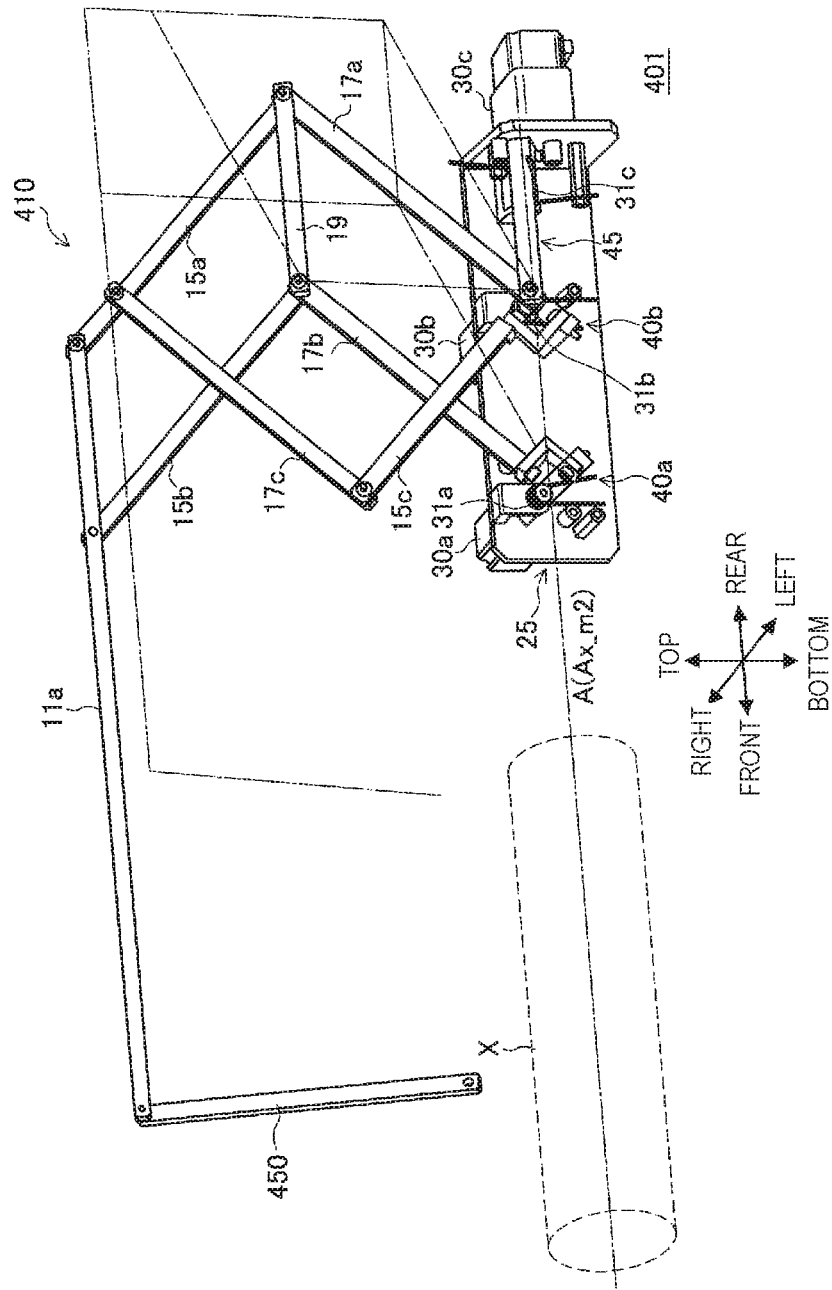
FIG. 35 is a diagram for describing change of an attitude of the arm part.
Figure 36:
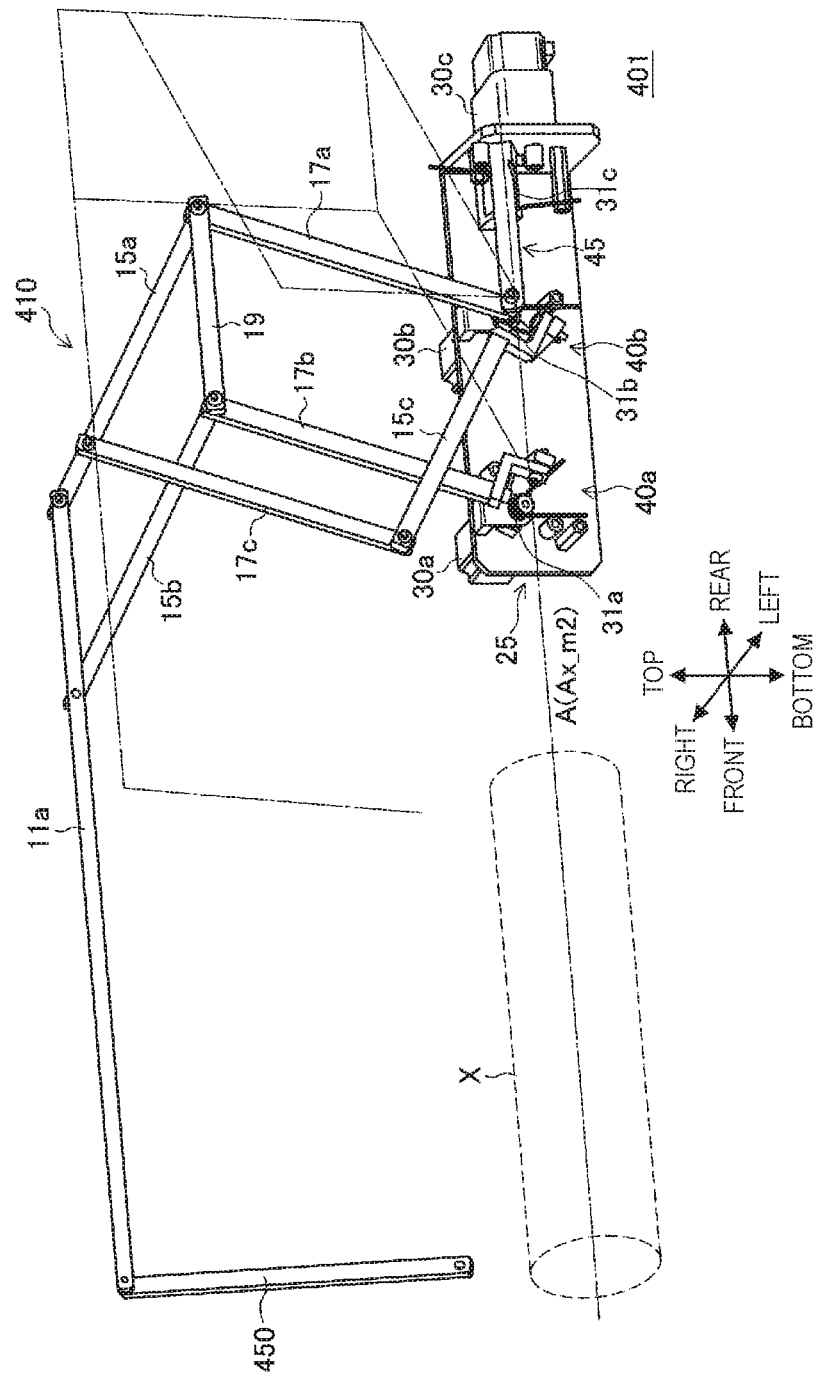
FIG. 36 is a diagram for describing change of an attitude of the arm part.

FIG. 35 and FIG. 36 show attitudes of the arm part 410 in a case in which a first motor 30a and the third motor 30b gradually rotate further in the counterclockwise direction of the drawing from the state of FIG. 34. In this case, the support part 450 moves forward by inches while the axis of the support part 450 maintains a state orthogonal to the axis A.

Figure 37:
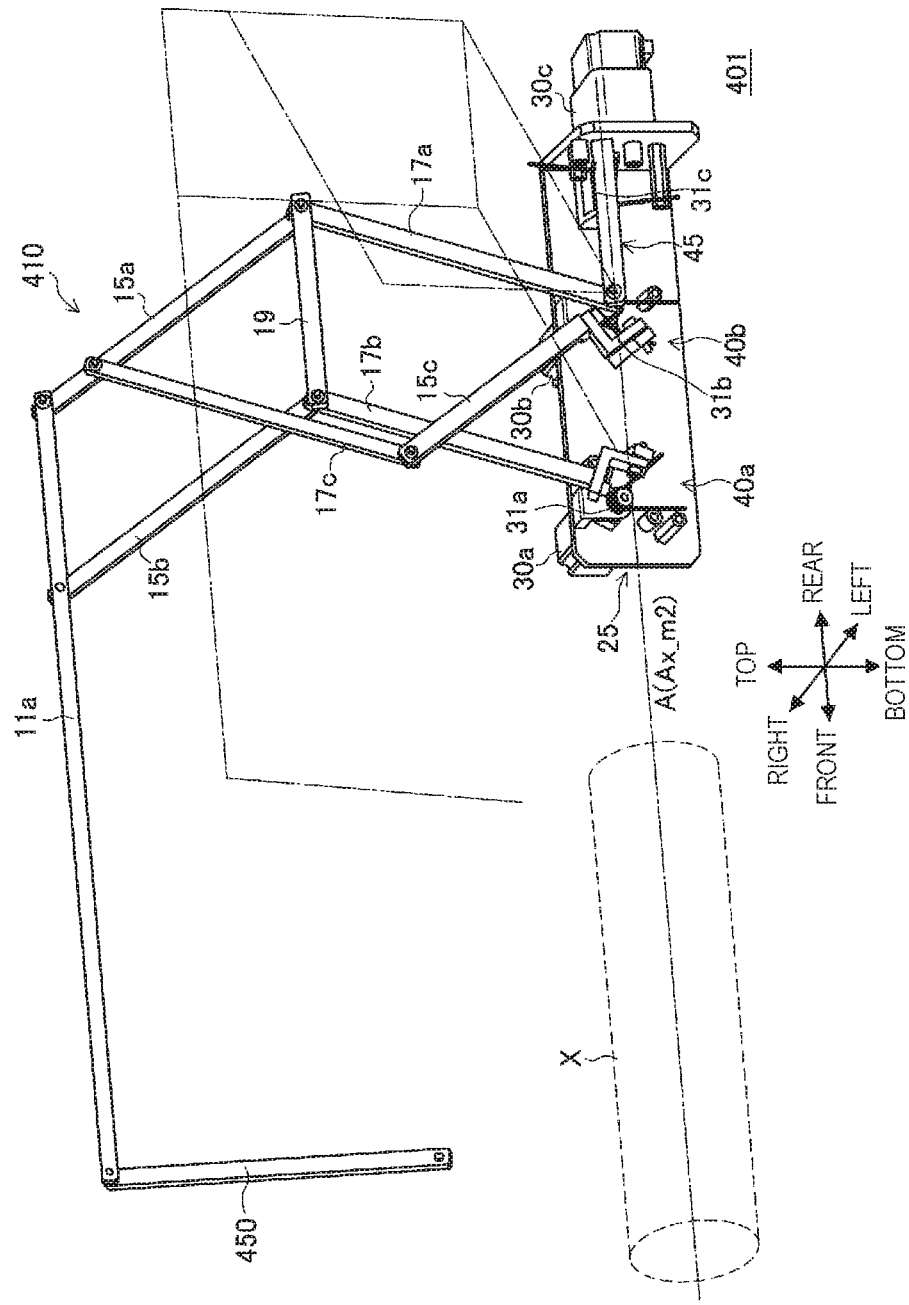
FIG. 37 is a diagram for describing change of an attitude of the arm part.

FIG. 37 shows an attitude of the arm part 410 in a case in which the first motor 30a rotates in the counterclockwise direction of the drawing from the state of FIG. 34. In this case, the eighth link 17b revolves with respect to the first drive shaft 31a in the counterclockwise direction of the drawing and the arm part 410 revolves forward. At this time, since the sixth link 15c connected to the third drive shaft 31b does not revolve, the rhombus structure formed by the fourth link 15a, the sixth link 15c, the seventh link 17a, and the ninth link 17c vertically extends. Accordingly, the first link 11a is separated from the axis A while moving forward, and accordingly, the tip of the support part 450 gets away from the axis A while the support part 450 moves forward.

Figure 38:
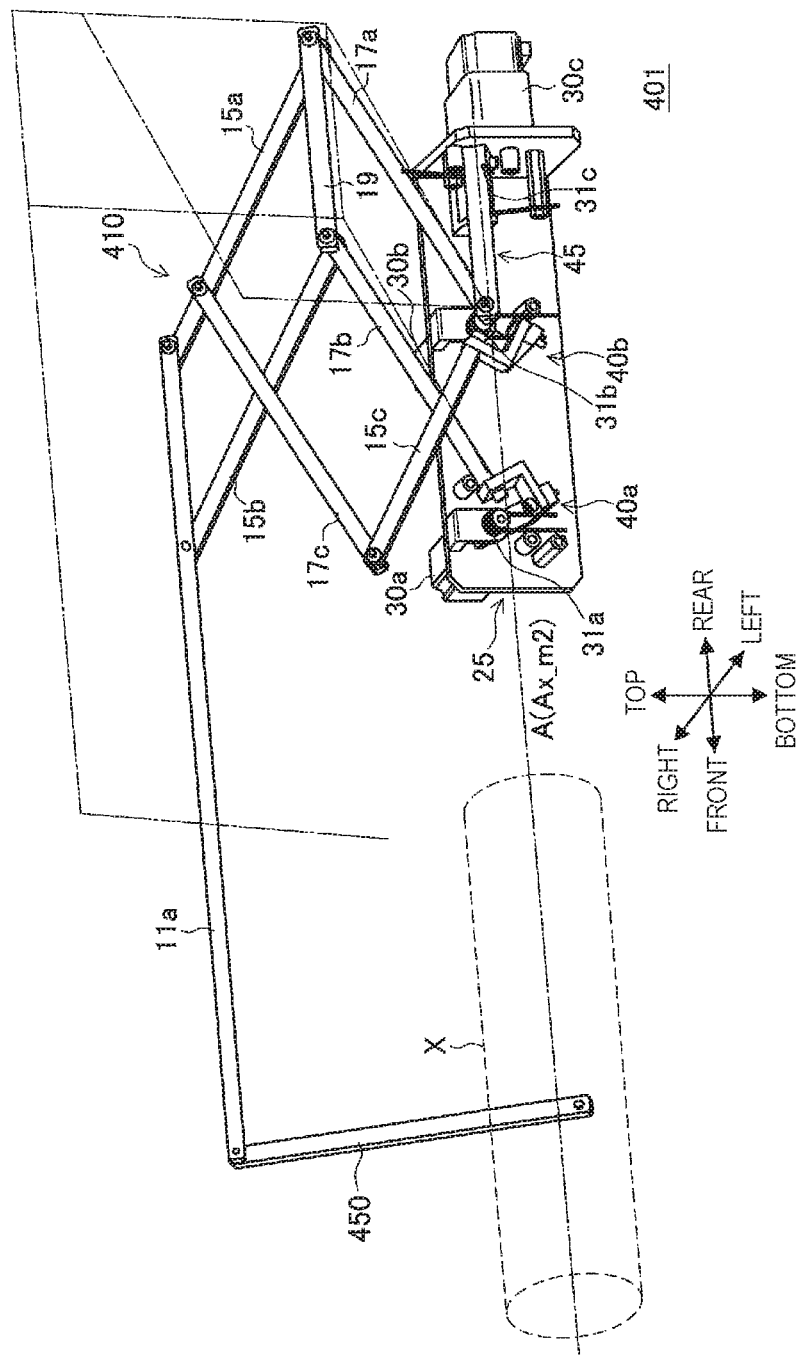
FIG. 38 is a diagram for describing change of an attitude of the arm part.

FIG. 38 shows an attitude of the arm part 410 in a case in which the third motor 30b rotates in the counterclockwise direction of the drawing from the state of FIG. 34. In this case, the sixth link 15c revolves with respect to the third drive shaft 31b in the counterclockwise direction, and the rhombus structure formed by the fourth link 15a, the sixth link 15c, the seventh link 17a, and the ninth link 17c vertically contracts while extending horizontally. At this time, the fourth link 15a and the fifth link 15b are inclined keeping a state parallel to each other. Accordingly, the first link 11a gets closer to the axis A while moving forward, and accordingly, the tip of the support part 450 gets closer to the axis A while the support part 450 moves forward.

Figure 39:
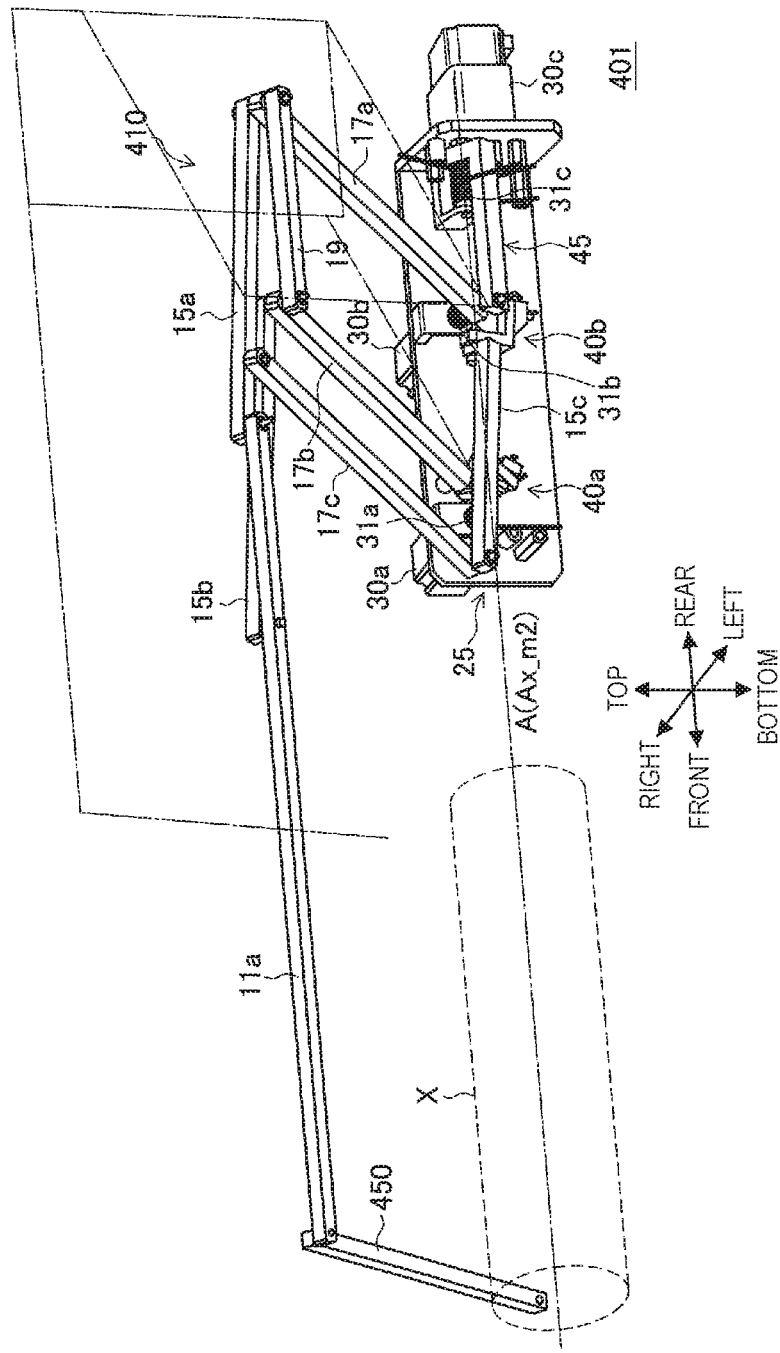
FIG. 39 is a diagram for describing change of an attitude of the arm part.

FIG. 39 shows an attitude of the arm part 410 in a case in which the third motor 30b rotates in the counterclockwise direction of the drawing and the second motor 30c rotates in the left direction from the state of FIG. 36. In this case, by the third motor 30b being driven, the sixth link 15c revolves with respect to the third drive shaft 31b in the counterclockwise direction, and the rhombus structure formed by the fourth link 15a, the sixth link 15c, the seventh link 17a, and the ninth link 17c vertically contracts while extending horizontally. At this time, the fourth link 15a and the fifth link 15b are inclined forward keeping the parallel state. Accordingly, the first link 11a gets closer to the axis A while moving forward. In addition, by the second motor 30c being driven, the link configuration plane revolves with respect to the second drive shaft 30c in the left direction and the axis of the support part 450 is inclined to the left. Accordingly, the tip of the support part 450 gets closer to the axis A while the support part 450 is inclined to the left.

Figure 40:
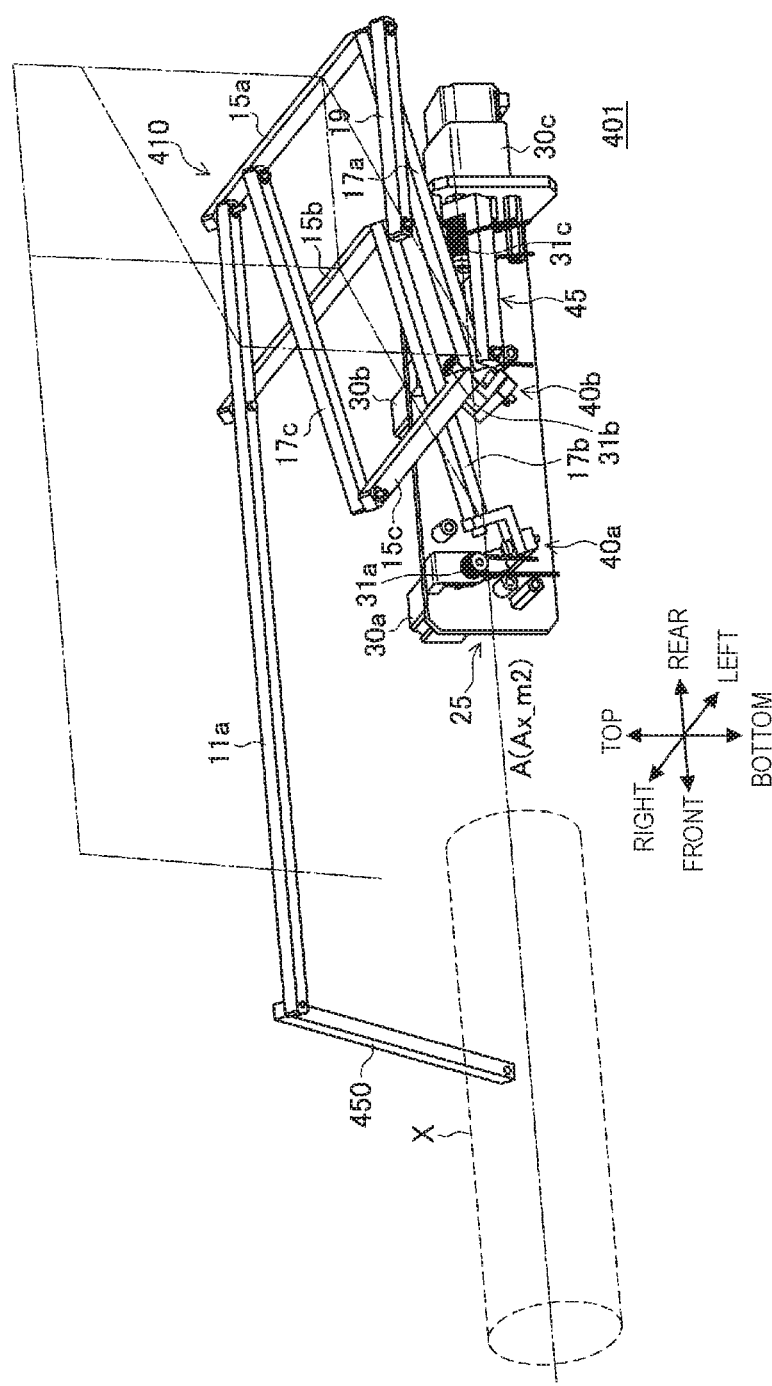
FIG. 40 is a diagram for describing change of an attitude of the arm part.

FIG. 40 shows an attitude of the arm part 410 in a case in which the first motor 30a and the third motor 30b each rotate in the clockwise direction of the drawing from the state of FIG. 39. In this case, by the first motor 30a being driven, the eighth link 17b revolves with respect to the first drive shaft 31a in the clockwise direction and the arm part 410 moves backward. In addition, since the sixth link 15c revolves with respect to the third drive shaft 31b in the clockwise direction by the third motor 30b being driven, the rhombus structure formed by the fourth link 15a, the sixth link 15c, the seventh link 17a, and the ninth link 17c revolves backward keeping its shape. Thus, the first link 11a moves backward, and the support part 450 moves backward accordingly.

As exemplified above, the support arm device 401 according to the present embodiment can have the support part 450 perform rotational motions with respect to the axis A and perform translational motions such that the axis of the support part 450 passes through the axis A by driving each of the first motor 30a, the second motor 30c, and the third motor 30b to control attitudes of the arm part 410. The support arm device 401 according to the present embodiment can be applied to operations of, for example, approaching a substantially columnar object X having the axis A as the center thereof toward an outer circumferential surface thereof from various angles as shown in FIG. 33 to FIG. 40.

<3-3. Conclusion>

As described above, the support arm device 401 according to the present embodiment can cause a tool supported by the arm part 410 to perform translational motions such that the axis of the tool passes through the axis A while causing the tool to perform rotational motions with respect to the predetermined axis A by changing attitudes of the arm part 410. The support arm device 401 can also obtain effects similar to those of the support arm device 1 according to the first embodiment.

Note that, although the support part 450 is fixed to the first link 11a at an angle of 90° in the example of the support arm device 401 according to the present embodiment, the support part 450 may be fixed to the first link 11a at a desired angle. By holding the support part 450 and the first link 11a at an appropriate angle, the device can approach a predetermined target in a state in which the appropriate angle is maintained.

4. Fourth Embodiment

Next, a support arm device according to a fourth embodiment will be described.

Although the support arm devices according to the first and second embodiments perform pivotal motions and translational motions such that a tool such as a surgical instrument or an axis of the tool passes through the RCM, a support arm device according to the present embodiment can only perform pivotal motions such that an axis of a tool passes through the RCM. Differences from the support arm device 305 according to the second embodiment will be described below.

<4-1. Configuration of Support Arm Device>

Figure 41:
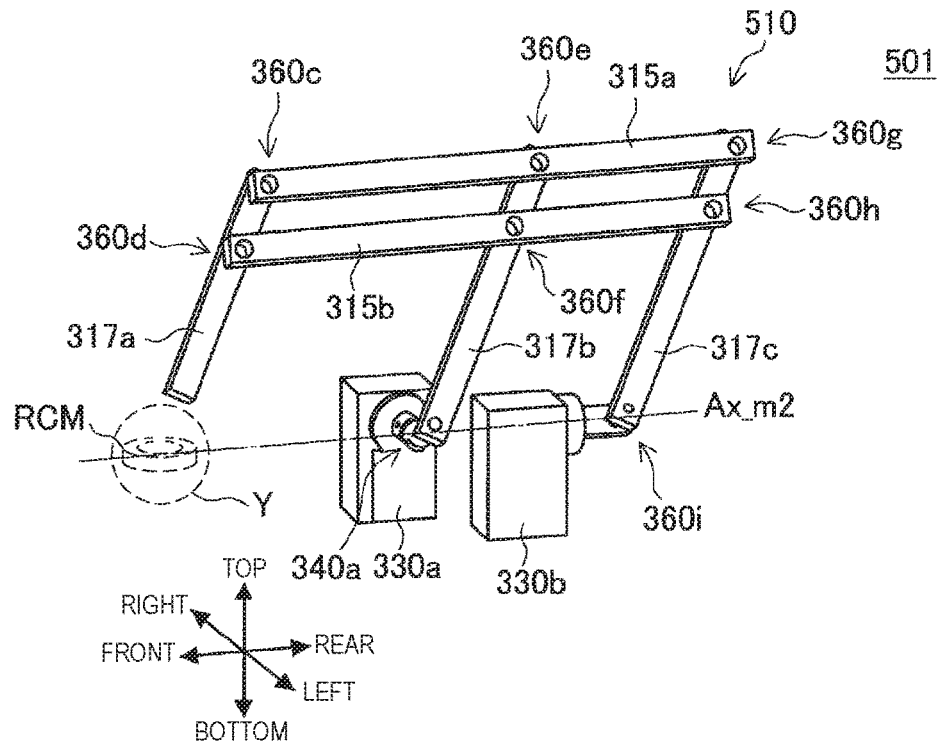
FIG. 41 is a perspective diagram showing an example of a configuration of a support arm device according to a fourth embodiment of the present disclosure.

FIG. 41 is a perspective diagram showing an example of a configuration of a support arm device 501 according to the present embodiment. The support arm device 501 is a device obtained by omitting the first link 311, the second link 313, the guide structure 370, and the third motor 330c from the support arm device 305 according to the second embodiment shown in FIG. 27. In the support arm device 501, for example, a fifth link 317a may be a support part that supports a tool such as a surgical instrument.

By drive of a first motor 330a and a second motor 330b in the support arm device 501, the fifth link 317a revolves with respect to the RCM with an axis of the fifth link 317a that supports a tool set to pass through the RCM. Meanwhile, since a first link, a second link, a guide structure, and a third motor are omitted, no translational motions of the fifth link 317a are performed.

<4-2. Attitude of Arm Part>

Next, various attitudes that an arm part 510 of the support arm device 501 can take will be described. FIG. 42 to FIG. 45 show examples of attitudes of the arm part 510 performing pivotal motion of the fifth link 317a with respect to the RCM. In FIG. 42 to FIG. 45, virtual lines indicating the attitude (a basic attitude) of the arm part 510 of FIG. 41 are shown in order to facilitate comparison to the attitude of the arm part 510 of FIG. 41.

Figure 42:
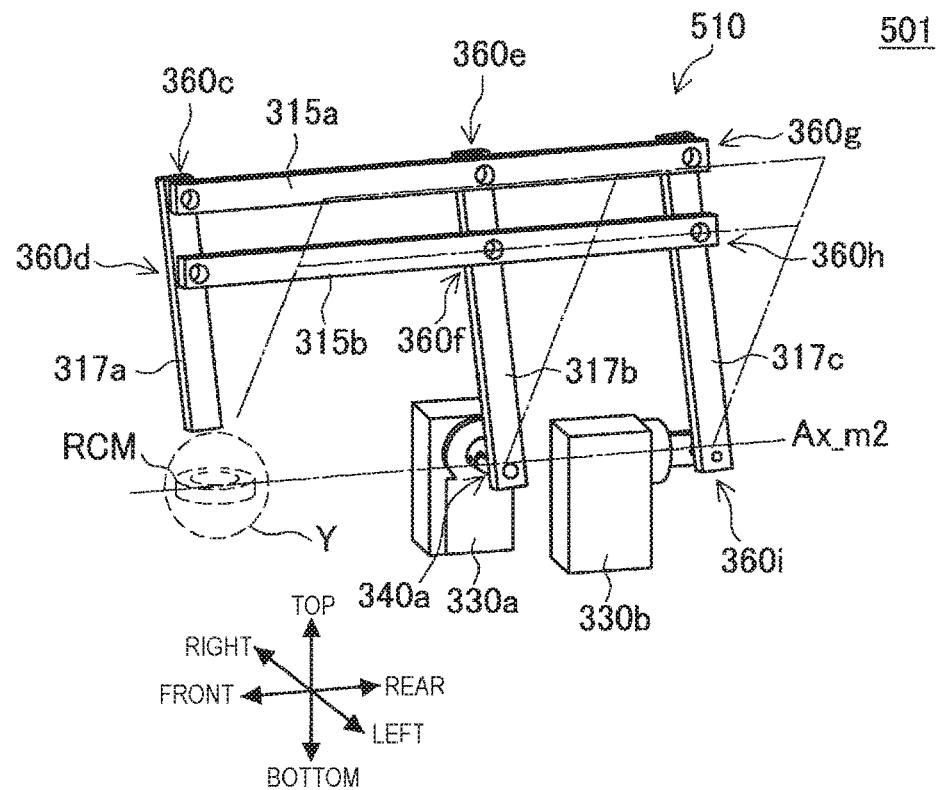
FIG. 42 is a diagram for describing change of an attitude of the arm part.

FIG. 42 shows an attitude of the arm part 510 in a case in which the first motor 330a rotates in the counterclockwise direction of the drawing and the second motor 330b rotates in the left direction from the state of FIG. 41. In this case, the arm part 510 revolves forward while revolving in the left direction in a state in which a third link 315a and a fourth link 315b maintain parallel to each other. Accordingly, the fifth link 317a is inclined forward revolving with respect to the RCM in the left direction.

Figure 43:
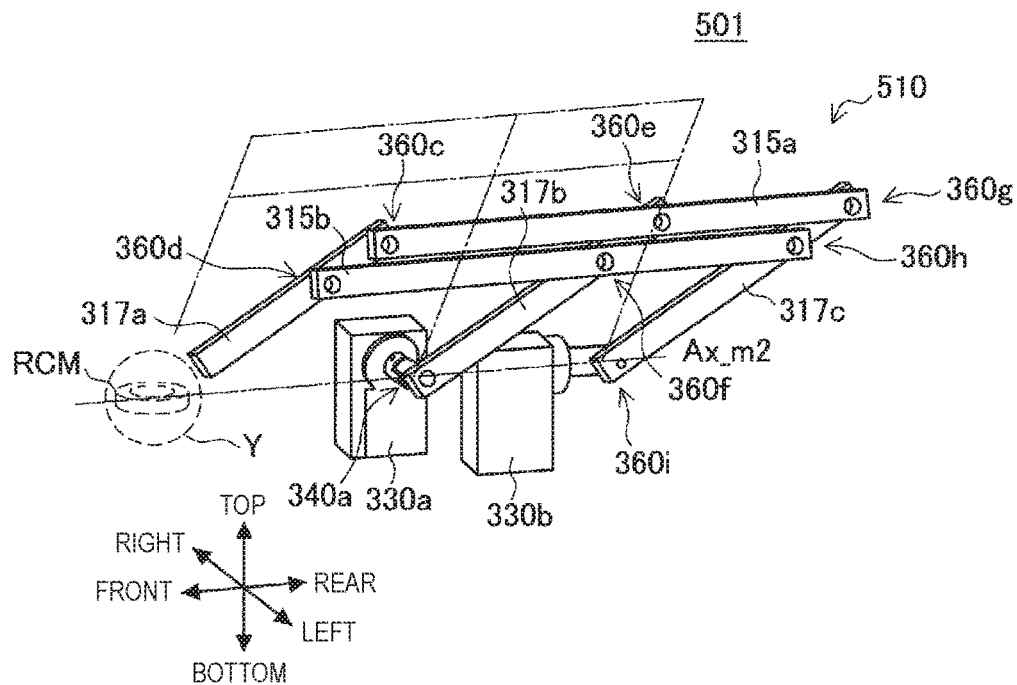
FIG. 43 is a diagram for describing change of an attitude of the arm part.

FIG. 43 shows an attitude of the arm part 510 in a case in which the first motor 330a rotates in the clockwise direction of the drawing from the state of FIG. 42. In this case, the arm part 510 revolves backward in a state in which the third link 315a and the fourth link 315b maintain parallel to each other. Accordingly, the fifth link 317a is inclined to the rear with respect to the RCM.

Figure 44:
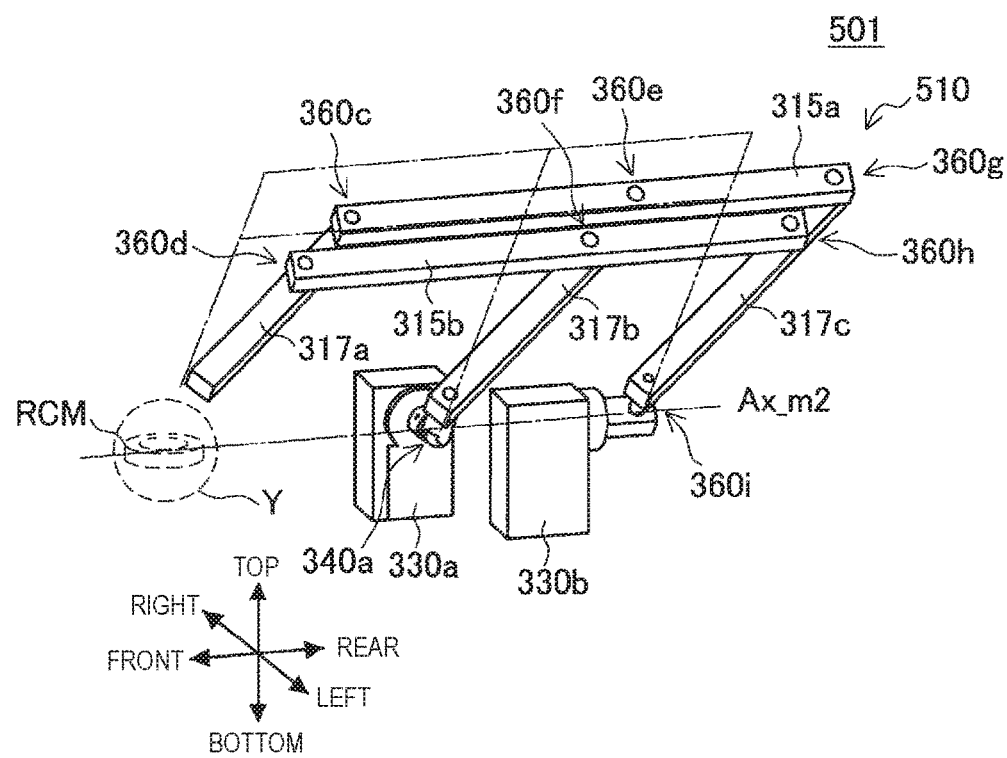
FIG. 44 is a diagram for describing change of an attitude of the arm part.

FIG. 44 shows an attitude of the arm part 510 in a case in which the second motor 330b rotates in the right direction from the state of FIG. 43. In this case, the arm part 510 is inclined to the right. Accordingly, the fifth link 317a is inclined to the right with respect to the RCM. At this time, since a sixth link 317b is connected to the output shaft of the first motor 330a via a universal joint 340a, rotational motions of the sixth link 317b are not obstructed.

Figure 45:
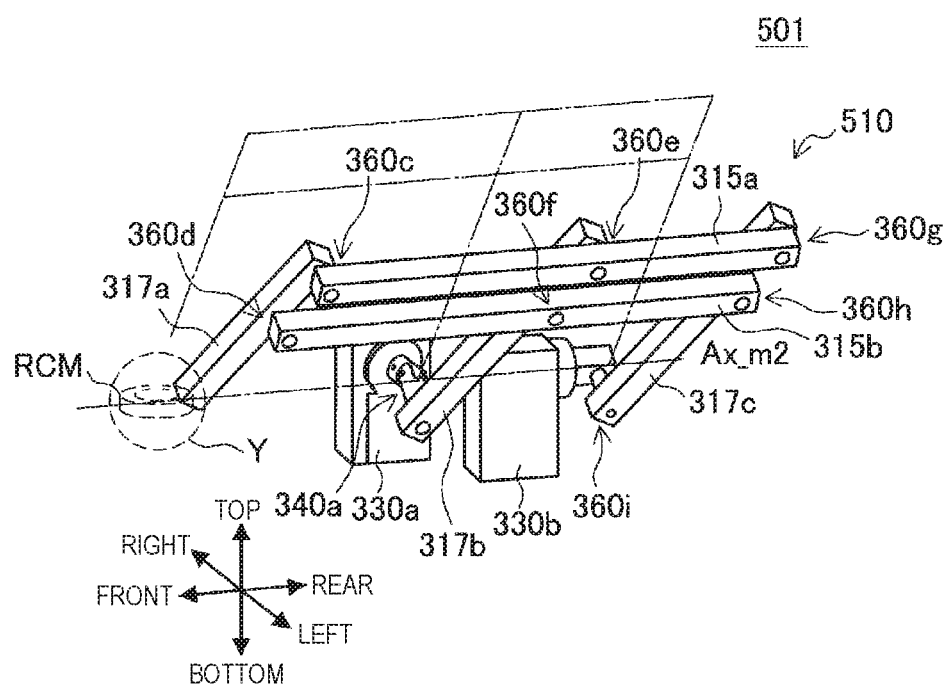
FIG. 45 is a diagram for describing change of an attitude of the arm part.

FIG. 45 shows an attitude of the arm part 510 in a case in which the second motor 330b rotates in the left direction from the state of FIG. 41. In this case, the arm part 510 is inclined to the left. Accordingly, the fifth link 317a is inclined to the left with respect to the RCM. At this time, since the sixth link 317b is connected to the first motor 330a via the universal joint 340a, rotational motions of the sixth link 317b are not obstructed.

As exemplified above, the support arm device 501 according to the present embodiment can cause the fifth link 317a which supports a tool such as a surgical instrument to perform pivotal operations with respect to the RCM by driving each of the first motor 330a and the second motor 330b and changing an attitude of the arm part 510. The support arm device 501 according to the present embodiment can be applied to an operation of, for example, approaching a spherical surface Y having the RCM as the center thereof at various angles as shown in FIG. 42 to FIG. 45.

<4-3. Conclusion>

As described above, the support arm device 501 according to the present embodiment can cause a tool supported by the arm part 510 to perform pivotal motions with respect to the RCM by changing attitudes of the arm part 510. The support arm device 501 can gain effects similar to those of the support arm device 1 according to the first embodiment as well.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

In the support arm device according to the first embodiment, for example, lengths of the first link 11a and the second link 11b may be set to be adjustable. Specifically, the first link 11a and the second link 11b may be replaceable by selecting appropriate links from various links having different lengths. Alternatively, the first link 11a and the second link 11b may be set to be stretchable. Accordingly, the position of the RCM can be changed in accordance with the physique of a patient or the like. Likewise, a length of each of links constituting the support arm device according to each embodiment described above may be set to be adjustable. Accordingly, a position from which a tool approaches a target can be changed in accordance with the physique of a patient or the like.

In addition, although examples in which the support arm device is used as a medical support arm device have been described in the embodiments, an application of the support arm device is not limited thereto. The support arm device may be installed on production lines or the like and used for industrial applications. For example, two support arm devices may be used to find angles of a camera and lighting that help scratches, contamination, or the like of certain products easily observed or viewed. In this case, one of the support arm devices may support the camera and the other support arm device may support a lighting device. Thus, an operator or the like can find out a combination angle of the camera and lighting that help scratches, contamination, or the like easily viewed from a captured image while variously changing attitudes of each of the support arm devices. Accordingly, an attitude of an arm part of each of the support arm devices can be fixed in accordance with the angle on the production line or the like and thus presence of scratches, contamination, or the like of products can be properly determined.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A support arm device including:

a first drive part configured to be fixed to a base part and cause a first drive shaft to perform shaft rotation;

a second drive part configured to be fixed to the base part and cause a second drive shaft to perform shaft rotation; and an arm part including at least one parallel link and configured to support a predetermined tool, in which the arm part is caused to change an attitude to cause the predetermined tool to perform a rotational motion by the first drive part and the second drive part being driven.

(2)

The support arm device according to (1), further including:

a third drive part configured to be fixed to the base part and cause a third drive shaft to perform shaft rotation, in which the arm part is caused to change an attitude to cause the predetermined tool to perform a pivotal motion with respect to a remote center of motion as the predetermined rotational motion and to perform a translational motion along a straight line passing through the remote center of motion by the first drive part, the second drive part, and the third drive part being driven.

(3)

The support arm device according to (1) or (2), in which the arm part includes a plurality of parallel links, and the plurality of parallel links are present within a link configuration plane.

(4)

The support arm device according to (2) or (3), in which, while the arm part serves as a part that is movable by the first drive part, the second drive part, and the third drive part being driven, the base part serves as a part that is immovable by the first drive part, the second drive part, and the third drive part being driven.

(5)

The support arm device according to any one of (2) to (4), including:

a first orthogonal joint part configured to be interposed between a first drive link constituting the arm part and the first drive shaft to constitute orthogonal three degrees of freedom;

a second orthogonal joint part configured to be interposed between a second drive link constituting the arm part and the second drive shaft to constitute orthogonal two degrees of freedom; and a third orthogonal joint part configured to be interposed between a third drive link constituting the arm part and the third drive shaft to constitute orthogonal three degrees of freedom.

(6)

The support arm device according to any one of (2) to (5), in which an axis of the first drive shaft and an axis of the third drive shaft are present on planes that are parallel to each other.

(7)

The support arm device according to (6), in which the axis of the first drive shaft and the axis of the third drive shaft are disposed to be in an equidistant parallel state or on a same axis.

(8)

The support arm device according to (6) or (7), in which an axis of the second drive shaft is orthogonal to the axis of the first drive shaft and the axis of the third drive shaft.

(9)

The support arm device according to any one of (2) to (8), in which the remote center of motion is present on an axis of the second drive shaft.

(10)

The support arm device according to any one of (2) to (9), in which, by causing the first drive shaft and the third drive shaft to perform shaft rotation in a same direction, the tool revolves with the remote center of motion serving as a rotation center.

(11)

The support arm device according to any one of (2) to (10), in which, by causing the first drive shaft and the third drive shaft to perform shaft rotation in a reverse direction, the tool performs a translational motion along a straight line passing through the remote center of motion.

(12)

The support arm device according to (11), in which the arm part includes a linear bushing configured to guide the translational motion.

(13)

The support arm device according to (12), in which the arm part includes a parallel link including one side on a straight line passing through the remote center of motion, and a guide pin that is disposed in a direction parallel to the straight line passing through the remote center of motion and is able to move forward and backward in the linear bushing in the direction is provided in the parallel link.

(14)

The support arm device according to (13), in which the guide pin is disposed on a straight line orthogonal to an axis of the first drive shaft or an axis of the third drive shaft.

(15)

The support arm device according to (13) or (14), in which, two sides intersecting with the one side of the parallel link including the one side on the straight line passing through the remote center of motion move while maintaining a state parallel to an axis of the second drive shaft.

(16)

The support arm device according to any one of (3) to (15), in which the tool rotates in a direction intersecting with the link configuration plane due to shaft rotation of the second drive shaft.

(17)

The support arm device according to any one of (5) to (16), including:

a stopper configured to regulate a revolution range of the first drive link in a shaft rotation direction of the first drive shaft.

(18)

The support arm device according to any one of (5) to (17), including:

a stopper configured to regulate a revolution range of the second drive link in a shaft rotation direction of the second drive shaft.

(19)

The support arm device according to any one of (1) to (18), in which the tool is a medical instrument.

(20)

The support arm device according to (19), in which the tool is an endoscope or an end-effector that grips a biological tissue of a patient or a medical device.

REFERENCE SIGNS LIST 1 support arm device
5 surgical instrument (tool)
10 arm part
15c sixth link (third drive link)
17a seventh link (second drive link)
17b eighth link (first drive link)
21 base part
31a first drive shaft
31b third drive shaft
31c second drive shaft
35 guide structure
40a first orthogonal join part
40b third orthogonal join part
40c second orthogonal join part
42 linear bushing
43 guide pin
60a to 60n joint part

The invention claimed is:

1. A support arm device, comprising:
   a first drive part, fixed to a base part, configured to rotate a first drive shaft;
   a second drive part, fixed to the base part, configured to rotate a second drive shaft; and
   an arm part, including at least one parallel link configured to support a tool, wherein
      the tool is an endoscope,
      the arm part is configured to move the tool in a rotational motion, with respect to a remote center of motion, based on a drive operation of the first drive part and the second drive part, and
      the remote center of motion is present on an axis of the second drive shaft.

2. The support arm device according to claim 1, further comprising a third drive part, fixed to the base part, configured to rotate a third drive shaft, wherein
   the arm part is configured to move the tool, based on the drive operation of the first drive part, the second drive part, and the third drive part, and
   the motion of the tool comprises a pivotal motion with respect to the remote center of motion as the rotational motion and a translational motion along a straight line passing through the remote center of motion.

3. The support arm device according to claim 2, wherein
   the arm part is movable by the drive operation of the first drive part, the second drive part, and the third drive part, and
   the base part is immovable by the drive operation of the first drive part, the second drive part, and the third drive part.

4. The support arm device according to claim 2, comprising:
   a first orthogonal joint part interposed between a first drive link constituting the arm part and the first drive shaft to constitute orthogonal three degrees of freedom;
   a second orthogonal joint part interposed between a second drive link constituting the arm part and the second drive shaft to constitute orthogonal two degrees of freedom; and
   a third orthogonal joint part interposed between a third drive link constituting the arm part and the third drive shaft to constitute the orthogonal three degrees of freedom.

5. The support arm device according to claim 4, comprising a stopper configured to regulate a revolution range of the first drive link in a rotation direction of the rotation of the first drive shaft.

6. The support arm device according to claim 4, comprising a stopper configured to regulate a revolution range of the second drive link in a rotation direction of the rotation of the second drive shaft.

7. The support arm device according to claim 2, wherein
   an axis of the first drive shaft is present on a first plane,
   an axis of the third drive shaft is present on a second plane, and
   the first plane is parallel to the second plane.

8. The support arm device according to claim 7, wherein the axis of the first drive shaft and the axis of the third drive shaft are in one of an equidistant parallel state or on a same axis.

9. The support arm device according to claim 7, wherein an axis of the second drive shaft is orthogonal to both the axis of the first drive shaft and the axis of the third drive shaft.

10. The support arm device according to claim 2, wherein the tool revolves with the remote center of motion serving as a rotation center based on the rotation of the first drive shaft and the third drive shaft in a same direction.

11. The support arm device according to claim 2, wherein the tool moves in the translational motion along the straight line passing through the remote center of motion based on the rotation of the first drive shaft and the third drive shaft in opposite directions.

12. The support arm device according to claim 11, wherein the arm part comprises a linear bushing configured to guide the translational motion.

13. The support arm device according to claim 12, wherein
   the arm part comprises
      a parallel link including one side on the straight line passing through the remote center of motion, and
      a guide pin in a direction parallel to the straight line passing through the remote center of motion, and
   the guide pin is configured to move forward and backward in the linear bushing.

14. The support arm device according to claim 13, wherein the guide pin is disposed on the straight line which is orthogonal to at least one of an axis of the first drive shaft or an axis of the third drive shaft.

15. The support arm device according to claim 13, wherein, two sides, which intersect the one side of the parallel link on the straight line, move in a state parallel to an axis of the second drive shaft.

16. The support arm device according to claim 1, wherein
   the arm part comprises a plurality of parallel links, and
   the plurality of parallel links is present within a link configuration plane.

17. The support arm device according to claim 16, wherein the tool rotates in a direction that intersects with the link configuration plane due to the rotation of the second drive shaft.

* * * * *